(12) United States Patent
Lollar

(10) Patent No.: US 6,458,563 B1
(45) Date of Patent: Oct. 1, 2002

(54) MODIFIED FACTOR VIII

(75) Inventor: John S. Lollar, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/523,656

(22) Filed: Mar. 10, 2000

Related U.S. Application Data

(63) Continuation-in-part of application No. 09/037,601, filed on Mar. 10, 1998, now Pat. No. 6,180,371, which is a continuation-in-part of application No. 08/670,707, filed on Jun. 26, 1996, now Pat. No. 5,859,204, application No. 09/523,656, which is a continuation-in-part of application No. PCT/US97/11155, filed on Jun. 26, 1997.

(51) Int. Cl.[7] .......................... C12P 21/00; C12N 15/00; C12N 15/09; C12N 5/10
(52) U.S. Cl. .................. 435/69.6; 435/69.1; 435/320.1; 435/325; 514/2; 514/8; 514/44; 514/802; 514/834; 530/383; 536/23.1
(58) Field of Search .............................. 435/69.1, 69.6, 435/325, 320.1; 514/2, 8, 802, 834, 44; 530/383; 536/23.1

(56) References Cited

U.S. PATENT DOCUMENTS

| | | | |
|---|---|---|---|
| 4,757,006 A | 7/1988 | Toole | 435/70 |
| 5,364,771 A | 11/1994 | Lollar | 435/69.1 |
| 5,563,045 A | 10/1996 | Pittman et al. | 435/69.6 |
| 5,663,060 A | 9/1997 | Lollar et al. | 435/69.6 |

FOREIGN PATENT DOCUMENTS

| | | | |
|---|---|---|---|
| EP | 0 306 968 A2 | 9/1988 | C12N/15/00 |
| WO | WO 91/07438 | 11/1990 | C07K/15/06 |
| WO | WO 94/11503 | 5/1994 | |
| WO | WO 97/03191 | 1/1997 | C12N/15/12 |
| WO | WO 97/03193 | 1/1997 | C12N/15/12 |

OTHER PUBLICATIONS

Verma et al. Gene Therapy– promises, problems and prospects, (Sep. 1997), Nature, vol. 389, pp. 239–242.*
Church, et al. "Coagulation factors V and VIII and ceruloplasmin constitute a family of structurally related proteins"; (1984) *Proc. Natl. Acad. Sci. USA* 81:6934.
Gitcher, J. et al. Characterization of the human factor VIII gene; (1984) *Nature* 312:326–330.
Lubin, et al. "Elimination of a Major Inhibitor Epitope in Factor VIII"; (1994) *J. Biol. Chem.* 269:8639–8641.
Scandella, D. et al. "Some Factor VIII Inhibitor Antibodies Recognize a Common Epitope Corresponding to C2 Domain Amino Acids 2248 Through 2312, Which Overlap a Phospholipid–Binding Site"; (1995) *Blood* 86:1811–1819.

Toole, et al. "Molecular cloning of a cDNA encoding human antihaemophilic factor"; (1984) *Nature* 312:342–347.
Toole, et al. "A large region ($\approx$ 95 kDa) of human factor VIII is dispensable for in vitro procoagulant activity"; (1986) *Proc. Natl. Acad. Sci. USA* 83:5939–5942.
Dominguez, O. et al. "Gene walking by unpredictably primed PCR"; (1994) *Nucleic Acids Res.* 22:3247–3248.
Fulcher, C.A. et al. "Localization of human factor FVIII inhibitor epitopes to two polypeptide fragments"; (1985) *Proc. Natl. Acad. Sci. USA* 82:7728–7732.
Healy, J.F. et al. "The cDNA and Derived Amino Acid Sequence of Porcine Factor VIII"; (1996) *Blood* 88:4209–4214.
Nakai, H. et al. "Properties of Affinity Purified Anti–factor VIII Antibodies from Patients with Factor VIII Inhibitors"; (1994) *Blood* 84:224a.
Ochman, H. et al. "Inverse Polymerase Chain Reaction"; (1990) *Biotech. N.Y.* 8:759–760.
Parker, J.D. et al. "Targeted gene–walking polymerase chain reaction"; (1991) *Nucleic Acids. Res.* 19:3055–3060.
Parker, J.D. et al. "The Oligomer Extension 'Hot Blot'; A Rapid Alternative to Southern Blots for Analyzing Polymerase Chain Reaction Products"; (1991) *Biotechniques* 10:94–101.
Sarkar, G. et al. "Restriction–site PCR: A Direct Method of Unknown Sequence Retrieval Adjacent to a Known Locus by Using Universal Primers"; (1993) *PCK Meth. Appl.* 2:318–322.
Scandella, D. et al. "Localization of epitopes for human factor VIII inhibitor antibodies by immunoblotting and antibody neutralization" (1989) *Blood* 74:1618–1626.
Scandella, D. et al. "A recombinant factor VIII A2 domain polypeptide quantitatively neutralizes human inhibitor antibodies that bind to A2"; (1993) *Blood* 82(6):1767–1775.
Scandella, D. et al. "Epitope mapping of human factor VIII inhibitor antibodies by deletion analysis of actor VIII fragments expressed in *Escherichia coli*"; (1988) *Proc. Natl. Acad. Sci. USA* 85:6152–6156.
Siebert, P.D. et al. "An improved PCR method for walking in unclosed gnomic DNA"; (1995) *Nucleic Acids Res.* 23:1087–1088.
Eaton, D.L. et al. "Construction and Characterization of an Active Factor VIII Variant Lacking the Central One–Third of the Molecule" (1986) *Biochemistry* 25(26):8343–8347.

* cited by examiner

Primary Examiner—Christopher S. F. Low
Assistant Examiner—Holly Schnizer
(74) *Attorney, Agent, or Firm*—Greenlee Winner and Sullivan PC

(57) ABSTRACT

The invention relates to a modified B-domainless form of porcine factor VIII, to a DNA encoding the same, and to the use thereof for treatment of hemophilia.

10 Claims, 6 Drawing Sheets

Signal peptide

```
Human  -19  MQIELSTCFF  LCLLRFCFS
Pig         MQLELSTCVF  LCLLPLGFS
Mouse       MQIALFACFF  LSLFNFCSS
            **  *  * * * *    *
```

FIG. 1A

A1 domain

```
Human   1   ATRRYYLGAV  ELSWDYMQSD  LG-ELPVDAR  FPPRVPKSFP  FNTSVVYKKT
Pig         AIRRYYLGAV  ELSWDYRQSE  LLRELHVDTR  FPATAPGALP  LGPSVLYKKT
Mouse       AIRRYYLGAV  ELSWNYIQSD  LLSVLHTDSR  FLPRMSTSFP  FNTSIMYKKT
            **********  **** * **    *   * * *       *     *  ****
```

FIG. 1B

```
        50  LFVEFTDHLF  NIAKPRPPWM  GLLGPTIQAE  VYDTVVITLK  NMASHPVSLH
            VFVEFTDQLF  SVARPRPPWM  GLLGPTIQAE  VYDTVVVTLK  NMASHPVSLH
            VFVEYKDQLF  NIAKPRPPWM  GLLGPTIWTE  VHDTVVITLK  NMASHPVSLH
            ***  *  **    *  ******  ******  *  * ****  ***  **********

100  AVGVSYWKAS  EGAEYDDQTS  QREKEDDKVF  PGGSHTYVWQ  VLKENGPMAS
            AVGVSFWKSS  EGAEYEDHTS  QREKEDDKVL  PGKSQTYVWQ  VLKENGPTAS
            AVGVSYWKAS  EGDEYEDQTS  QMEKEDDKVF  PGESHTYVWQ  VLKENGPMAS
            *****  **  *  **  ****  **  * *******  **  * ****  *******  **

150  DPLCLTYSYL  SHVDLVKDLN  SGLIGALLVC  REGSLAKEKT  QTLHKFILLF
            DPPCLTYSYL  SHVDLVKDLN  SGLIGALLVC  REGSLTRERT  QNLHEFVLLF
            DPPCLTYSYM  SHVDLVKDLN  SGLIGALLVC  KEGSLSKERT  QMLYQFVLLF
            *********   **********  **********  ****   *  *    *  ***

200  AVFDEGKSWH  SETKNSLMQD  RDAASARAWP  KMHTVNGYVN  RSLPGLIGCH
            AVFDEGKSWH  SARNDSWTRA  MDPAPARAQP  AMHTVNGYVN  RSLPGLIGCH
            AVFDEGKSWH  SETNDSYTQS  MDSASARDWP  KMHTVNGYVN  RSLPGLIGCH
            **********   *    *      *  **  *    **********  **********

250  RKSVYWHVIG  MGTTPEVHSI  FLEGHTFLVR  NHRQASLEIS  PITFLTAQTL
            KKSVYWHVIG  MGTSPEVHSI  FLEGHTFLVR  HHRQASLEIS  PLTFLTAQTF
            RKSVYWHVIG  MGTTPEIHSI  FLEGHTFFVR  NHRQASLEIS  PITFLTAQTL
            *********  ***  **  ***  *******  **  **********  ********
                                                        APC/IXa          ♦
       300  LMDLGQFLLF  CHISSHQHDG  MEAYVKVDSC  PEEPQLRMKN  NEEAEDYDDD
            LMDLGQFLLF  CHISSHHHGG  MEAHVRVESC  AEEPQLRRKA  DE-EEDYDDN
            LIDLGQFLLF  CHISSHKHDG  MEAYVKVDSC  PEESQWQKKN  NN-EEMEDYD
            *  ********  ******  *  ***   *  **   **   *       *   *
                                    IIa/Xa
       350  LTDSEMDVVR  FDDDNSPSFI  QIR
            LYDSDMDVVR  LDGDDVSPFI  QIR
            DDLYSEMDMF  TLDYDSSPFI  QIR
                        **  ***
```

```
A2 domain
Human   373 SVAKKHPKTW VHYIAAEEED WDYAPLVLAP DDRSYKSQYL NNGPQRIGRK     FIG. 1C
Pig         SVAKKHPKTW VHYISAEEED WDYAPAVPSP SDRSYKSLYL NSGPQRIGRK
Mouse       SVAKKYPKTW IHYISAEEED WDYAPSVPTS DNGSYKSQYL SNGPHRIGRK
            ***** ****  *** ***** ***** *     **** **  ** *****

423 YKKVRFMAYT DETFKTREAI QHESGILGPL LYGEVGDTLL IIFKNQASRP
            YKKARFVAYT DVTFKTRKAI PYESGILGPL LYGEVGDTLL IIFKNKASRP
            YKKVRFIAYT DETFKTRETI QHESGLLGPL LYGEVGDTLL IIFKNQASRP
            *** ** ***  * *****  *   *** **** ********** ***** ****
                                 A2 Inhibitor epitope
        473 YNIYPHGITD VRPLYSRRLP KGVKHLKDFP ILPGEIFKYK WTVTVEDGPT
            YNIYPHGITD VSALHPGRLL KGWKHLKDMP ILPGETFKYK WTVTVEDGPT
            YNIYPHGITD VSPLHARRLP RGIKHVKDLP IHPGEIFKYK WTVTVEDGPT
            **********  *    **   ** ** **  *  *** **** **********
                                             F.IXa binding
                                                   APC
        523 KSDPRCLTRY YSSFVNMERD LASGLIGPLL ICYKESVDQR GNQIMSDKRN
            KSDPRCLTRY YSSSINLEKD LASGLIGPLL ICYKESVDQR GNQMMSDKRN
            KSDPRCLTRY YSSFINPERD LASGLIGPLL ICYKESVDQR GNQMMSDKRN
            **********  ***  * *  ********** **********  *** *****

573 VILFSVFDEN RSWYLTENIQ RFLPNPAGVQ LEDPEFQASN IMHSINGYVF
            VILFSVFDEN QSWYLAENIQ RFLPNPDGLQ PQDPEFQASN IMHSINGYVF
            VILFSIFDEN QSWYITENMQ RFLPNAAKTQ PQDPGFQASN IMHSINGYVF
            ***** ****  *** ** *  *****        **  **** **********

623 DSLQLSVCLH EVAYWYILSI GAQTDFLSVF FSGYTFKHKM VYEDTLTLFP
            DSLQLSVCLH EVAYWYILSV GAQTDFLSVF FSGYTFKHKM VYEDTLTLFP
            DSLELTVCLH EVAYWHILSV GAQTDFLSIF FSGYTFKHKM VYEDTLTLFP
            *** * **** ***** ***  ******** * ********** **********
                                                                 ♦♦
        673 FSGETVFMSM ENPGLWILGC HNSDFRNRGM TALLKVSSCD KNTGDYYEDS
            FSGETVFMSM ENPGLWVLGC HNSDLRNRGM TALLKVYSCD RDIGDYYDNT
            FSGETVFMSM ENPGLWVLGC HNSDFRKRGM TALLKVSSCD KSTSDYYEEI
            ********** ****** ** ****  * ** ****** ***  *  **
               ♦               IIa/Xa/APC
        723 YEDISAYLLS KNNAIEPR
            YEDIPGFLLS GKNVIEPR
            YEDIPTQLVN ENNVIDPR
            ****  *     *  * **
```

```
B domain
Human  741 SFSQNSRHPS TRQKQFNATT IPENDIEKTD PWFAHRTPMP KIQNVSSSDL     FIG. 1D
Pig        SFAQNSRPPS ASQKQFQTIT SPEDDVE-LD PQSGERTQAL EELSVPSGDG
Mouse      SFFQNTNHPN TRKKKFKDST IPKNDMEKIE PQFEEIAEKM KVQSVSVSDM
           ** **  *         *   *  * *  **   *             *   *

791 LMLLRQS-PT PHGLSLSDLQ EAKYETFSDD PSPGAIDSNN SLSEMTHFRP
           SMLLGQN-PA PHGSSSSDLQ EARNEA--DD YLPGARERNT APSAAARLRP
           LMLLGQSHPT PHGLFLSDGQ EAIYEAIHDD HSPNAIDSNE GPSKVTQLRP
           *** *      ***   ***  ** *  **   *  *    *           **

840 QLHHSGDMVF TPESGLQLRL NEKLGTTAAT ELKKLDFKVS ST-SNNLIS-
           ELHHSAERVL TPEP------ -------EK ELKKLDSKMS SSSDLLKTSP
           ESHHSEKIVF TPQPGLQLRS NKSLETTIEV KWKKLGLQVS SLFSNLMTT-
            ***    *  **                    ***   * *

888 TIPSDNLAAGT DNTSSLGPPS MPVHYDSQLD TTLFGKKSSP LTESGGPLSL
           TIPSDTLSAET ERTHSLGPPH PQVNFRSQLG AIVLGKNSSH FIGAGVPLGS
           TILSDNLKATF EKTDSSGFPD MPVHSSSKLS TTAFGKKAYS LVGSHVPLNA
           ** ** *  *     *   *   *  *    *   *  **           **

939 SEENNDSKLL ESGLMNSQES SWGKNVSSTE SGRLFKGKRA HGPALLTKDN
           TEED------ -------HES SLGENVSPVE SDGIFEKERA HGPASLTKDD
           SEENSDSNIL DSTLMYSQES LPRDNILSIE NDRLLREKRF HGIALLTKDN
           **                **  **    *         *      ** * ***

989 ALFKVSISLL KTNKTSNNSA TNRKTHIDGP SLLIENSPSV WQNILESDTE
           VLFKVNISLV KTNKARVYLK TNRKIHIDDA ALLTENRAS- ----------
           TLFKDNVSLM KTNKTYNHST TNEKLHTESP TSIENSTTDL QDAILKVNSE
            ***   **  ****       ** *   *   ** *

1039 FKKVTPLIHD RMLMDKNATA LRLNHMSNKT TSSKNMEMVQ QKKEGPIPPD
           ---------- ATFMDKNTTA SGLNHVSN-- ---------- ----------
           IQEVTALIHD GTLLGKNSTY LRLNHMLNRT TSTKNKDIFH RKDEDPIPQD
                *  ***   **        *** *

1089 AQNPDMSFFK MLFLPESARW IQRTHGKNSL NSGQGPSPKQ LVSLGPEKSV
           ---------- ----------W IKGPLGKNPL SSERGPSPEL LTSSGSGKSV
           EENTIMPFSK MLFLSESSNW FKKTNGNNSL NSEQEHSPKQ LVYLMFKKYV
                        *          *  * *    *   *        *   *  *

1139 EGQNFLSEKN KVVVGKGEFT KDVGLKEMVF PSSRNLFLTN LDNLHENNTH
           KGQSSGQGRI RVAVEEEELS KG---KEMML PNSELTFLTN SADVQGNDTH
           KNQSFLSEKN KVTVEQDGFT KNIGLKDMAF PHNMSIFLTT LSNVHENGRH
             *   *     *     *  * *          *   *         *  *

1189 NQEKKIQEEI EKKETLIQEN VVLPQIHTVT GTKNFMKNLF LLSTRQNVEG
           SQGKKSREEM ERREKLVQEK VDLPQVYTAT GTKNFLRNIF HQSTEPSVEG
           NQEKNIQEEI EK-EALIEEK VVLPQVHEAT GSKNFLKDIL ILGTRQNI--
             *   *     * * *     * *** *  * ***

1239 SYDGAYAPVL QDFRSLNDST NRTKKHTAHF SK--KGEEEN LEGLGNQTKQ
           FDGGSHAPVP QDSRSLNDSA ERAETHIAHF SAIR--EEAP LEAPGNRT--
           SLYEVHVPVL QNITSINNST NTVQIHMEHF FKRRKDKETN SEGLVNKTRE
            *     **  *   *  *   *   *  *   *        *     *  *
```

```
1287  IVEKYACTTR  ISPNTSQQNF  VTQRSKRALK  QFRLPLEETE  LEKRIIVDDT
      ----------  ---GPGPRSA  VPRRVKQSLK  QIRLPLEEIK  PERGYVLNAT
      MVKNYP----  -----SQKNI  TTQRSKRALG  QFRL------  ----------

1337  STQWSKNMKH  LTPSTLTQID  YNEKEKGAIT  QSPLSDCLTR  SHSIPQANRS
      STRWS-----  ----------  ----------  ----------  ----------
      STQWLKTINC  STQCIIKQID  HSKEMKKFIT  KSSLSDS-SV  IKSTTQTNSS
      **  *

1387  PLPIAKVSSF  PSIRPIYLTR  VLFQDNSSHL  PAASY----R  KKDSGVQESS
      ----------  ----------  ----------  ----------  -------ESS
      DSHIVKTSAF  P---PIDLKR  SPFQNKFSHV  QASSYIYDFK  TKSSRIQESN
                                                         **

1433  HFLQGAKKNN  LSLAILTLEM  TGDQREVGSL  GTSATNSVTY  KKVENTVLPK
      PILQGAKRNN  LSLPFLTLEM  AGGQGKISAL  GKSAAGPLAS  GKLEKAVLSS
      NFLKETKINN  PSLAILPWNM  FIDQGKFTSP  GKSNTNSVTY  KKRENIIFLK
       *   * **  **  *   *              *  *        * *

1483  PDLPKTSGKV  ELLPKVHIYQ  KDLFPTETSN  GSPGHLDLVE  GSLLQGTEGA
      AGLSEASGKA  EFLPKVRVHR  EDLLPQKTSN  VSCAHGDLGQ  EIFLQKTRGP
      PTLPEESGKI  ELLPQVSIQE  EEILPTETSH  GSPGHLNLMK  EVFLQKIQGP
        ***     *  ** *        *   *   *             ***   *

1533  IKWNEANRPG  KVPFLRVATE  SSAKTPSKLL  DPLAWDNHYG  TQIPKEEWKS
      VNLNKVNRPG  ----------  ---RTPSKLL  ----------G  PPMPKE-WES
      TKWNKAKRHG  ESIKGKTES-  -SKNTRSKLL  NHHAWDYHYA  AQIPKDMWKS
       *   *                    *  ****                 *  * *

1583  QEKSPEKTAF  KKKDTI-LSLN  ACESNHAIAA  INEGQNKPEI  EVTWAKQGRT
      LEKSPKSTAL  RTKDIISLPLD  RHESNHSIAA  KNEGQAETQR  EAAWTKQGGP
      KEKSPEIISI  KQEDTI-LSLR  PHGNSHSIGA  -NEKQNWPQR  ETTWVKQGQT
      ****        *   *         ** *  ** *             *  ***

1633  ERLCSONPPY  LKRHQR
      GRLCAPKPPV  LRRHQR
      QRTCSQIPPV  LKRHQR
       *  *     * * *  * ****
```

Light chain activation peptide
                                                    IIa/Xa
Human 1649 EITRTTLQSDQEEIDYDDTISVEMKKEDFDIYDEDENQSPR
Pig        DISLPTFQPEEDKMDYDDIFSTETKGEDFDIYGEDENQDPR
Mouse      EL--SAFQSEQEATDYDDAITIET-IEDFDIYSEDIKQGPR
              *      *  ****   *    ****     * **

FIG. 1E

A3 domain

|  | | IXa | Xa | |
|---|---|---|---|---|

```
Human 1690 SFQKKTRHYF IAAVERLWDY GMSSSPHVLR NRAQSGSVPQ FKKVVFQEFT    FIG. 1F
Pig        SFQKRTRHYF IAAVEQLWDY GMSESPRALR NRAQNGEVPR FKKVVFREFA
Mouse      SVQQKTRHYF IAAVERLWDY GMSTS-HVLR NRYQSDNVPQ FKKVVFQEFT
           * *  ***** ***** ****  ***  *    **  ** *   **   ***** **

1740 DGSFTQPLYR GELNEHLGLL GPYIRAEVED NIMVTFRNQA SRPYSFYSSL
           DGSFTQPSYR GELNKHLGLL GPYIRAEVED NIMVTFKNQA SRPYSFYSSL
           DGSFSQPLYR GELNEHLGLL GPYIRAEVED NIMVTFKNQA SRPYSFYSSL
           ****  **  **  **** *****  ********** ****** *** **********
                                  Factor IXa binding
      1790 ISYEEDQRQG AEPRKNFVKP NETKTYFWKV QHHMAPTKDE FDCKAWAYFS
           ISYPDDQEQG AEPRHNFVQP NETRTYFWKV QHHMAPTEDE FDCKAWAYFS
           ISYKEDQR-G EEPRRNFVKP NETKIYFWKV QHHMAPTEDE FDCKAWAYFS
           ***   **   *   *** *  ***  ***** ********** **********

1840 DVDLEKDVHS GLIGPLLVCH TNTLNPAHGR QVTVQEFALF FTIFDETKSW
           DVDLEKDVHS GLIGPLLICR ANTLNAAHGR QVTVQEFALF FTIFDETKSW
           DVDLERDMHS GLIGPLLICH ANTLNPAHGR QVSVQEFALL FTIFDETKSW
           ***** * ** *******  *    **** **** ** ******  **********

1890 YFTENMERNC RAPCNIQMED PTFKENYRFH AINGYIMDTL PGLVMAQDQR
           YFTENVERNC RAPCHLQMED PTLKENYRFH AINGYVMDTL PGLVMAQNQR
           YFTENVKRNC KTPCNFQMED PTLKENYRFH AINGYVMDTL PGLVMAQDQR
           *****  *** *  **  **** ** ******* ********** ******  **

1940 IRWYLLSMGS NENIHSIHFS GHVFTVRKKE EYKMALYNLY PGVFETVEML
           IRWYLLSMGS NENIHSIHFS GHVFSVRKKE EYKMAVYNLY PGVFETVEML
           IRWYLLSMGN NENIQSIHFS GHVFTVRKKE EYKMAVYNLY PGVFETLEMI
           *********  ****  ***** **** ***** ***** **** ****** ** 
                                 Protein C binding
      1990 PSKAGIWRVE CLIGEHLHAG MSTLFLVYSN
           PSKVGIWRIE CLIGEHLQAG MSTTFLVYSK
           PSRAGIWRVE CLIGEHLQAG MSTLFLVYSK
           **  ****  *  *******  ** *** ******
```

```
C1 domain
Human 2020 KCQTPLGMAS GHIRDFQITA SGQYGQWAPK LARLHYSGSI NAWSTKEPFS    FIG. 1G
Pig        ECQAPLGMAS GRIRDFQITA SGQYGQWAPK LARLHYSGSI NAWSTKDPHS
Mouse      QCQIPLGMAS GSIRDFQITA SGHYGQWAPN LARLHYSGSI NAWSTKEPFS
           **  ****** * ******** ** ****** ********** ******  *  *

2070 WIKVDLLAPM IIHGIKTQGA RQKFSSLYIS QFIIMYSLDG KKWQTYRGNS
           WIKVDLLAPM IIHGIMTQGA RQKFSSLYIS QFIIMYSLDG RNWQSYRGNS
           WIKVDLLAPM IVHGIKTQGA RQKFSSLYIS QFIIMYSLDG KKWLSYQGNS
           ********** * *** **** ********** **********   *   * ***

2120 TGTLMVFFGN VDSSGIKHNI FNPPIIARYI RLHPTHYSIR STLRMELMGCDLN
           TGTLMVFFGN VDASGIKHNI FNPPIVARYI RLHPTHYSIR STLRMELMGCDLN
           TGTLMVFFGN VDSSGIKHNS FNPPIIARYI RLHPTHSSIR STLRMELMGCDLN
           ********** ** ******  ***** **** ****** *** *************

C2 domain                inhibitor epitope
Human 2173 SCSMPLGMES KAISDAQITA SSYFTNMFAT WSPSKARLHL QGRSNAWRPQ    FIG. 1H
Pig        SCSMPLGMQN KAISDSQITA SSHLSNIFAT WSPSQARLHL QGRTNAWRPR
Mouse      SCSIPLGMES KVISDTQITA SSYFTNMFAT WSPSQARLHL QGRTNAWRPQ
           *** ****   * *** ****  **   * *** **** ***** *** *****
                                        C2
      2223 VNNPKEWLQV DFQKTMKVTG VTTQGVKSLL TSMYVKEFLI SSSQDGHQWT
           VSSAEEWLQV DLQKTVKVTG ITTQGVKSLL SSMYVKEFLV SSSQDGRRHT
           VNDPKQWLQV DLQKTMKVTG IITQGVKSLF TSMFVKEFLI SSSQDGHHWT
           *          ****  *** ****  ******** **  ***** * *****  **
                                                      Phospholipid
      2273 LFFQNGKVKV FQGNQDSFTP VVNSLDPPLL TRYLRIHPQS WVHQIALRME
           LFLQDGHTKV FQGNQDSSTP VVNALDPPLF TRYLRIHPTS WAQHIALRLE
           QILYNGKVKV FQGNQDSSTP MMNSLDPPLL TRYLRIHPQI WEHQIALRLE
           *  ** ***********  *****  ******** *   *  *** *
           binding
      2323 VLGCEAQDLY
           VLGCEAQDLY
           ILGCEAQQQY
           ******  *
```

MODIFIED FACTOR VIII

CROSS REFERENCE TO RELATED APPLICATIONS

This application is a continuation-in-part of U.S. patent application Ser. No. 09/037,601 filed Mar. 10, 1998 now U.S. Pat. No. 6,180,371; which is a continuation-in-part of U.S. patent application Ser. No. 08/670,707 filed Jun. 26, 1996, which issued as U.S. Pat. No. 5,859,204, and is also a continuation-in-part of International Patent Application No. PCT/US97/11155 filed Jun. 26, 1997.

ACKNOWLEDGEMENT OF FEDERAL RESEARCH SUPPORT

The government has rights in this invention arising from National Institutes of Health Grant No. HL46215 that partially funded the research leading to this invention.

BACKGROUND OF THE INVENTION

Blood clotting begins when platelets adhere to the cut wall of an injured blood vessel at a lesion site. Subsequently, in a cascade of enzymatically regulated reactions, soluble fibrinogen molecules are converted by the enzyme thrombin to insoluble strands of fibrin that hold the platelets together in a thrombus. At each step in the cascade>a protein precursor is converted to a protease that cleaves the next protein precursor in the series. Cofactors are required at most of the steps.

Factor VIII circulates as an inactive precursor in blood, bound tightly and non-covalently to von Willebrand factor. Factor VIII is proteolytically activated by thrombin or factor Xa, which dissociates it from von Willebrand factor and activates its procoagulant function in the cascade. In its active form, the protein factor VIIIa is a cofactor that increases the catalytic efficiency of factor IXa toward factor X activation by several orders of magnitude.

People with deficiencies in factor VIII or antibodies against factor VIII who are not treated with factor VIII suffer uncontrolled internal bleeding that may cause a range of serious symptoms, from inflammatory reactions in joints to early death. Severe hemophiliacs, who number about 10,000 in the United States, can be treated with infusion of human factor VIII, which will restore the blood's normal clotting ability if administered with sufficient frequency and concentration. The classic definition of factor VIII, in fact, is that substance present in normal blood plasma that corrects the clotting defect in plasma derived from individuals with hemophilia A.

The development of antibodies ("inhibitors" or "inhibitory antibodies") that inhibit the activity of factor VIII is a serious complication in the management of patients with hemophilia. Autoantibodies develop in approximately 20% of patients with hemophilia A in response to therapeutic infusions of factor VIII. In previously untreated patients with hemophilia A who develop inhibitors, the inhibitor usually develops within one year of treatment. Additionally, autoantibodies that inactivate factor VIII occasionally develop in individuals with previously normal factor VIII levels. If the inhibitor titer is low enough, patients can be managed by increasing the dose of factor VIII. However, often the inhibitor titer is so high that it cannot be overwhelmed by factor VIII. An alternative strategy is to bypass the need for factor VIII during normal hemostasis using factor IX complex preparations (for example, KONYNE®, Proplex®) or recombinant human factor VIIa. Additionally, since porcine factor VIII usually has substantially less reactivity with inhibitors than human factor VIII, a partially purified porcine factor VIII preparation (HYATE:C®) has been used. Many patients who have developed inhibitory antibodies to human factor VIII have been successfully treated with porcine factor VIII and have tolerated such treatment for long periods of time. However, administration of porcine factor VIII is not a complete solution because inhibitors may develop to porcine factor VIII after one or more infusions in some patients.

Several preparations of human plasma-derived factor VIII of varying degrees of purity are available commercially for the treatment of hemophilia A. These include a partially-purified factor VIII derived from the pooled blood of many donors that is heat- and detergent-treated for viruses but contain a significant level of antigenic proteins; a monoclonal antibody-purified factor VIII that has lower levels of antigenic impurities and viral contamination; and recombinant human factor VIII, clinical trials for which are underway. Unfortunately, human factor VIII is unstable at physiologic concentrations and pH, is present in blood at an extremely low concentration (0.2 $\mu$g/ml plasma), and has low specific clotting activity. Public health concerns regarding the risk of viruses or other blood-borne contaminants have limited the usefulness of porcine factor VIII purified from porcine blood.

Hemophiliacs require daily replacement of factor VIII to prevent bleeding and the resulting deforming hemophilic arthropathy. However, supplies have been inadequate and problems in therapeutic use occur due to difficulty in isolation and purification, immunogenicity, and the necessity of removing the AIDS and hepatitis infectivity risk. The use of recombinant human factor VIII or partially-purified porcine factor VIII will not resolve all the problems.

The problems associated with the commonly used, commercially available, plasma-derived factor VIII have stimulated significant interest in the development of a better factor VIII product. There is a need for a more potent factor VIII molecule so that more units of clotting activity can be delivered per molecule; a factor VIII molecule that is stable at a selected pH and physiologic concentration; a factor VIII molecule that is less apt to cause production of inhibitory antibodies; and a factor VIII molecule that evades immune detection in patients who have already acquired antibodies to human factor VIII.

It is therefore an object of the present invention to provide a factor VIII that corrects hemophilia in a patient deficient in factor VIII or having inhibitors to human factor VIII.

It is a further object of the present invention to provide methods for treatment of hemophiliacs.

It is still another object of the present invention to provide a factor VIII that is stable at a selected pH and physiologic concentration.

It is yet another object of the present invention to provide a factor VIII that has greater coagulant activity than human factor VIII.

It is an additional object of the present invention to provide a factor VIII against which less antibody is produced.

It is a further object of the invention to provide a method for making recombinant porcine factor VIII and specifically modified porcine factor VIII.

SUMMARY OF THE INVENTION

The determination of the entire DNA sequence encoding porcine factor VIII set forth herein has enabled, for the first time, the synthesis of full-length porcine factor VIII by expressing the DNA encoding porcine factor VIII in a suitable host cell. Purified recombinant porcine factor VIII is therefore an aspect of the present invention. The DNA encoding each domain of porcine factor VIII as well as any specified fragment thereof, can be similarly expressed. Furthermore, porcine fVIII having all or part of the B domain deleted (B-domainless porcine fVIII) is made available as part of the present invention, by expression DNA encoding porcine fVIII having a deletion of one or more codons of the B-domain.

Also provided are pharmaceutical compositions and methods for treating patients having factor VIII deficiency comprising administering recombinant porcine factor VIII or a modified recombinant porcine factor VIII, in particular a B-domainless porcine factor VIII.

BRIEF DESCRIPTION OF THE DRAWINGS

FIGS. 1A–1H taken together provide an aligned sequence comparison of the human, pig and mouse factor VIII acid sequences.

DETAILED DESCRIPTION OF THE INVENTION

Unless otherwise specified or indicated, as used herein, "factor VIII" denotes any functional factor VIII protein molecule from any mammal.

As used herein, "mammalian factor VIII" includes factor VIII with amino acid sequence derived from any non-human mammal, unless otherwise specified. "Animal", as used herein, refers to pig and other non-human mammals.

A "fusion protein" or "fusion factor VIII or fragment thereof", as used herein, is the product of a hybrid gene in which the coding sequence for one protein is altered, for example, by joining part of it to the coding sequence for a second protein from a different gene in proper reading frame register such that uninterrupted transcription and translation of the joined segments can occur to produce a hybrid gene that encodes the fusion protein.

A "corresponding" nucleic acid or amino acid or sequence of either, as used herein, is one present at a site in a factor VIII molecule or fragment thereof that has the same structure and/or function as a site in the factor VIII molecule of another species, although the nucleic acid or amino acid number may not be identical. A DNA sequence "corresponding to" another factor VIII sequence substantially corresponds to such sequence, and hybridizes to the sequence of the designated SEQ ID NO. under stringent conditions. A DNA sequence "corresponding to" another factor VIII sequence also includes a sequence that results in the expression of a factor VIII or fragment thereof and would hybridize to the designated SEQ ID NO. but for the redundancy of the genetic code.

A "unique" amino acid residue or sequence, as used herein, refers to an amino acid sequence or residue in the factor VIII molecule of one species that is different from the homologous residue or sequence in the factor VIII molecule of another species.

"Specific activity," as used herein, refers to the activity that will correct the coagulation defect of human factor VIII deficient plasma. Specific activity is measured in units of clotting activity per milligram total factor VIII protein in a standard assay in which the clotting time of human factor VIII deficient plasma is compared to that of normal human plasma. One unit of factor VIII activity is the activity present in one milliliter of normal human plasma. In the assay, the shorter the time for clot formation, the greater the activity of the factor VIII being assayed. Porcine factor VIII has coagulation activity in a human factor VIII assay.

"Expression" refers to the set of processes that occur whereby genetic information is utilized to yield a product. A DNA encoding the amino acid sequence of porcine factor VIII can be "expressed" within a mammalian host cell to yield porcine factor VIII protein. The materials, genetic structures, host cells and conditions which permit expression of a given DNA sequence to occur are well-known in the art and can be manipulated to affect the time and amount of expression, as well as the intra- or extra-cellular location of the expressed protein. For example, by including DNA encoding a signal peptide at the 5' end of the DNA encoding porcine factor VIII (the 5' end being, by convention, that end encoding the $NH_2$ terminus of the protein) the expressed protein becomes exported from the interior of the host cell into the culture medium. Providing a signal peptide coding DNA in combination with the porcine factor VIII coding DNA is advantageous because the expressed factor VIII is exported into the culture medium which simplifies the process of purification. A preferred signal peptide is a mammalian factor VIII signal peptide.

The human factor VIII cDNA nucleotide and predicted amino acid sequences are shown in SEQ ID NOs:1 and 2, respectively. Factor VIII is synthesized as an approximately 300 kDa single chain protein with internal sequence homology that defines the "domain" sequence $NH_2$-A1-A2-B-A3-C1-C2-COOH. In a factor VIII molecule, a "domain", as used herein, is a continuous sequence of amino acids that is defined by internal amino acid sequence identity and sites of proteolytic cleavage by thrombin. Unless otherwise specified, factor VIII domains include the following amino acid residues, when the sequences are aligned with the human amino acid sequence (SEQ ID NO:2): A1, residues Ala1-Arg372; A2, residues Ser373-Arg740; B, residues Ser741-Arg1648; A3, residues Ser1690-Ile2032; C1, residues Arg2033-Asn2172; C2, residues Ser2173-Tyr2332. The A3-C1-C2 sequence includes residues Ser1690-Tyr2332. The remaining segment, residues Glu1649-Arg1689, is usually referred to as the factor VIII light chain activation peptide. Factor VIII is proteolytically activated by thrombin or factor Xa, which dissociates it from von Willebrand factor, forming factor VIIIa, which has procoagulant function. The biological function of factor VIIIa is to increase the catalytic efficiency of factor IXa toward factor X activation by several orders of magnitude. Thrombin-activated factor VIIIa is a 160 kDa A1/A2/A3-C1-C2 heterotrimer that forms a complex with factor IXa and factor X on the surface of platelets or monocytes. A "partial domain" as used herein is a continuous sequence of amino acids forming part of a domain.

"Subunits" of human or animal factor VIII, as used herein, are the heavy and light chains of the protein. The heavy chain of factor VIII contains three domains, A1, A2, and B. The light chain of factor VIII also contains three domains, A3, C1, and C2.

The terms "epitope," "antigenic site," and "antigenic determinant," as used herein, are used synonymously and are defined as a portion of the human, or animal factor VIII or fragment thereof that is specifically recognized by an antibody. It can consist of any number of amino acid residues, and it can be dependent upon the primary, secondary, or tertiary structure of the protein.

The term "immunogenic site," as used herein, is defined as a region of the human or animal factor VIII, or fragment thereof, that specifically elicits the production of antibody to the factor VIII, or fragment, in a human or animal, as measured by routine protocols, such as immunoassay, e.g. ELISA, or the Bethesda assay, described herein. It can consist of any number of amino acid residues, and it can be dependent upon the primary, secondary, or tertiary structure of the protein. In some embodiments, the hybrid or hybrid equivalent factor VIII or fragment thereof is nonimmunogenic or less immunogenic in an animal or human than human or porcine factor VIII.

"Factor VIII deficiency," as used herein, includes deficiency in clotting activity caused by production of defective factor VIII, by inadequate or no production of factor VIII, or by partial or total inhibition of factor VIII by inhibitors. Hemophilia A is a type of factor VIII deficiency resulting from a defect in an X-linked gene and the absence or deficiency of the factor VIII protein it encodes.

As used herein, "diagnostic assays" include assays that in some manner utilize the antigen-antibody interaction to detect and/or quantify the amount of a particular antibody that is present in a test sample to assist in the selection of medical therapies. There are many such assays known to those of skill in the art. As used herein, human, porcine or modified porcine factor VIII DNA or fragment thereof and protein expressed therefrom, in whole or in part, can be substituted for the corresponding reagents in the otherwise known assays, whereby the modified assays may be used to detect and/or quantify antibodies to factor VIII. It is the use of these reagents, the factor VIII DNA or fragment thereof or protein expressed therefrom, that permits modification of known assays for detection of antibodies to human or animal factor VIII. Such assays include, but are not limited to ELISAs, immunodiffusion assays, and immunoblots. Suitable methods for practicing any of these assays are known to those of skill in the art. As used herein, the factor VIII or fragment thereof that includes at least one epitope of the protein can be used as the diagnostic reagent. Examples of other assays in which human, porcine or modified porcine factor VIII or fragment thereof can be used include the Bethesda assay and anticoagulation assays.

The term "DNA encoding a protein, such as porcine factor VIII" means a polydeoxynucleic acid whose nucleotide sequence embodies coding information to a host cell for the amino acid sequence of the protein, e.g. porcine factor VIII, according to the known relationships of the genetic code.

The "expression product" of a DNA encoding a human or animal factor VIII or a modified factor VIII is the product obtained from expression of the referenced DNA in a suitable host cell, including such features of pre- or post-translational modification of protein encoded by the referenced DNA, including but not limited to glycosylation, proteolytic cleavage and the like. It is known in the art that such modifications can occur and can differ somewhat depending upon host cell type and other factors, and can result in molecular isoforms of the product, with retention of procoagulant activity. See, e.g. Lind, P. et al., *Eur. J. Biochem.* 232:1927 (1995), incorporated herein by reference.

An "expression vector" is a DNA element, often of circular structure, having the ability to replicate autonomously in a desired host cell, or to integrate into a host cell genome and also possessing certain well-known features which permit expression of a coding DNA inserted into the vector sequence at the proper site and in proper orientation. Such features can include, but are not limited to, one or more promoter sequences to direct transcription initiation of the coding DNA and other DNA elements such as enhancers, polyadenylation sites and the like, all as well known in the art. The term "expression vector" is used to denote both a vector having a DNA coding sequence to be expressed inserted within its sequence, and a vector having the requisite expression control elements so arranged with respect to an insertion site that it can serve to express any coding DNA inserted into the site, all as well-known in the art. Thus, for example, a vector lacking a promoter can become an expression vector by the insertion of a promoter combined with a coding DNA.

GENERAL DESCRIPTION OF METHODS

U.S. Pat. No. 5,364,771 described the discovery of hybrid human/porcine factor VIII molecules having coagulant activity, in which elements of the factor VIII molecule of human or pig are substituted for corresponding elements of the factor VIII molecule of the other species. U.S. Pat. No. 5,663,060 describes procoagulant hybrid human/animal and hybrid equivalent factor VIII molecules, in which elements of the factor VIII molecule of one species are substituted for corresponding elements of the factor VIII molecule of the other species.

Since current information indicates that the B domain has no inhibitory epitope and has no known effect on factor VIII function, in some embodiments the B domain is wholly or partially deleted in the active hybrid or hybrid equivalent factor VIII molecules or fragments thereof ("B(–) factor VIII") prepared by any of the methods described herein.

The human factor VIII gene was isolated and expressed in mammalian cells, as reported by Toole, J. J. et al. (1984) *Nature* 312:342–347 (Genetics Institute); Gitschier, J. et al.(1984) *Nature* 312:326–330 (Genentech); Wood, W. I. et al. (1984) *Nature* 312:330–337 (Genentech); Vehar, G. A. et al. (1984) *Nature* 312:337–342 (Genentech); WO 87/04187; WO 88/08035; WO 88/03558; U.S. Pat. No. 4,757,006, and the amino acid sequence was deduced from cDNA. U.S. Pat. No. 4,965,199 to Capon et al. discloses a recombinant DNA method for producing factor VIII in mammalian host cells and purification of human factor VIII. Human factor VIII expression on CHO (Chinese hamster ovary) cells and BHKC (baby hamster kidney cells) has been reported. Human factor VIII has been modified to delete part or all of the B domain (U.S. Pat. No. 4,868,112), and replacement of the human factor VIII B domain with the human factor V B domain has been attempted (U.S. Pat. No. 5,004,803). The cDNA sequence encoding human factor VIII and predicted amino acid sequence are shown in SEQ ID NOs:1 and 2, respectively. In SEQ ID NO:1, the coding region begins at nucleotide position 208, the triplet GCC being the codon for amino acid number 1 (Ala) of the mature protein as given in SEQ ID NO:2.

Porcine factor VIII has been isolated from plasma [Fass, D. N. et al. (1982) *Blood* 59:594]. Partial amino acid sequence of porcine factor VIII corresponding to portions of the N-terminal light chain sequence having homology to ceruloplasmin and coagulation factor V were described by Church et al. (1984) *Proc. Natl. Acad. Sci. USA* 81:6934. Toole, J. J. et al. (1984) *Nature* 312:342–347 described the partial sequencing of the N-terminal end of four amino acid fragments of porcine factor VIII but did not characterize the fragments as to their positions in the factor VIII molecule. The amino acid sequence of the B and part of the A2 domains of porcine factor VIII were reported by Toole, J. J. et al. (1986) *Proc. Natl. Acad. Sci, USA* 83:5939–5942. The cDNA sequence encoding the complete A2 domain of porcine factor VIII and predicted amino acid sequence and hybrid human/porcine factor VIII having substitutions of all domains, all subunits, and specific amino acid sequences were disclosed in U.S. Pat. No. 5,364,771 entitled "Hybrid Human/Porcine factor VIII" issued on Nov. 15, 1994, and in WO 93/20093 published Oct. 14, 1993. The cDNA sequence encoding the A2 domain of porcine factor VIII corresponding to residues 373–740 in mature human factor VIII, as shown in SEQ ID NO:1, and the predicted amino acid sequence are shown in SEQ ID NOs:3 and 4, respectively. More recently, the nucleotide and corresponding amino acid sequences of part of the A1 domain lacking the first 198 amino acid and of the A2 domain of porcine factor VIII were reported in WO 94/11503, published May 26, 1994. The entire nucleotide sequence encoding porcine factor VIII, including the complete A1 domain, activation peptide, A3, C1 and C2 domains, as well as the encoded amino acid sequence, was finally obtained by Lollar, as disclosed in U.S. Pat. No. 5,859,204, issued Jan. 12, 1999, and in WO 97/49725, published Dec. 31, 1997, both incorporated herein by reference.

Both porcine and human factor VIII are isolated from plasma as a two subunit protein. The subunits, known as the heavy chain and light chain, are held together by a non-covalent bond that requires calcium or other divalent metal ions. The heavy chain of factor VIII contains three domains, A1, A2, and B, which are linked covalently. The light chain of factor VIII also contains three domains, designated A3, C1, and C2. The B domain has no known biological function and can be removed, or partially removed from the molecule proteolytically or by recombinant DNA technology methods without significant alteration in any measurable parameter of factor VIII. Human recombinant factor VIII has a similar structure and function to plasma-derived factor VIII, though it is not glycosylated unless expressed in mammalian cells.

Both human and porcine activated factor VIII ("factor VIIIa") have three subunits due to cleavage of the heavy chain between the A1 and A2 domains. This structure is designated A1/A2/A3-C1-C2. Human factor VIIIa is not stable under the conditions that stabilize porcine factor VIIIa, presumably because of the weaker association of the A2 subunit of human factor VIIIa. Dissociation of the A2 subunit of human and porcine factor VIIIa is associated with loss of activity in the factor VIIIa molecule. Yakhyaev, A. et al. (1997) Blood 90:Suppl. 1, Abstract #126, reported binding of A2 domain by low density lipoprotein receptor-related protein, suggesting that cellular uptake of A2 mediated by such binding acts to down-regulate factor VIII activity.

Expression of "B-domainless factor VIII" is enhanced by including portions of the B-domain. The inclusion of those parts of the B domain designated "SQ" [Lind, P. et al. (1995) supra] was reported to result in favorable expression. "SQ" constructs lack all of the human B domain except for 5 amino acids of the B domain N-terminus and 9 amino acids of the B domain C-terminus.

The purified hybrid factor VIII or fragment thereof can be assayed for immunoreactivity and coagulation activity by standard assays including, for example, the plasma-free factor VIII assay, the one-stage clotting assay, and the enzyme-linked immunosorbent assay using purified recombinant human factor VIII as a standard.

Other vectors, including both plasmid and eukaryotic viral vectors, may be used to express a recombinant gene construct in eukaryotic cells depending on the preference and judgment of the skilled practitioner (see, for example, Sambrook et al., Chapter 16). Other vectors and expression systems, including bacterial, yeast, and insect cell systems, can be used but are not preferred due to differences in, or lack of, glycosylation.

Recombinant factor VIII protein can be expressed in a variety of cells commonly used for culture and recombinant mammalian protein expression. In particular, a number of rodent cell lines have been found to be especially useful hosts for expression of large proteins. Preferred cell lines, available from the American Type Culture Collection, Rockville, Md., include baby hamster kidney cells, and chinese hamster ovary (CHO) cells which are cultured using routine procedures and media.

The basis for the greater coagulant activity of porcine factor VIII appears to be the more rapid spontaneous dissociation of the human A2 subunit from human factor VIIIa than the porcine A2 subunit from porcine factor VIIIa. Dissociation of the A2 subunit leads to loss of activity, [Lollar, P. et al. (1990) *J. Biol. Chem.* 265:1688–1692; Lollar, P. et al. (1992) *J. Biol. Chem.* 267:23652–23657; Fay, P. J. et al. (1992) *J. Biol. Chem.* 267:13246–13250].

Factor VIII Molecules with Reduced Immunoreactivity:

Epitopes that are immunoreactive with antibodies that inhibit the coagulant activity of factor VIII ("inhibitors" or "inhibitory antibodies") have been characterized based on known structure-function relationships in factor VIII. Presumably, inhibitors could act by disrupting any of the macromolecular interactions associated with the domain structure of factor VIII or its associations with von Willebrand factor, thrombin, factor Xa, factor IXa, or factor X. However, most inhibitory antibodies to human factor VIII act by binding to epitopes located in the 40 kDa A2 domain or 20 kDa C2 domain of factor VIII, disrupting specific functions associated with these domains, as described by Fulcher et al. (1985) *Proc. Natl. Acad. Sci USA* 82:7728–7732; and Scandella et al. (1988) *Proc. Natl. Acad. Sci. USA* 85:6152–6156. In addition to the A2 and C2 epitopes, there may be a third epitope in the A3 or C1 domain of the light chain of factor VIII, according to Scandella et al. (1993) *Blood* 82:1767–1775. The significance of this putative third epitope is unknown, but it appears to account for a minor fraction of the epitope reactivity in factor VIII.

Anti-A2 antibodies block factor X activation, as shown by Lollar et al. (1994) *J. Clin. Invest.* 93:2497–2504. Previous mapping studies by deletion mutagenesis described by Ware et al. (1992) *Blood Coagul. Fibrinolysis* 3:703–716, located the A2 epitope to within a 20 kDa region of the $NH_2$-terminal end of the 40 kDa A2 domain. Competition immunoradiometric assays have indicated that A2 inhibitors recognize either a common epitope or narrowly clustered epitopes, as described by Scandella et al. (1992) *Throm. Haemostas* 67:665–671, and as demonstrated in U.S. Pat. No. 5,859,204.

Animal or modified animal factor VIII molecules can be tested in humans for their reduced antigenicity and/or immunogenicity in clinical trials. In one type of trial, designed to determine whether the factor VIII is immunoreactive with inhibitory antibodies, factor VIII is administered, preferably by intravenous infusion, to approximately 25 patients having factor VIII deficiency who have antibodies that inhibit the coagulant activity of therapeutic human factor VIII. The dosage of the animal or modified animal factor VIII is in a range between 5 and 50 Units/kg body weight, preferably 10–50 Units/kg, and most preferably 40 Units/kg body weight. Approximately 1 hour after each administration, the recovery of factor VIII from blood samples is measured in a one-stage coagulation assay. Samples are taken again approximately 5 hours after infusion, and recovery is measured. Total recovery and the rate of disappearance of factor VIII from the samples is predictive of the antibody titer and inhibitory activity. If the antibody titer is high, factor VIII recovery usually cannot be measured. The recovery results are compared to the recovery results in patients treated with plasma-derived human factor VIII, recombinant human factor VIII, plasma-derived porcine factor VIII, and other commonly used therapeutic forms of factor VIII or factor VIII substitutes.

After identification of clinically significant epitopes, recombinant factor VIII molecules can be expressed that have less than or equal cross-reactivity compared with plasma-derived porcine factor VIII when tested in vitro against a broad survey of inhibitor plasmas. Additional mutagenesis in epitopic regions can be done to reduce cross-reactivity. Reduced cross-reactivity, although desirable, is not necessary to produce a product that may have advantages over the existing plasma-derived porcine factor VIII concentrate, which can produce side effects due to contaminant porcine proteins or contaminant infectious agents such as viruses or prions. A recombinant porcine or modified porcine factor VIII molecule will not contain foreign porcine proteins.

Diagnostic Assays.

The factor VIII cDNA and/or protein expressed therefrom, in whole or in part, can be used in assays as diagnostic reagents for the detection of inhibitory antibodies to human or animal factor VIII or modified animal VIII in substrates, including, for example, samples of serum and body fluids of human patients with factor VIII deficiency. These antibody assays include assays such as ELISA assays, immunoblots, radioimmunoassays, immunodiffusion assays, and assay of factor VIII biological activity (e.g., by coagulation assay). Techniques for preparing these reagents and methods for use thereof are known to those skilled in the art. For example, an immunoassay for detection of inhibitory antibodies in a patient serum sample can include reacting the test sample with a sufficient amount of the factor VIII to be tested that a detectable complex can be formed with the inhibitory antibodies in the sample of the test factor VIII is indeed antigenic.

Nucleic acid and amino acid probes can be prepared based on the sequence of the hybrid factor VIII cDNA or protein molecule or fragments thereof. In some embodiments, these can be labeled using dyes or enzymatic, fluorescent, chemiluminescent, or radioactive labels that are commercially available. The amino acid probes can be used, for example, to screen sera or other body fluids where the presence of inhibitors to human, animal, or hybrid human/animal factor VIII is suspected. Levels of inhibitors can be quantitated in patients and compared to healthy controls, and can be used, for example, to determine whether a patient with a factor VIII deficiency can be treated with an animal or modified animal factor VIII. The cDNA probes can be used, for example, for research purposes in screening DNA libraries.

Pharmaceutical Compositions.

Pharmaceutical compositions containing recombinant porcine or modified porcine factor VIII, alone or in combination with appropriate pharmaceutical stabilization compounds, delivery vehicles, and/or carrier vehicles, are prepared according to known methods, as described in Remington's *Pharmaceutical Sciences* by E. W. Martin.

In one preferred embodiment, the preferred carriers or delivery vehicles for intravenous infusion are physiological saline or phosphate buffered saline.

In another preferred embodiment, suitable stabilization compounds, delivery vehicles, and carrier vehicles include but are not limited to other human or animal proteins such as albumin.

Phospholipid vesicles or liposomal suspensions are also preferred as pharmaceutically acceptable carriers or delivery vehicles. These can be prepared according to methods known to those skilled in the art and can contain, for example, phosphatidylserine/-phosphatidylcholine or other compositions of phospholipids or detergents that together impart a negative charge to the surface, since factor VIII binds to negatively charged phospholipid membranes. Liposomes may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the hybrid factor VIII is then introduced into the container. The container is then swirled by hand to free lipid material from the sides of the container and to disperse lipid aggregates, thereby forming the liposomal suspension.

The recombinant porcine or modified porcine factor VIII can be combined with other suitable stabilization compounds, delivery vehicles, and/or carrier vehicles, including vitamin K dependent clotting factors, tissue factor, and von Willebrand factor (vWf) or a fragment of vWf that contains the factor VIII binding site, and polysaccharides such as sucrose.

Recombinant porcine or modified porcine factor VIII can also be delivered by gene therapy in the same way that human factor VIII can be delivered, using delivery means such as retroviral vectors. This method consists of incorporation of the desired factor VIII construct cDNA into human cells that are transplanted directly into a factor VIII deficient patient or that are placed in an implantable device, permeable to the factor VIII molecules but impermeable to cells, that is then transplanted. The preferred method will be retroviral-mediated gene transfer. In this method, an exogenous gene (e.g., a factor VIII cDNA) is cloned into the genome of a modified retrovirus. The gene is inserted into the genome of the host cell by viral machinery where it will be expressed by the cell. The retroviral vector is modified so that it will not produce virus, preventing viral infection of the host. The general principles for this type of therapy are known to those skilled in the art and have been reviewed in the literature [e.g., Kohn, D. B. et al. (1989) *Transufusion* 29:812–820].

Porcine or modified porcine factor VIII can be stored bound to vWf to increase the half-life and shelf-life of the hybrid molecule. Additionally, lyophilization of factor VIII can improve the yields of active molecules in the presence of vWf. Current methods for storage of human and animal factor VIII used by commercial suppliers can be employed for storage of recombinant factor VIII. These methods include: (1) lyophilization of factor VIII in a partially-purified state (as a factor VIII "concentrate" that is infused without further purification); (2) immunoaffinity-purification of factor VIII by the Zimmerman method and lyophilization in the presence of albumin, which stabilizes the factor VIII; (3) lyophilization of recombinant factor VIII in the presence of albumin.

Additionally, porcine or modified porcine factor VIII has been found to be indefinitely stable at 4° C. in 0.6 M NaCl, 20 mM MES, and 5 mM $CaCl_2$ at pH 6.0 and also can be stored frozen in these buffers and thawed with minimal loss of activity.

Methods of Treatment.

Recombinant porcine or modified porcine factor VIII is used to treat uncontrolled bleeding due to factor VIII deficiency (e.g., intraarticular, intracranial, or gastrointestinal hemorrhage) in hemophiliacs with and without inhibitory antibodies and in patients with acquired factor VIII deficiency due to the development of inhibitory antibodies. The active materials are preferably administered intravenously.

Additionally, recombinant porcine or modified porcine factor VIII can be administered by transplant of cells genetically engineered to produce the protein by implantation of a device containing such cells, as described above.

In a preferred embodiment, pharmaceutical compositions of recombinant porcine or modified porcine factor VIII alone or in combination with stabilizers, delivery vehicles, and/or carriers are infused into patients intravenously according to the same procedure that is used for infusion of human or animal factor VIII.

The treatment dosages of recombinant porcine or modified porcine factor VIII composition that must be administered to a patient in need of such treatment will vary depending on the severity of the factor VIII deficiency. Generally, dosage level is adjusted in frequency, duration, and units in keeping with the severity and duration of each patient's bleeding episode. Accordingly, the factor VIII is included in a pharmaceutically acceptable carrier, delivery vehicle, or stabilizer in an amount sufficient to deliver to a patient a therapeutically effective amount of the protein to stop bleeding, as measured by standard clotting assays.

Factor VIII is classically defined as that substance present in normal blood plasma that corrects the clotting defect in plasma derived from individuals with hemophilia A. The coagulant activity in vitro of purified and partially-purified forms of factor VIII is used to calculate the dose of factor VIII for infusions in human patients and is a reliable indicator of activity recovered from patient plasma and of correction of the in vivo bleeding defect. There are no reported discrepancies between standard assay of novel factor VIII molecules in vitro and their behavior in the dog infusion model or in human patients, according to Lusher, J. M. et al. 328 *New Engl. J. Med.* 328:453–459; Pittman, D. D. et al. (1992) *Blood* 79:389–397; and Brinkhous et al. (1985) *Proc. Natl. Acad. Sci.* 82:8752–8755.

Usually, the desired plasma factor VIII activity level to be achieved in the patient through administration of the recombinant porcine or modified porcine factor VIII is in the range of 30–100% of normal. In a preferred mode of administration of the therapeutic factor VIII, the composition is given intravenously at a preferred dosage in the range from about 5 to 50 units/kg body weight, more preferably in a range of 10–50 units/kg body weight, and most preferably at a dosage of 20–40 units/kg body weight; the interval frequency is in the range from about 8 to 24 hours (in severely affected hemophiliacs); and the duration of treatment in days is in the range from 1 to 10 days or until the bleeding episode is resolved. See, e.g., Roberts, H. R., and M. R. Jones, "Hemophilia and Related Conditions—Congenital Deficiencies of Prothrombin (Factor II, Factor V, and Factors VII to XII)," Ch. 153, 1453–1474, 1460, in *Hematology*, Williams, W. J., et al., ed. (1990). Patients with inhibitors may require a different amount of recombinant porcine or modified porcine factor VIII than their previous form of factor VIII. For example, patients may require less recombinant porcine or modified porcine factor VIII because of its higher specific activity than human factor VIII and its decreased antibody reactivity. As in treatment with human or plasma-derived porcine factor VIII, the amount of therapeutic factor VIII infused is defined by the one-stage factor VIII coagulation assay and, in selected instances, in vivo recovery is determined by measuring the factor VIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition.

Treatment can take the form of a single intravenous administration of the composition or periodic or continuous administration over an extended period of time, as required. Alternatively, therapeutic factor VIII can be administered subcutaneously or orally with liposomes in one or several doses at varying intervals of time.

Recombinant porcine or modified porcine factor VIII can also be used to treat uncontrolled bleeding due to factor VIII deficiency in hemophiliacs who have developed antibodies to human factor VIII. In this case, coagulant activity that is superior to that of human or animal factor VIII alone is not necessary. Coagulant activity that is inferior to that of human factor VIII (i.e., less than 3,000 units/mg) will be useful if that activity is not neutralized by antibodies in the patient's plasma.

It has been demonstrated herein that recombinant porcine and modified porcine factor VIII's can differ in specific activity from human factor VIII. Factor VIII proteins having greater procoagulant activity from human factor VIII are useful in treatment of hemophilia because lower dosages will be required to correct a patient's factor VIII deficiency. Factor VIII's having lower procoagulant activity than human factor VIII are also suitable for therapeutic use provided they have at least 1% of specific activity compared to normal human factor VIII. A factor VIII of the present invention having procoagulant activity is therefore defined as having at least 1% of the specific activity of human factor VIII.

The recombinant porcine or modified porcine factor VIII molecule and the methods for isolation, characterization, making, and using it generally described above will be further understood with reference to the following non-limiting examples.

EXAMPLE 1

Assay of Porcine Factor VIII and Hybrid Human/porcine Factor VII

Porcine factor VIII has more coagulant activity than human factor VIII, based on specific activity of the molecule. This conclusion is based on the use of appropriate standard curves that allow human porcine factor VIII to be fairly compared. Coagulation assays are based on the ability of factor VIII to shorten the clotting time of plasma derived from a patient with hemophilia A. Two types of assays were employed: the one-stage and the two stage assay.

In the one-stage assay, 0.1 ml hemophilia A plasma (George King Biomedical, Inc.) was incubated with 0.1 ml activated partial thromboplastin reagent (APTT) (Organon Teknika) and 0.01 ml sample or standard, consisting of diluted, citrated normal human plasma, for 5 min at 37° C. in a water bath. Incubation was followed by addition of 0.1 ml 20 mM $CaCl_2$, and the time for development of a fibrin clot was determined by visual inspection.

A unit of factor VIII is defined as the amount present in 1 ml of citrated normal human plasma. With human plasma as the standard, porcine and human factor VIII activity were compared directly. Dilutions of the plasma standard or purified proteins were made into 0.15 M NaCl, 0.02 M HEPES, pH 7.4. The standard curve was constructed based on 3 or 4 dilutions of plasma, the highest dilution being 1/50, and on $\log_{10}$ clotting time plotted against $\log_{10}$ plasma concentration, which results in a linear plot. The units of factor VIII in an unknown sample were determined by interpolation from the standard curve.

The one-stage assay relies on endogenous activation of factor-VIII by activators formed in the hemophilia A plasma, whereas the two-stage assay measures the procoagulant activity of preactivated factor VIII. In the two-stage assay, samples containing factor VIII that had been reacted with thrombin were added to a mixture of activated partial thromboplastin and human hemophilia A plasma that had been preincubated for 5 min at 37° C. The resulting clotting times were then converted to units/ml, based on the same human standard curve described above. The relative activity in the two-stage assay was higher than in the one-stage assay because the factor VIII had been preactivated.

EXAMPLE 2

Characterization of the Functional Difference Between Human and Porcine Factor VII The isolation of porcine and human plasma-derived factor VIII and human recombinant factor VIII have been described in the literature in Fulcher, C. A. et al. (1982) *Proc. Natl. Acad. Sci. USA* 79:1648–1652; Toole et al. (1984) *Nature* 312:342–347 (Genetics Institute); Gitschier et al. (1984) *Nature* 312:326–330 (Genentech); Wood et al. (1984) *Nature* 312:330–337 (Genentech); Vehar et al. 312 *Nature* 312:337–342 (Genentech); Fass et al. (1982) *Blood* 59:594; Toole et al. (1986) *Proc. Natl. Acad. Sci. USA* 83:5939–5942. This can be accomplished in several ways. All these preparations are similar in subunit composition, although there is a functional difference in stability between human and porcine factor VIII.

For comparison of human recombinant and porcine factor VIII, preparations of highly-purified human recombinant factor VIII (Cutter Laboratories, Berkeley, Calif.) and porcine factor VIII [immunopurified as described in Fass et al. (1982) *Blood* 59:594] were subjected to high-pressure liquid chromatography (HPLC) over a Mono Q™ (Pharmacia-LKB, Piscataway, N.J.) anion-exchange column (Pharmacia, Inc.). The purposes of the Mono Q™ HPLC step were elimination of minor impurities of exchange of human and porcine factor VIII into a common buffer for comparative purposes. Vials containing 1000–2000 units of factor VIII were reconstituted with 5 ml $H_2O$. Hepes (2 M at pH 7.4) was then added to a final concentration of 0.02 M. Factor VIII was applied to a Mono Q™ HR 5/5 column equilibrated in 0.15 M NaCl, 0.02 M Hepes, 5mM $CaCl_2$, at pH 7.4 (Buffer A plus 0.15 M NaCl); washed with 10 ml Buffer A+0.15 M NaCl; and eluted with a 20 ml linear gradient, 0.15 M to 0.90 M NaCl in Buffer A at a flow rate of 1 ml/min.

For comparison of human plasma-derived factor VIII (purified by Mono Q™ HPLC) and porcine factor VIII, immunoaffinity-purified, plasma-derived porcine factor VIII was diluted 1:4 with 0.04 M Hepes, 5 mM $CaCl_2$, 0.01% Tween-80, at pH 7.4, and subjected to Mono Q™ HPLC under the same conditions described in the previous paragraph for human factor VIII. These procedures for the isolation of human and porcine factor VIII are standard for those skilled in the art.

Column fractions were assayed for factor VIII activity by a one-stage coagulation assay. The average results of the assays, expressed in units of activity per $A_{280}$ of material, are given in Table II, and indicate that porcine factor VIII has at least six times greater activity than human factor VIII when the one-stage assay is used.

TABLE II

COMPARISON OF HUMAN AND PORCINE FACTOR VIII COAGULANT ACTIVITY

|  | Activity (U/$A_{280}$) |
| --- | --- |
| Porcine | 21,300 |
| Human plasma-derived | 3,600 |
| Human recombinant | 2,400 |

EXAMPLE 3

Comparison of the Stability of Human and Porcine Factor VIII

The results of the one-stage assay for factor VIII reflect activation of factor VIII to factor VIIIa in the sample and possibly loss of formed factor VIIIa activity. A direct comparison of the stability of human and porcine factor VIII was made. Samples from Mono Q™ HPLC (Pharmacia, Inc., Piscataway, N.J.) were diluted to the same concentration and buffer composition and reacted with thrombin. At various times, samples were removed for two-stage coagulation assay. Typically, peak activity (at 2 min) was 10-fold greater for porcine than human factor VIIIa, and the activities of both porcine and human factor VIIIa subsequently decreased, with human factor VIIIa activity decreasing more rapidly.

Generally, attempts to isolate stable human factor VIIIa are not successful even when conditions that produce stable porcine factor VIIIa are used. To demonstrate this, Mono QT HPLC-purified human factor VIII was activated with thrombin and subjected to Mono S™ cation-exchange (Pharmacia, Inc.) HPLC under conditions that produce stable porcine factor VIIIa, as described by Lollar et al. (1989) *Biochemistry* 28:666.

Human factor VIII, 43 μg/ml (0.2 μM) in 0.2 M NaCl, 0.01 M Hepes, 2.5 mM $CaCl_2$, at pH 7.4, in 10 ml total volume, was reacted with thrombin (0.036 μM) for 10 min, at which time FPR-$CH_2Cl$ D-phenyl-prolyl-arginyl-chloromethyl ketone was added to a concentration of 0.2 μM for irreversible inactivation of thrombin. The mixture then was diluted 1:1 with 40 mM 2-(N-morpholino) ethane sulfonic acid (MES), 5 mM $CaCl_2$, at pH 6.0, and loaded at 2 ml/min onto a Mono S™ HR 5/5 HPLC column (Pharmacia, Inc.) equilibrated in 5 mM MES, 5 mM $CaCl_2$, at pH 6.0 (Buffer B) plus 0.1 M NaCl. Factor VIIIa was eluted without column washing with a 20 ml gradient from 0.1 M NaCl to 0.9 M NaCl in Buffer B at 1 ml/min.

The fraction with coagulant activity in the two-stage assay eluted as a single peak under these conditions. The specific activity of the peak fraction was approximately 7,500 U/$A_{280}$. Sodium dodecyl sulfate-polyacrylamide gel electrophoresis (SDS-PAGE) of the Mono S™ factor VIIIa peak, followed by silver staining of the protein, revealed two bands corresponding to a heterodimeric (A3-C1-C2/A1) derivative of factor VIII. Although the A2 fragment was not identified by silver staining under these conditions because of its low concentration, it was identified as a trace constituent by $^{125}$I-labeling.

In contrast to the results with human factor VIII, porcine factor VIIIa isolated by Mono S™ HPLC under the same conditions had a specific activity $1.6 \times 10^6$ U/A$_{280}$. Analysis of porcine factor VIIIa by SDS-PAGE revealed 3 fragments corresponding to A1, A2, and A3-C1-C2 subunits, demonstrating that porcine factor VIIIa possesses three subunits.

The results of Mono S™ HPLC of human thrombin-activated factor VIII preparations at pH 6.0 indicate that human factor VIIIa is labile under conditions that yield stable porcine factor VIIIa. However, although trace amounts of A2 fragment were identified in the peak fraction, determination of whether the coagulant activity resulted from small amounts of heterotrimeric factor VIIIa or from heterodimeric factor VIIIa that has a low specific activity was not possible from this method alone.

A way to isolate human factor VIIIa before it loses its A2 subunit is desirable to resolve this question. To this end, isolation was accomplished in a procedure that involves reduction of the pH of the Mono S™ buffers to pH 5. Mono Q™-purified human factor VIII (0.5 mg) was diluted with H$_2$O to give a final composition of 0.25 mg/ml (1 μm) factor VIII in 0.25 M NaCl, 0.01 M Hepes, 2.5 mM CaCl$_2$, 0.005% Tween-80, at pH 7.4 (total volume 7.0 ml). Thrombin was added to a final concentration of 0.072 μm and allowed to react for 3 min. Thrombin was then inactivated with FPR-CH$_2$Cl (0.2 μm). The mixture then was diluted 1:1 with 40 mM sodium acetate, 5 mM CaCl$_2$, 0.01% Tween-80, at pH 5.0, and loaded at 2 ml/min onto a Mono S™ HR 5/5 HPLC column equilibrated in 0.01 M sodium acetate, 5 mM CaCl$_2$, 0.01% Tween-80, at pH 5.0, plus 0.1 M NaCl. Factor VIIIa was eluted without column washing with a 20 ml gradient from 0.1 M NaCl to 1.0 M NaCl in the same buffer at 1 ml/min. This resulted in recovery of coagulant activity in a peak that contained detectable amounts of the A2 fragment as shown by SDS-PAGE and silver staining. The specific activity of the peak fraction was tenfold greater than that recovered at pH 6.0 (75,000 U/A$_{280}$ v. 7,500 U/A$_{280}$). However, in contrast to porcine factor VIIIa isolated at pH 6.0, which is indefinitely stable at 4° C., human factor VIIIa activity decreased steadily over a period of several hours after elution from Mono S™. Additionally, the specific activity of factor VIIIa purified at pH 5.0 and assayed immediately is only 5% that of porcine factor VIIIa, indicating that substantial dissociation occurred prior to assay.

These results demonstrate that both human and porcine factor VIIIa are composed of three subunits (A1, A2, and A3-C1-C2). Dissociation of the A2 subunit is responsible for the loss of activity of both human and porcine factor VIIIa under certain conditions, such as physiological ionic strength, pH, and concentration. The relative stability of porcine factor VIIIa under certain conditions is because of stronger association of the A2 subunit.

EXAMPLE 4

Isolation and Sequencing of DNA Encoding the A2 Domain of Porcine Factor VIII

Only the nucleotide sequence encoding the B domain and part of the A2 domain of porcine factor VIII has been sequenced previously [Toole et al. (1986) Proc. Natl. Acad. Sci. USA 83:5939–5942]. The cDNA and predicted amino acid sequences (SEQ ID NOs: 3 and 4, respectively) for the entire porcine factor VIII A2 domain are disclosed herein.

The porcine factor VIII A2 domain was cloned by reverse transcription of porcine spleen total RNA and PCR amplification; degenerate primers based on the known human factor VIII cDNA sequence and an exact porcine primer based on a part of the porcine factor VIII sequence were used. A 1 kb PCR product was isolated and amplified by insertion into a Bluescript™ (Stratagene) phagemid vector.

The porcine A2 domain was completely sequenced by dideoxy sequencing. The cDNA and predicted amino acid sequences are as described in SEQ ID NOs: 3 and 4, respectively.

EXAMPLE 5

Complete Sequence of DNA Encoding Porcine Factor VIII

Klenow fragment, phosphorylated ClaI linkers, NotI linkers, T4 ligase, and Taq DNA polymerase were purchased from Promega (Madison, Wis.). Polynucleotide kinase was purchased from Life Technologies, Inc., Gaithersburg, Md. $\gamma^{32}$P-ATP (Redivue, >5000Ci/mmol) was purchased from Amersham. pBluescript II KS- and E. coli Epicurean XL1-Blue cells were purchased from Stratagene (La Jolla, Calif.). Synthetic oligonucleotides were purchased from Life Technologies, Inc. or Cruachem, Inc. 5'-phosphorylated primers were used when PCR products were produced for cloning purposes. Nucleotide (nt) numbering of oligonucleotides used as primers for polymerase chain reaction (PCR) amplification of porcine fVIII cDNA or genomic DNA uses the human fVIII cDNA as reference (Wood et al. (1984) supra).

Porcine spleen total RNA was isolated by acid guanidinium thiocyanate-phenol-chloroform extraction [Chomczynski et al. (1987) Anal. Biochem. 162:156–159]. Porcine cDNA was prepared from total spleen RNA using Moloney murine leukemia virus reverse transcriptase (RT) and random hexamers to prime the reaction (First-Strand cDNA Synthesis Kit, Pharmacia Biotech) unless otherwise indicated. RT reactions contained 45 mM Tris-Cl, pH 8.3, 68 mM KCl, 15 mM DTT, 9 mM MgCl$_2$, 0.08 mg/ml bovine serum albumin and 1.8 mM deoxynucleotide triphosphate (dNTP). Porcine genomic DNA was isolated from spleen using a standard procedure (Strauss, W. M. (1995) In Current Protocols in Molecular Biology, F. M. Ausubel et al., editors, John Wiley & Sons, pp. 2.2.1–2.2.3). Isolation of DNA from agarose gels was done using Geneclean II (Bio 101) or Quiex II Gel Extraction Kit (Qiagen).

PCR reactions were done using a Hybaid OmniGene thermocycler. For PCR reactions employing Taq DNA polymerase, reactions included 0.6 mM MgCl$_2$, 0.2 mM dNTPs, 0.5 μM oligonucleotide primers, 50 U/ml polymerase and 0.1 volume of first strand cDNA reaction mix. Except where indicated otherwise, PCR products were gel purified, blunt-ended with Klenow fragment, precipitated with ethanol, and either ligated to the EcoRV site of dephosphorylated pBluescript II KS- or ligated with phosphorylated ClaI linkers using T4 ligase, digested with ClaI, purified by Sephacryl S400 chromatography, and ligated to ClaI-cut, dephosphorylated pBluescript II KS-. Ligations were done using T4 DNA ligase (Rapid DNA ligation kit, Boehringer Mannheim) except where indicated otherwise. Insert-containing pBluescript II KS- plasmids were used to transform E. coli Epicurean XL1-Blue cells.

Sequencing of plasmid DNA was done using an Applied Biosystems 373a automated DNA sequencer and the PRISM dye terminator kit or manually using Sequenase v. 2.0 sequencing kit (Amersham Corporation). Direct sequencing of PCR products, including $^{32}$P-end labelling of oligonucleotides was done using a cycle sequencing protocol (dsDNA Cycle Sequencing System, Life Technologies).

Isolation of Porcine fVIII cDNA Clones Containing 5' UTR Sequence, Signal peptide and A1 Domain Codons.

The porcine fVIII cDNA 5' to the A2 domain was amplified by nested RT-PCR of female pig spleen total RNA using a 5' rapid amplification of cDNA ends (5'-RACE) protocol (Marathon cDNA Amplification, Clontech, Version PR55453). This included first strand cDNA synthesis using a lock-docking oligo(dT) primer [Borson, N. D. et al. (1992) *PCR Methods Appl.* 2:144–148], second strand cDNA synthesis using *E. coli* DNA polymerase I, and ligation with a 5' extended double stranded adaptor, SEQ ID NO:5

5'-CTA ATA CGA CTC ACT ATA GGG CTC GAG CGG CCG CCC GGG CAG GT-3 3'-H$_2$N-CCCGTCCA-PO$_4$-5' whose short strand was blocked at the 3' end with an amino group to reduce non-specific PCR priming and which was complementary to the 8 nucleotides at the 3' end (Siebert, P. D., et al. (1995) *Nucleic. Acids. Res.* 23:1087–1088). The first round of PCR was done using an adaptor-specific oligonucleotide, SEQ ID NO:6 5'-CCA TCC TAA TAC GAC TCA CTA TAG GGC-3' (designated AP1) as sense primer, and a porcine fVIII A2 domain specific oligonucleotide SEQ ID NO:7 5'-CCA TTG ACA TGA AGA CCG TTT CTC-3' (nt 2081–2104) as antisense primer. The second round of PCR was done using a nested, adaptor-specific oligonucleotide, SEQ ID NO:8 5'-ACT CAC TAT AGG GCT CGA GCG GC-3' (designated AP2) as sense primer, and a nested, porcine A2 domain-specific oligonucleotide SEQ ID NO:9 5'-GGG TGC AAA GCG CTG ACA TCA GTG-3' (nt 1497–1520) as antisense primer. PCR was carried out using a commercial kit (Advantage cDNA PCR core kit) which employs an antibody-mediated hot start protocol [Kellogg, D. E. et al. (1994) *BioTechniques* 16:1134–1137]. PCR conditions included denaturation at 94° C. for 60 sec, followed by 30 cycles (first PCR) or 25 cycles (second PCR) of denaturation for 30 sec at 94° C., annealing for 30 sec at 60° C. and elongation for 4 min at 68using tube temperature control. This procedure yielded a prominent ≈1.6 kb product which was consistent with amplification of a fragment extending approximately 150 bp into the 5' UTR. The PCR product was cloned into pBluescript using ClaI linkers. The inserts of four clones were sequenced in both directions.

The sequence of these clones included regions corresponding to 137 bp of the 5' UTR, the signal peptide, the A1 domain and part of the A2 domain. A consensus was reached in at least 3 of 4 sites. However, the clones contained an average of 4 apparent PCR-generated mutations, presumably due to the multiple rounds of PCR required to generate a clonable product. Therefore, we used sequence obtained from the signal peptide region to design a sense strand phosphorylated PCR primer, SEQ ID NO: 10 5'-CCT CTC GAG CCA CCA TGT CGA GCC ACC ATG CAG CTA GAG CTC TCC ACC TG-3', designated RENEOPIGSP, for synthesis of another PCR product to confirm the sequence and for cloning into an expression vector. The sequence in bold represents the start codon. The sequence 5' to this represents sequence identical to that 5' of the insertion site into the mammalian expression vector ReNeo used for expression of fVIII (Lubin et al. (1994) supra). This site includes an XhoI cleavage site (underlined). RENEOPIGSP and the nt 1497–1520 oligonucleotide were used to prime a Taq DNA polymerase-mediated PCR reaction using porcine female spleen cDNA as a template. DNA polymerases from several other manufacturers failed to yield a detectable product. PCR conditions included denaturation at 94° C. for four min, followed by 35 cycles of denaturation for 1 min at 94° C., annealing for 2 min at 55° C. and elongation for 2 min at 72° C., followed by a final elongation step for 5 min at 72° C The PCR product was cloned into pBluescript using ClaI linkers. The inserts of two of these clones were sequenced in both directions and matched the consensus sequence.

Isolation of Porcine fVIII cDNA Clones Containing A3. C1 and 5' Half of the C2 Domain Codons.

Initially, two porcine spleen RT-PCR products, corresponding to a B-A3 domain fragment (nt 4519–5571) and a C1-C2 domain fragment (nt 6405–6990) were cloned. The 3'end of the C2 domain that was obtained extended into the exon 26 region, which is the terminal exon in fVIII. The B-A3 product was made using the porcine-specific B domain primer, SEQ ID NO: 11 5' CGC GCG GCC GCG CAT CTG <u>GCA AAG CTG AGT T</u>3', where the underlined region corresponds to a region in porcine fVIII that aligns with nt 4519–4530 in human fVIII. The 5' region of the oligonucleotide includes a NotI site that was originally intended for cloning purposes. The antisense primer used in generating the B-A3 product, SEQ ID NO: 12 5'-GAA ATA AGC CCA GGC TTT GCA GTC RAA-3' was based on the reverse complement of the human fVIII cDNA sequence at nt 5545–5571. The PCR reaction contained 50 mM KCl, 10 mM Tris-Cl, pH 9.0, 0.1% Triton X-100, 1.5 mM MgCl$_2$, 2.5 mM dNTPs, 20 μM primers, 25 units/ml Taq DNA polymerase and 1/20 volume of RT reaction mix. PCR conditions were denaturation at 94° C. for 3 min, followed by 30 cycles of denaturation for 1 min at 94° C., annealing for 2 min at 50° C. elongation for 2 min at 72° C. The PCR products were phosphorylated using T4 DNA kinase and NotI linkers were added. After cutting with NotI, the PCR fragments were cloned into the NotI site of BlueScript II KS- and transformed into XL1-Blue cells.

The C1-C2 product was made using the known human cDNA sequence to synthesize sense and antisense primers, SEQ ID NO: 13 5'-AGG AAA TTC CAC TGG AAC CTT N-3' (nt 6405–6426) and SEQ ID NO:14 5'-CTG GGG GTG AAT TCG AAG GTA GCG N-3' (reverse complement of nt 6966–6990), respectively. PCR conditions were identical to those used to generate the B-A2 product. The resulting fragment was ligated to the pNOT cloning vector using the Prime PCR Cloner Cloning System (5 Prime-3 Prime, Inc., Boulder, Colo.) and grown in JM109 cells.

The B-A3 and C 1-C2 plasmids were partially sequenced to make the porcine-specific sense and antisense oligonucleotides, SEQ ID NO:15 5'-GAG TTC ATC GGG AAG ACC TGT TG-3' (nt 4551–4573) and SEQ ID NO:16 5'-ACA GCC CAT CAA CTC CAT GCG AAG-3' (nt 6541–6564), respectively. These oligonucleotides were used as primers to generate a 2013 bp RT-PCR product using a Clontech Advantage cDNA PCR kit. This product, which corresponds to human nt 4551–6564, includes the region corresponding to the light chain activation peptide (nt 5002–5124), A3 domain (nt 5125–6114) and most of the C1 domain (nt 6115–6573); The sequence of the C1-C2 clone had established that human and porcine cDNAs from nt 6565 to the 3' end of the C1 domain were identical. The PCR product cloned into the EcoRV site of pBluescript II KS-. Four clones were completely sequenced in both directions. A consensus was reached in at least 3 of 4 sites.

Isolation of Porcine fVIII cDNA Clones Containing the 3' Half of the C2 Domain Codons.

The C2 domain of human fVIII (nucleotides 6574–7053) is contained within exons 24–26 [Gitschier J. et al. (1984) *Nature* 312:326–330]. Human exon 26 contains 1958 bp, corresponding nucleotides 6901–8858. It includes 1478 bp of 3' untranslated sequence. Attempts to clone the exon 26 cDNA corresponding to the 3' end of the C2 domain and the 3 'UTR by 3' RACE [Siebert et al. (1995) supra], inverse PCR [Ochman, H. et al. (1990) Biotechnology (N.Y). 8:759–760], restriction site PCR [Sarkar, G. et al. (1993) PCR Meth. Appl. 2:318–322], "unpredictably primed" PCR [Dominguez, O. et al. (1994) Nucleic. Acids Res. 22:3247–3248]:and by screening a porcine liver cDNA library failed. 3' RACE was attempted using the same adaptor-ligated double stranded cDNA library that was used to successfully used to clone the 5' end of the porcine fVIII cDNA. Thus, the failure of this method was not due to the absence of cDNA corresponding to exon 26.

A targeted gene walking PCR procedure [Parker, J. D. et al. (1991) Nucleic. Acids. Res. 19:3055–3060] was used to clone the 3' half of the C2 domain. A porcine-specific sense primer, SEQ ID NO: 17 5'-TCAGGGCAATCAGGACTCC-3' (nt 6904–6924) was synthesized based on the initial C2 domain sequence and was used in a PCR reaction with nonspecific "walking" primers selected from oligonucleotides available in the laboratory. The PCR products were then targeted by primer extension analysis [Parker et al. (1991) BioTechniques 10:94–101] using a $^{32}$p-end labelled porcine-specific internal primer, SEQ ID NO:18 5'-CCGTGGTGAACGCTCTGGACC-3' (nt 6932–6952). Interestingly, of the 40 nonspecific primers tested, only two yielded positive products on primer extension analysis and these two corresponded to an exact and a degenerate human sequence at the 3' end of the C2 domain: SEQ ID NO:19 5'-GTAGAGGTCCTGTGCCTCGCAGCC-3' (nt 7030–7053) and SEQ ID NO:20 5'-GTAGAGSTSCTGKGCCTCRCAKCCYAG-3', (nt 7027–7053). These primers had initially been designed to yield a product by conventional RT-PCR but failed to yield sufficient product that could be visualized by ethidium bromide dye binding. However, a PCR product could be identified by the more sensitive primer extension method. This product was gel-purified and directly sequenced. This extended the sequence of porcine fVIII 3' to nt 7026.

Additional sequence was obtained by primer extension analysis of a nested PCR product generated using the adaptor-ligated double-stranded cDNA library used in the 5'-RACE protocol described previously. The first round reaction used the porcine exact primer SEQ ID NO:21 5'-CTTCGCATGGAGTTGATGGGCTGT-3' (nt 6541–6564) and the AP1 primer. The second round reaction used SEQ ID NO:22 5'-AATCAGGACTCCTCCACCCCCG-3' (nt 6913–6934) and the AP2 primer. Direct PCR sequencing extended the sequence 3' to the end of the C2 domain (nt 7053). The C2 domain sequence was unique except at nt 7045 near the 3' end of the C2 domain. Analysis of repeated PCR reactions yielded either A, G or a double read of A/G at this site.

Sequencing was extended into the 3'UTR using two additional primers, SEQ ID NO:23 5'-GGA TCC ACC CCA CGA GCT GG-3' (nt 6977–6996) and SEQ ID NO:24 5'-CGC CCT GAG GCT CGA GGT TCT AGG-3' (nt 7008–7031). Approximately 15 bp of 3' UTR sequence were obtained, although the sequence was unclear at several sites. Several antisense primers then were synthesized based on the best estimates of the 3' untranslated sequence. These primers included the reverse complement of the TGA stop codon at their 3' termini. PCR products were obtained from both porcine spleen genomic DNA and porcine spleen cDNA that were visualized by agarose gel electrophoresis and ethidium bromide staining using a specific sense primer SEQ ID NO:25 5'-AAT CAG GAC TCC TCC ACC CCC G-3' (nt 6913–6934) and the 3' UTR antisense primer, SEQ ID NO:26 5'-CCTTGCAGGAATTCGATTCA-3'. To obtain sufficient quantities of material for cloning purposes, a second round of PCR was done using a nested sense primer, SEQ ID NO:27 5'-CCGTGGTGAACGCTCTGGACC-3' (nt 6932–6952) and the same antisense primer. The 141 bp PCR product was cloned into EcoRV-cut pBluescript II KS-. Sequence of three clones derived from genomic DNA and three clones derived from cDNA was obtained in both directions. The sequence was unambiguous except at nt 7045, where genomic DNA was always A and cDNA was always G.

Multiple DNA Sequence Alignments of Human, Porcine, and Mouse fVIII (FIGS. 1A–1H).

Alignments of the signal peptide, A1, A2, A3, C1, and C2 regions were done using the CLUSTALW program [Thompson, J. D. et al. (1994) Nucleic. Acids. Res. 22:4673–4680]. Gap open and gap extension penalties were 10 and 0.05 respectively. The alignments of the human, mouse, and pig B domains have been described previously [Elder et al. (1993) supra]. The human A2 sequence corresponds to amino acids 373–740 in SEQ ID NO:2. The porcine A2 amino acid sequence is given in SEQ ID NO:4, and the mouse A2 domain amino acid sequence is given in SEQ ID NO:28, amino acids 392–759.

EXAMPLE 6

Expression of Active, Recombinant B-domainless Porcine Factor VIII (PB⁻)

Materials

Citrated hemophilia A and normal pooled human plasmas were purchased from George King Biomedical, Inc. Fetal bovine serum, geneticin, penicillin, streptomycin, DMEM/F12 medium and AIM-V medium were purchased from Life Technologies, Inc. Taq DNA polymerase was purchased from Promega. Vent DNA polymerase was purchased from New England Biolabs. Pfu DNA polymerase and the phagemid pBlueScript II KS⁻ were purchased from Stratagene. Synthetic oligonucleotides were purchased from Life Technologies or Cruachem, Inc. Restriction enzymes were purchased from New England Biolabs or Promega. 5'-phosphorylated primers were used when PCR products were produced for cloning purposes. Nucleotide (nt) numbering of oligonucleotides used as primers for polymerase chain reaction (PCR) amplification of porcine fVIII cDNA or genomic DNA uses the human fVIII cDNA as reference [Wood et al. (1984) Nature 312:330–337]. A fVIII expression vector, designated HB⁻/ReNeo, was obtained from Biogen, Inc. HB⁻/ReNeo contains ampicillin and geneticin resistance genes and a human fVIII cDNA that lacks the entire B domain, defined as the Ser741-Arg1648 cleavage fragment produced by thrombin. To simplify mutagenesis of fVIII C2 domain cDNA, which is at the 3' end of the fVIII insert in ReNeo, a NotI site was introduced two bases 3' to the stop codon of HB⁻/ReNeo by splicing-by-overlap extension (SOE) mutagenesis [Horton, R. M. et al. (1993) Methods Enzymol. 217:270–279]. This construct is designated HB⁻ReNeo/NotI.

Total RNA was isolated by acid guanidinium thiocyanate-phenol-chloroform extraction [Chomczynski, P. et al. (1987) Anal. Biochem. 162:156–159]. cDNA was synthesized from mRNA using Moloney murine leukemia virus reverse transcriptase (RT) and random hexamers according to instructions supplied by the manufacturer (First-Strand cDNA Synthesis Kit, Pharmacia Biotech). Plasmid DNA was purified using a Qiagen Plasmid Maxi Kit (Qiagen, Inc.). PCR reactions were done using a Hybaid OmniGene thermocycler using Taq, Vent, or pfu DNA polymerases. PCR products were gel purified, precipitated with ethanol, and ligated into plasmid DNA using T4 DNA ligase (Rapid DNA ligation kit, Boehringer Mannheim). Insert-containing plasmids were used to transform E. coli Epicurean XL1-Blue cells. All novel fVIII DNA sequences generated by PCR were confirmed by dideoxy sequencing using an Applied Biosystems 373a automated DNA sequencer and the PRISM dye terminator kit.

Construction of a Hybrid fVIII Expression Vector, HP20, Containing the Porcine C2 Domain.

A porcine fVIII cDNA corresponding to the 3' end of the C1 domain and all of the C2 domain was cloned into pBluescript by RT-PCR from spleen total RNA using primers based on known porcine fVIII cDNA sequence [Healey, J. F. et al. (1996) Blood 88:42094214]. This construct and HB$^-$/ReNeo were used as templates to construct a human C1-porcine C2 fusion product in pBlueScript by SOE mutagenesis. The C1-C2 fragment in this plasmid was removed with ApaI and NotI and ligated into ApaI/NotI-cut HB$^-$/ReNeo/NotI to produce HP20/ReNeo/NotI.

Construction of B-domain Deleted Hybrid Human/porcine fVIII Containing the Porcine Light Chain (HP18)-

The human fVIII light chain consists of amino acid residues Asp1649-Tyr2332. The corresponding residues in the porcine fVIII cDNA were substituted for this region of HB$^-$ to produce a hybrid human/porcine fVIII molecule designated HP18. This was done by substituting a PCR product corresponding to porcine A2 region, the A3 domain, the C 1 domain, and part of the C2 domain for the corresponding region in HP20. To facilitate constructions, a synonymous AvrII site was introduced into nt 2273 at the junction of the A2 and A3 domains of HP20 by SOE mutagenesis.

Construction of B-domain Deleted Hybrid Human/porcine fVIII Containing the Porcine Signal Peptide, A1 Domain and A2 Domain (HP22)-

The human fVIII signal peptide, A1 domain and A2 domains consist of amino acid residues Met(-19)-Arg740. The corresponding residues in the porcine fVIII cDNA were substituted for this region of HB- to produce a molecule designated HP22. Additionally, a synonymous AvrII site was introduced into nt 2273 at the junction of the A2 and A3 domains of HP22 by SOE mutagenesis. HP22 was constructed by fusion of a porcine signal peptide-A1-partial A2 fragment in pBlueScript [Healy et al. (1996) supra] with a B-domainless hybrid human/porcine fVIII containing the porcine A2 domain, designated HP1 [Lubin et al. (1994) supra].

Construction of Porcine B Domainless fVIII-(PB$^-$)

A SpeI/NotI fragment of HP18/BS (+AvrII) was digested with AvrII/NotI and ligated into AvrII/NotI-digested HP22/BS (+AvrII) to produce a construct PB$^-$/BS (+AvrII), which consists of the porcine fVIII lacking the entire B domain. PB- was cloned into ReNeo by ligating an Xba/NotI fragment of PB$^-$/BS (+AvrII) into HP22/ReNeo/NotI (+AvrII).

Expression of Recombinant fVIII Molecules

PB$^-$/ReNeo/NotI (+AvrII) and HP22/ReNeo/NotI (+AvrII) were transiently transfected into COS cells and expressed as described previously [Lubin, I. M. et al. (1994) J. Biol. Chem. 269:8639–8641]. HB$^-$/ReNeo/NotI and no DNA (mock) were transfected as a control.

The fVIII activity of PB$^-$, HP22, and HB$^-$ were measured by a chromogenic assay as follows. Samples of fVIII in COS cell culture supernatants were activated by 40 nM thrombin in a 0.15 M NaCl, 20 mM HEPES, 5Mm cAC12, 0.01% Tween-80, pH 7.4 in the presence of 10 nM factor IXa, 425 nM factor X, and 50 µM unilamellar phosphatidylserine-[phosphatidycholine (25/75 w/w) vesicles. After 5 min, the reaction was stopped with 0.05 M EDTA and 100 nM recombinant desulfatohirudin and the resultant factor Xa was measured by chromogenic substrate assay. In the chromogenic substrate assay, 0.4 mM Spectrozyme Xa was added and the rate of para-nitroanilide release was measured by measuring the absorbance of the solution at 405 nm.

Results of independently transfected duplicate cell culture supernatants (absorbance at 405 nm per minute)

HB$^-$: 13.9

PB$^-$: 139

HP22: 100 mock: <0.2

These results indicate that porcine B-domainless fVIII and a B-domainless fVIII consisting of the porcine A1 and A2 subunits are active and suggest that they have superior activity to human B-domainless fVIII.

PB$^-$ was partially purified and concentrated from the growth medium by heparin-Sepharose chromatography. Heparin-Sepharose (10 ml) was equilibrated with 0.075 M NaCl, 10 MM HEPES, 2.5 mM CaCl$_2$1 0.005% Tween-80, 0.02% sodium azide, pH 7.40. Medium (100–200 ml) from expressing cells was applied to the heparin-Sepharose, which then was washed with 30 ml of equilibration buffer without sodium azide. PB$^-$ was eluted with 0.65 M NaCl, 20 mM HEPES, 5 mM CaCl$_2$, 0.01% Tween-80, pH 7.40 and was stored at →80° C. The yield of fVIII coagulant activity was typically 50–75%.

Stable Expression of Porcine B-domainless fVIII (PB$^-$)

Transfected cell lines were maintained in Dulbecco's modified Eagle's medium-F12 containing 10% fetal bovine serum, 50 U/ml penicillin, 50 µg/ml streptomycin. Fetal bovine serum was heat inactivated at 50° C. for one hour before use. HB$^-$/ReNeo and PB$^-$ReNeo/NotI (+AvrII) were stably transfected into BHK cells and selected for geneticin resistance using a general protocol that has been described previously [Lubin et al. (1994) Biol. Chem. 269:8639–8641] except that expressing cells were maintained in growth medium containing 600 µg/ml geneticin. Cells from Corning T-75 flasks grown to confluence were transferred to Nunc triple flasks in medium containing 600 µg/ml geneticin and grown to confluence. The medium was removed and replaced with serum-free, AIM-V medium (Life Technologies, Inc.) without geneticin. Factor VIII expression was monitored by one-stage factor VIII coagulant activity (vide supra) and 100–150 ml of medium was collected once daily for four to five days. Maximum expression levels in medium for HB$^-$ and PB$^-$ were 102 units per ml and 10–12 units per ml of factor VIII coagulant activity, respectively.

Purification of PB$^-$

PB$^-$ was precipitated from culture supernatant using 60% saturated ammonium sulfate and then purified by W3–3 immunoaffinity chromatography and mono Q high pressure liquid chromatography as described previously for the purification of plasma-derived porcine factor VIII [Lollar et al. (1993) Factor VIII/factor VIIIa. Methods Enzymol. 222:128–143]. The specific coagulant activity of PB$^-$ was measured by a one-stage coagulation assay [Lollar et al. (1993) supra] and was similar to plasma-derived porcine factor VIII.

When analyzed by SDS-polyacrylamide gel electrophoresis, the PB$^-$ preparation contained three bands of apparent molecular masses 160 kDa, 82 kDa, and 76 kDa. The 82 kDa and 76 kDa bands have been previously described as heterodimer containing the A1-A2 and ap-A3-

C1-C2 domains (where ap refers to an activation peptide) [Toole et al. (1984) *Nature* 312:342–347]. The 160 kDa band was transferred to a polyvinylidene fluoride membrane and subjected to NH2-terminal sequencing, which yielded Arg-Ile-Xx-Xx-Tyr (where Xx represents undermined) which is the NH2-terminal sequence of single chain factor VIII [Toole et al. (1984) supra]. Thus, PB⁻ is partially processed by cleavage between the A2 and A3 domains, such that it consists of two forms, a single chain A1-A2-ap-A3-C1-C2 protein and a A1-A2/ap-A3-C1-C2 heterodimer. Similar processing of recombinant HB- has been reported [Lind et al. (1995) *Eur. J. Biochem.* 232:19–27].

Characterization of Porcine Factor VIII

We have determined the cDNA sequence of porcine fVIII corresponding to 137 bp of the 5' UTR, the signal peptide coding region (57 bp), and the A1 (1119 bp), A3 (990 bp), C1 (456 bp), and C2 (483 bp) domains. Along with previously published sequence of the B domain and light chain activation peptide regions [Toole et al. (1986) supra] and the A2 domain [Lubin et al. (1994) supra], the sequence reported here completes the determination of the porcine. fVIII cDNA corresponding to the translated product. A fragment that included the 5' UTR region, signal peptide, and A1 domain cDNA was cloned using a 5'-RACE RT-PCR protocol. A primer based on human C2 sequence was successful in producing an RT-PCR product that led to cloning of the A3, C1, and 5' half of the C2 domain. The cDNA corresponding to the 3' half of the C2 domain and 3' UTR cDNA proved difficult to clone. The remainder of the C2 domain ultimately was cloned by a targeted gene walking PCR procedure [Parker et al. (1991) supra].

The sequence reported herein SEQ ID NO:29 was unambiguous except at nt 7045 near the 3' end of the C2 domain, which is either A or G as described hereinabove. The corresponding codon is GAC (Asp) or AAC (Asn). The human and mouse codons are GAC and CAG (Gln), respectively. Whether this represents a polymorphism or a reproducible PCR artifact is unknown. Recombinant hybrid human/porcine B-domainless fVIII cDNAs containing porcine C2 domain substitutions corresponding to both the GAC and AAC codons have been stably expressed with no detectable difference in procoagulant activity. This indicates that there is not a functional difference between these two C2 domain variants.

The alignment of the predicted amino acid sequence of full-length porcine fVIII SEQ ID NO:30 with the published human [Wood et al. (1984) supra] and murine [Elder et al. (1993) supra] sequences is shown in FIGS. 1A–1H along with sites for post-translational modification, proteolytic cleavage, and recognition by other macromolecules. The degree of identity of the aligned sequences is shown in Table VII. As noted previously, the B domains of these species are more divergent than the A or C domains. This is consistent with the observation that the B domain has no known function, despite its large size [Elder et al. (1993) supra; Toole et al. (1986) supra]. The results of the present invention confirm that the B domain of porcine fVIII is not necessary for activity. Based on the sequence data presented herein, porcine fVIII having all or part of the B-domain deleted can be synthesized by expressing the porcine fVIII coding DNA having deleted therefrom all or part of codons of the porcine B domain. There is also more divergence of sequences corresponding to the A1 domain APC/factor IXa cleavage peptide (residues 337–372) and the light chain activation peptide (Table VII). The thrombin cleavage site at position 336 to generate the 337–372 peptide is apparently lost in the mouse since this residue is glutamine instead of arginine [Elder et al. (1993) supra]. The relatively rapid divergence of thrombin cleavage peptides (or in mouse fVIII a possibly vestigial 337–372 activation peptide) has been previously noted for the fibrinopeptides [Creighton, T. E. (1993) In *Proteins: Structures and Molecular Properties*, W. H. Freeman, New York, pp. 105–138]. Lack of biological function of these peptides once cleaved has been cited as a possible reason for the rapid divergence. Arg562 in human fVIII has been proposed to be the more important cleavage site for activated protein C during the inactivation of fVIII and fVIIIa [Fay, P.J. et al. (1991) *J. Biol. Chem.* 266:20139–20145]. This site is conserved in human, porcine and mouse fVIII.

Potential N-linked glycosylation sites (NXS/T where X is not proline) can be seen in FIGS. 1A–1H. There are eight conserved N-linked glycosylation sites: one in the A1 domain, one in the A2 domain, four in the B domain, one in the A3 domain, and one in the C1 domain. The 19 A and C domain cysteines are conserved, whereas there is divergence of B domain cysteines. Six of the seven disulfide linkages in fVIII are found at homologous sites in factor V and ceruloplasmin, and both C domain disulfide linkages are found in factor V [McMullen, B. A. et al. (1995) *Protein Sci.* 4:740–746]. Human fVIII contains sulfated tyrosines at positions 346, 718, 719, 723, 1664, and 1680 [Pittman, D. D. et al. (1992) *Biochemistry* 31:3315–3325; Michnick, D. A. et al. (1994) *J. Biol. Chem.* 269:20095–20102]. These residues are conserved in mouse fVIII and porcine fVIII (FIG. 1), although the CLUSTALW program failed to align the mouse tyrosine corresponding to Tyr346 in human fVIII.

Mouse and pig plasma can correct the clotting defect in human hemophilia A plasma, which is consistent with the level of conservation of residues in the A and C domains of these species. The procoagulant activity of porcine fVIII is superior to that of human fVIII [Lollar, P. et al. (1992) *J. Biol. Chem.* 267:23652–23657]. The recombinant porcine factor VIII (B domain-deleted) expressed and purified as herein described also displays greater specific coagulant activity than human fVIII, being comparable to plasma-derived porcine fVIII. This may be due to a decreased spontaneous dissociation rate of the A2 subunit from the active A1/A2/A3-C1-C2 fVIII heterotrimer. Whether this difference in procoagulant activity reflects an evolutionary change in function as an example of species adaptation [Perutz, M. F. (1996) *Adv. Protein Chem.* 36:213–244] is unknown. Now that the porcine fVIII cDNA sequence corresponding to the translated product is complete, homolog scanning mutagenesis [Cunningham, B. C., et al. (1989) *Science* 243:1330–1336] may provide a way to identify structural differences between human and porcine fVIII that are responsible for the superior activity of the latter.

Porcine fVIII is typically less reactive with inhibitory antibodies that arise in hemophiliacs who have been transfused with fVIII or which arise as autoantibodies in the general population. This is the basis for using porcine fVIII concentrate in the management of patients with inhibitory antibodies [Hay and Lozier (1995) supra]. Most inhibitors are directed against epitopes located in the A2 domain or C2 domain [Fulcher, C. A. et al. (1985) *Proc. Natl. Acad. Sci. USA* 82:7728–7732; Scandella, D. et al. (1988) *Proc. Natl. Acad. Sci. USA* 85:6152–6156; Scandella, D. et al. (1989) *Blood* 74:1618–1626]. Additionally, an epitope of unknown significance has been identified that is in either the A3 or C1 domain [Scandella et al. (1989) supra; Scandella, D. et al. (1993) *Blood* 82:1767–1775; Nakai, H. et al. (1994) *Blood* 84:224a]. The A2 epitope has been mapped to residues 484–508 by homolog scanning mutagenesis [Healey et al. (1995) supra]. In this 25 residue segment, there is relatively low proportion of identical sequence (16/25 or 64%). It is interesting that this region, which appears to be functionally important based on the fact that antibodies to it are inhibitory, apparently has been subjected to relatively more rapid genetic drift. Alignment of the porcine A2 domain and A3 domains indicate that the A2 epitope shares no detectable homology with the corresponding region in the A3 domain.

The C2 inhibitor epitope of human fVIII has been proposed to be located to within residues 2248–2312 by deletion mapping [Scandella, D. et al. (1995) *Blood* 86:1811–1819]. Human and porcine fVIII are 83% identical in this 65 residue segment. However, homolog scanning mutagenesis of this region to characterize the C2 epitope has revealed that a major determinant of the C2 epitope was unexpectedly located in the region corresponding to human amino acids 2181–2243 (SEQ ID NO:2) and FIG. 1H.

Human-porcine hybrid factor VIII proteins were made in which various portions of the C2 domain of human factor VIII were replaced by the corresponding portions of porcine factor VIII, using the strategy herein described. (Example 5) The synthesis of the various C2-hybrid factor VIIIs was accomplished by constructing hybrid coding DNA, using the nucleotide sequence encoding the porcine C2 region given in SEQ ID NO:30. Each hybrid DNA was expressed in transfected cells, such that the hybrid factor VIIIs could be partially purified from the growth medium. Activity,. in the absence of any inhibitor, was measured by the one-stage clotting assay.

A battery of five human inhibitors was used to test each hybrid factor VIII. The inhibitor plasmas containing anti factor VIII antibody had been previously shown to be directed against human C2 domain, based on the ability of recombinant human C2 domain to neutralize the inhibition. In all the test plasmas, the inhibitor titer was neutralized greater than 79% by C2 domain or light chain but less than 10% by recombinant human A2 domain. In addition the C2-hybrid factor VIIIs were tested against a murine monoclonal antibody, which binds the C2 domain, and like human C2 inhibitor antibodies, it inhibited the binding of factor VIII to phospholipid and to von Willebrand factor.

By comparing the antibody inhibitor titers against the C2-hybrid factor VIIIs, the major determinant of the human C2 inhibitor epitope was shown to be the region of residues 2181–2243 (SEQ ID NO:2, see also FIG. 1H). Anti-C2 antibodies directed to a region COOH-terminal to residue 2253 were not identified in four of the five patient sera. In comparing hybrids having porcine sequence corresponding to human amino acid residues numbers 2181–2199 and 2207–2243, it was apparent that both regions contribute to antibody binding. The porcine amino acid sequence corresponding to human residues 2181–2243 is numbered 1982–2044 in SEQ ID NO:30. The sequence of porcine DNA encoding porcine amino acids numbered 1982–2044 is nucleotides numbered 5944–6132 in SEQ ID NO:29.

Referring to FIG. 1H, it can be seen that in the region 2181–2243, there, are 16 amino acid differences between the human and porcine sequences. The differences are found at residues 2181, 2182, 2188, 2195–2197, 2199, 2207, 2216, 2222, 2224–2227, 2234, 2238 and 2243. Amino acid replacement at one or more of these numbered residues can be carried out to make a modified human factor VIII non-reactive to human anti-C2 inhibitor antibodies. Alanine scanning mutagenesis provides a convenient method for generating alanine substitutions for naturally-occurring residues, as previously described. Amino acids other than alanine can be substituted as well, as described herein. Alanine substitutions for individual amino acids, especially those which are non-identical between human/porcine or human/mouse or which are most likely to contribute to antibody binding; can yield a modified factor VIII with reduced reactivity to inhibitory antibodies.

FIGS. 1A–1H taken together provide an aligned sequence comparison of the human, pig and mouse factor VIII amino acid sequences. FIG. 1A compares signal peptide regions (human, SEQ ID NO:31; porcine, SEQ ID NO:30, amino acids 1–19; murine, SEQ ID NO:28, amino acids 1–19). Note that the amino acids in FIGS. 1A–1H are numbered at the first Alanine of the mature protein as number 1, with amino acids of the signal peptide assigned negative numbers. The Human fVIII sequence in SEQ ID NO:2 also begins with the first Alanine of the mature protein as amino acid number 1. In the amino acid sequences of mouse fVIII (SEQ ID NO:28) and porcine fVIII (SEQ ID NO:30), the first amino acid (alanine) of the mature sequence is amino acid number 20. FIGS. 1A–1H shows an alignment of the corresponding sequences of human, mouse and pig fVIII, such that the regions of greatest amino acid identity are juxtaposed. The amino acid numbers in FIGS. 1A–1H apply to human fVIII only. FIG. 1B gives the amino acid sequences for the A1 domain of human (SEQ ID NO:2, amino acids 1–372), porcine (SEQ ID NO:30, amino acids 20–391), and murine (SEQ ID NO:28, amino acids 20–391). FIG. 1C provides amino acid sequences for the Factor VIII A2 domains from human (SEQ ID NO:2, amino acids 373–740), pig (SEQ ID NO:30, amino acids 392–759) and mouse (SEQ ID NO:28, amino acids 392–759). FIG. 1D provides the amino acid sequences of B domains of human factor VIII (SEQ ID NO:2, amino acids 741–1648), pig (SEQ ID NO:30, amino acids 760–1449) and mouse (SEQ ID NO:28, amino acids 760–1640). FIG. 1E compares the amino acid sequences of Factor VIII light chain activation peptides of human, pig and mouse (SEQ ID NO:2, amino acids 1649–1689; SEQ ID NO:30, amino acids 1450–1490; and SEQ ID NO:28, amino acids 1641–1678, respectively). FIG. 1F provides the sequence comparison for human, pig and mouse Factor VIII A3 domains (SEQ ID NO:2, amino acids 1690–2019; SEQ ID NO:30, amino acids 1491–1820; and SEQ ID NO:28, amino acids 1679–2006, respectively. FIG. 1G provides the amino acid sequences of the Factor VIII C1 domains of human, pig and mouse (SEQ ID NO:2, amino acids 2020–2172; SEQ ID NO:30, amino acids 1821–1973; and SEQ ID NO:28, amino acids 2007–2159, respectively). FIG. 1H provides sequence data for the C2 domains of the Factor VIII C2 domains of human, pig and mouse (SEQ ID NO:2, amino acids 2173–2332; SEQ ID NO:30, amino acids 1974–2133; and SEQ ID NO:28, amino acids 2160–2319, respectively).

The diamonds represent tyrosine sulfation sites, proposed binding sites for Factor IXa, phospholipid and Protein C are double-underlined, and regions involved in binding anti-A2 and anti-C2 inhibitory antibodies are italicized. Asterisks highlight amino acid sequences which are conserved. See also SEQ ID NO:29 (porcine factor VIII cDNA) and SEQ ID NO:30 (deduced amino acid sequence of porcine factor VIII). The human numbering system is used as the reference [Wood et al. (1984) supra]. The A1, A2, and B domains are defined by thrombin cleavage sites at positions 372 and 740 and an unknown protease cleavage site at 1648 as residues 1–372, 373–740, and, 741–1648, respectively [Eaton, D. L. et al. (1986) *Biochemistry* 25:8343–8347]. The A3, C1, and C2 domains are defined as residues 1690–2019, 2020–2172, and 2173–2332, respectively [Vehar et al. (1984) supra].

Cleavage sites for thrombin (factor IIa), factor IXa, factor Xa and APC [Fay et al. (1991) supra; Eaton, D. et al. (1986) *Biochemistry* 25:505–512; Lamphear, B. J. et al. (1992) *Blood* 80:3120–3128] are shown by placing the enzyme name over the reactive arginine. An acidic peptide is cleaved from the fVIII light chain by thrombin or factor Xa at position 1689. Proposed binding sites for factor IXa [Fay, P. J. et al. (1994) *J. Biol. Chem.* 269:20522–20527; Lenting, P. J. et al. (1994) *J. Biol. Chem.* 269:7150–7155), phospholipid (Foster, P. A. et al. (1990) *Blood* 75:1999–2004) and protein C (Walker, F. J. et al. (1990) *J. Biol. Chem.* 265:1484–1489] are doubly underlined. Regions involved in binding anti-A2 [Lubin et al. (1994) supra; Healey et al. (1995) supra]; and previously proposed for anti-C2 inhibitory antibodies are italicized. The C2 inhibitor epitope identified as herein described (human amino acids 2181–2243) is shown by a single underline in FIG. 1H. Tyrosine sulfation sites [Pittman et al. (1992) supra; Michnick et al. (1994) supra] are shown by ♦.

EXAMPLE 7

Construction of POL1212 and Expression in Baby Hamster Kidney Cells.

POL1212 is a partially B-domainless porcine factor VIII, having the B-domain deleted except that 12 amino acids of the NH2 terminus of the B-domain and 12 amino acids of the —COOH terminus are retained.

The cDNAs encoding for the sequences for the porcine fVIII domains A1, A2, ap-A3-C1, and C2 were obtained as described in Example 5. The DNA nucleotide sequence and derived amino acid sequence of porcine factor VIII are presented as SEQ ID NO:29 and SEQ ID NO:30, respectively. The amplified fragments were separately cloned into the plasmid pBluescript II KS⁻ (pBS).

POL1212 refers to the cDNA encoding porcine fVIII lacking most of the B domain but containing DNA sequence encoding a 24 amino acid linker between the A2 and ap domains. POL1212 was constructed in a mammalian expression vector, ReNeo, which was obtained from Biogen. ReNeo can replicate in bacteria, replicate as an episome in COS cells for transient expression of factor VIII, or be stably integrated into a variety of mammalian cells. It consists of 1) sequences derived from plasmid pBR322 that include an origin of replication and ampicillin resistance gene, 2) a neomycin resistance gene whose expression is under control of the SV40 promoter/enhancer, SV40 small t intron, and the SV40 polyadenylation signal regulatory elements, 3) a site for insertion of fVIII and its signal peptide, the expression of which is under control of the SV40 enhancer, adenovirus type 2 major late promoter, and adenovirus type 2 tripartite leader sequence. Any vector having similar functional components can be used in place of the ReNeo vector.

POL1212/ReNeo was prepared in several steps. First, the cDNAs encoding for porcine fVIII heavy chain (A1-A2) and the cDNAs encoding for porcine fVIII light chain (ap-A3-C1-C2) were separately assembled in pBS. From these constructs, the DNA encoding for porcine B-domainless fVIII was assembled in pBS (PB-/pBS). This form of porcine fVIII lacks the entire B domain, defined as amino acids corresponding to residues 741–1648 in human fVIII (human nucleotides 2278–5001). Next, the DNA encoding for porcine A2 was substituted for the human A2 domain in the human B-domainless fVIII expression vector ReNeo (HB-/ReNeo). The DNA encoding the remainder of the porcine heavy chain and the DNA encoding the porcine light chain was substituted for the human domains in two additional steps using the porcine heavy chain/pBS and PB-/pBS constructs made previously. A fragment of the human B domain encoding the 5 C-terminal and 9 N-terminal amino acids was inserted between the A2 and A3 domains producing a construct called PSQ/ReNeo [Healey et al. (1998)/ 92:3701–3709]. Residues Glu2181-Val2243 contain a major determinant of the inhibitory epitope in the C2 domain of human factor VIII). This construct was used as a template to make a fragment of the porcine B domain encoding for the 12 C-terminal and 12 N-terminal amino acids. This fragment was inserted between the A2 and A3 domains resulting in the final construct, POL1212/ReNeo.

The POL1212 24 amino acid linker consists of the first 12 and last 12 residues of the porcine fVIII B domain. The POL1212 linker has the following sequence: SFAQNSRPP-SASAPKPPVLRRHQR. (SEQ ID NO:32)

The nucleotide sequence corresponding to the 1212 linker and surrounding amino acids is:

```
GTC ATT GAA CCT AGG AGC TTT GCC CAG AAT TCA AGA CCC CCT AGT GCG    (SEQ ID NO:33)

V   I   E   P   R   S   F   A   Q   N   S   R   P   P   S   A

AGC GCT CCA AAG CCT CCG GTC CTG CGA CGG CAT CAG AGG GAC ATA

S   A   P   K   P   P   V   L   R   R   H   Q   R   D   I

AGC CTT CCT ACT

S   L   P   T
```

The POL1212 linker was synthesized by splicing-by-overlap extension (SOE) mutagenesis, as follows:
PCR reactions used to make SOE Products were as Follows:
REACTION #1
Outside primer: Rev 4, which is a porcine A2 primer, nucleotides 1742–1761. (SEQ ID NO:29) The sequence is: 5'-GAGGAAAACCAGATGATGTCA-3' (SEQ ID NO:34)
Inside primer: OL12, which is a porcine reverse primer covering the first (5') 15 amino acids of OL1212 and the last (3') 5 amino acids of porcine A2. The sequence is: 5'-CTT TGGAGCGCTCGCACTAGGGGGTCTTGAATTCTGGG CAAAGCTCCTAGGTTCAATGAC-3' (SEQ ID NO:35)
Template: PSQ/ReNeo
Product: porcine DNA from nucleotide 1742 in the A2 domain to 2322 in OL1212, 580 bp
REACTION #2
Outside primer: P2949 is a porcine reverse A3 primer, nucleotides 2998–3021 of SEQ ID NO:29. The sequence is: 5'-GGTCACTTGTCTACCGTGAGCAGC -3' (see SEQ ID NO:29)
Inside primer: OL12+, a porcine primer covering the last (3') 16 amino acids of OL1212 and the first (5') 6 amino acids of the activation peptide, nucleotide 2302–2367 of SEQ ID NO:29. The sequence is: 5' -CCTAGTGCGAGC GCTCCAAAGCCTCCGGTCCTGCGACGGCATCAGAG GGACATAAGCCTTCCTACT-3' (SEQ ID NO:36)

Template: PSQ/ReNeo_

Product: porcine from nucleotide 2302 in OL1212 to nucleotide 3021 in the A3 domain, 719 bp

SOE REACTION

Primers: Rev 4, P2949-

Templates: Fragment from rxn #1 (bp) and low melt fragment from rxn #2 (bp)

Product: porcine DNA from nucleotide 1742 in the A2 domain to nucleotide 3021 in the A3 domain (SEQ ID NO:29) including OL1212, 1279 bp. The reaction product was ethanol precipitated.

The 1212 linker was inserted into PSQ/ReNeo by cutting the SOE product (insert) and PSQ/ReNeo (vector) with BsaB I. The vector and insert were ligated using T4 ligase and the product was used to transform E. coli XL1-Blue cells. Plasmid DNA was prepared from several colonies and the sequence of the 1212 linker and other PCR-generated sequence was verified by DNA sequence analysis.

CULTURE OF BABY HAMSTER KIDNEY (BHK) CRL-1632 CELLS

A BHK cell line was obtained from the ATCC, accession identification CRL-1632 and was stored frozen at −20° C. until further use. The cells were thawed at 37° C. and put into 10 ml of complete medium, defined as DMEM/F12, 50 U/ml penicillin, 50 µg/ml streptomycin plus 10% fetal bovine serum (FBS). FBS was purchased from Hyclone, Logan Utah. The cells were centrifuged for 2 minutes at 300 RPM. The medium was aspirated and the cells were resuspended in two ml complete medium in a T-75 flask containing 20 ml of complete medium.

POL1212 has been expressed in both baby hamster kidney (BHK) and Chinese hamster ovary (CHO) cells. Two BHK lines were used, the CRL-1632 line from ATCC and another BHK line obtained from R. Mcgillivray, University of British Columbia, [Funk, et al. (1990) *Biochemistry* 29:1654–1660]. The latter were subcultured without selection in the inventors lab and designated BHK1632 (Emory). The CHO cell line was CHO-K1, ATCC accession CCL-61. The expression of the average clone from the Emory cell line and from CHO-K1 cells was somewhat higher than from CRL-1632 cells as judged by chromogenic assay activity.

The cells grown in the T-75 flask formed a confluent monolayer. A 60 ml culture of E. coli XL1-Blue cells in LB/ampicillin (50 mg/mi) carrying the POL1212/ReNeo plasmid was prepared.

TRANSFECTION OF CRL-1632 BHK CELLS WITH POL1212/ReNeo

DNA from the overnight culture of the POL1212/ReNeo XL1-Blue cells was prepared using a Qiagen, Valencia, Calif. Spin Miniprep kit. One flask of CRL-1632 cells was split into a stock flask with 0.2 ml and a flask for transfection with 0.3 ml from 2 ml total. The other flask was fed fresh medium. Medium was DMEM/F12+10% Hyclone FBS+50 U/ml penicillin, 50 µg/ml streptomycin. CRL-1632 cells were split into 6 well plates aiming for 50–90% confluence for transfection (0.3 ml of cells from the T-75 flask in 2 ml 1:5000 Versene [Life Technologies, Gaithersburg, Md.] in each well) using fresh DMEM/F12+10% Hyclone FBS+50 U/ml penicillin, 50 µg/ml streptomycin.

The following solutions were prepared in sterile 1–2 ml test tubes;

A) 48 µl (10 µg) Miniprep POL1212/ReNeo DNA plus µl medium without serum (DMEM/F12) plus 10 µl Lipofectin™ (Life Technologies, Gaithersburg, Md.).

B) 10 µl Lipofectin plus 190 µl medium (mock transfection) was gently mixed and the DNA and Lipofectin allowed to react for 15 minutes at room temperature. During this time, the cells were washed twice with 2 ml of DMEM/F12. 1.8 ml of DMEM/F12 was then added to the cells. The DNA/Lipofectin complex was added dropwise to the cells, and swirled gently to mix. The cells remained in the incubator overnight. Removed the DNA/Lipofectin and added 3 ml of medium with serum to the cells. Incubated the cells 30–48 hours. Geneticin was purchased from Life Technologies, Gaithersburg, Md. The cell cultures were divided 1:20, 1:50 and 1:100, 1:250, 1:500 onto 10 cm dishes in 10 ml of medium with serum containing 535 µg/ml geneticin. Over the next several days, cells that did not take up the POL1212/ReNeo plasmid were killed due to the presence of geneticin. The remaining cells continued to replicate in geneticin, forming visible monolayer colonies on the dishes.

EXPRESSION AND ASSAY OF POL1212 from BHK CRL-1632 CELLS

Small plastic cylindrical rings were placed around the colonies. The colonies were aspirated separately using complete medium and transferred to test tubes. These colonies are referred to as ring cloned colonies. Ring cloned colonies were plated separately onto 24 well plates and grown in complete medium.

CHROMOGENIC SUBSTRATE ASSAY FOR FACTOR VIII EXPRESSION BY TRANSFECTED CRL-1632 CELLS

Samples of POL1212 from cell culture supernatants were mixed with 50 nM purified porcine factor IXa and 0,05 mM phosphtidylcholine/phosphatidylserine (PCPS) vesicles in 0. 15M NaCl, 20 m HEPES, 5mM CaCl2, 0.01% Tween 80, pH 7.4. As a control, cell culture medium from mock-transfected cells was used. Thrombin and factor X were added simultaneously to final concentrations of 40 and 425 nM, respectively. thrombin activates factor VIII, which then, along with PCPS, serves as a cofactor for factor IXa during the activation of factor X.

After 5 min, the activation of factor X by factor IXa/factor VIIIa/PCPS was stopped by the addition of EDTA to a final concentration of 50 mM. At the same time the activation of factor VIII by thrombin was stopped by the addition of the thrombin inhibitor, recombinant desulfatohirudin, to a final concentration of 100 nM. A 25-µl sample of the reaction mix was transferred to a microtiter well, to which was added 74 µl of Spectrozyme Xa (America Diagnostica, Greenwich, Conn.), which is a chromogenic substrate for factor Xa. The final concentration of Spectrozyme Xa was 0.6 mM. The absorbance at 405 nm due to the cleavage of Spectrozyme Xa by factor Xa was monitored continuously for 5 minutes with a Vmax Kinetic Plate Reader (Molecular Devices, Inc., Menlo park, Calif.). The results are expressed in terms of A405/min.

Factor VIII chromogenic assay of ten ring-cloned colonies:

| Colony number | $A_{405}$/min ($\times 10^3$) |
|---|---|
| Buffer | 0.2 |
| 1 | 2.1 |
| 2 | 8.4 |
| 3 | 6.4 |
| 4 | 10.7 |
| 5 | 12.5 |
| 6 | 7.6 |
| 7 | 51.3 |
| 8 | 139.5 |
| 9 | 3.8 |
| 10 | 8.4 |

These results show that all ten colonies that were selected express factor VIII activity that is at least ten-fold greater than background.

The activity from medium of colony 8, which was the highest expressing colony, was further examined by one-state factor VIII clotting assay. In this assay, 50 ml of factor VIII deficient plasma (George King Biomedical Overland Park, Kans.), 5 ml sample or standard, and 50 ml of activated particulate thromboplastin time reagent (Organon Teknika, Durham, N.C.) were incubated 3 min at 37° C. Samples include colony 8 medium diluted in 0.15 M NaCl, mM hepes, pH 7.4 (HBS) or, as a control, complete medium. Clotting was initiated by addition of 50 ml of 20 mM CaCl2. The clotting time was measured using an ST4 BIO Coagulation Instrument (Diagnostica Stago, Parsippany, N.J.). A standard curve was obtained by making dilutions of pooled, citrated normal human plasma, lot 0641 (George King Biomedical, Overland Park, Kans.). The factor VIII concentration of the standard was 0.9 units per ml.

Standard Curve:

| | Dilution | U/ml | Clot Time |
|---|---|---|---|
| 1) | Undiluted | 0.96 | 45.2 |
| 2) | 1/3 (HBS) | 0.32 | 53.7 |
| 3) | 1/11 (HBS) | 0.087 | 62.5 |
| 4) | 1/21 (HBS) | 0.046 | 68.9 |

Linear regression of the clotting times versus the logarithm of the concentration of standard yielded a correlation coefficient of 0.997.

Test substances gave the following clotting times, which were converted to units per ml using the standard curve:

| Sample | Clot Time (sec) | Units/ml |
|---|---|---|
| 1) Colony 8 (24 h), 1/10 in HBS | 40.6 | 1.74 × 10 = 17.4 |
| 2) Colony 8 (24 h), 1/10 in HBS | 41.1 | 1.63 × 10 = 16.3 |
| 3) Colony 8 (24 h), 1/20 in HBS | 47.7 | 0.69 × 20 = 13.8 |
| 4) Colony 8 (24 h), 1/20 in HBS | 47.2 | 0.73 × 20 = 14.6 |
| 5) Complete medium | 82.9 | 0.007 |
| 6) Complete medium | 83.3 | 0.006 |

These results show that colony 8 clotting activity that is approximately 2000-fold higher than the control sample.

The DNA sequence encoding POL1212 is set forth as SEQ ID NO:37. The encoded amino acid sequence of POL1212 is set forth as SEQ ID NO:38. Further purification of POL1212 can be carried out using a variety of known methods such as immunoaffinity chromatography and HPLC chromatography—see Examples 2 and 3.

GENERAL CONCLUDING REMARKS

It will be understood that minor variations of amino acid sequence or the DNA encoding such sequence relating to POL1212 can be introduced without affecting the essential attributes of function. For example, the length of B-domain sequence retained as a linker between the A2 domain and the activation peptide can be increased or decreased within limits known in the art. Sequence variants can be introduced in the linker region while retaining the equivalent functional attributes of POL1212 as taught herein and of porcine B-domainless factor VIII as taught herein and as known in the art. Based on comparisons of known factor VIII amino acid sequences having coagulant activity in human blood, sequence variants such as individual amino acid substitutions or substitution of peptide segments with known functional variants can be made in the basic POL1212 amino acid sequence, while retaining the equivalent functional attributes thereof. The foregoing types of variation are not intended as exhaustive, but are merely exemplary of the sequence modifications that could be made by those of ordinary skill in the art, without substantially modifying the functional attributes of the protein. All such variants and modifications are deemed to fall within the scope of the invention as claimed or as equivalents thereof.

Sequence ID Listing

| SEQ ID NO: | Identification |
|---|---|
| 1 | Human factor VIII cDNA. Coding for amino acid number 1 of the mature protein begins at nucleotide number 208. |
| 2 | Human factor amino acid sequence. |
| 3 | Porcine factor VIII A2 domain cDNA |
| 4 | Porcine factor VIII A2 domain amino acid sequence |
| 5 thru 27 | Oligonucleotide primer seq. (Example 5) |
| 28 | Murine factor VIII amino acid sequence |
| 29 | Porcine factor VIII cDNA |
| 30 | Porcine factor VIII amino acid sequence |
| 31 | Human factor VIII signal peptide amino acid sequence |
| 32 thru 36 | Oligonucleotiode primer (Example 7) |
| 37 | POL1212 coding DNA |
| 38 | POL1212 amino acid sequence |

The BHK 1632 (Emory) cell line was deposited with the American Type Culture Collection, 10801 University Blvd., Manassas, VA, 20110-2209, under the designation BHK-M on Jun. 27, 2002 (Deposited as PTA-4506).

What is claimed is:

1. An isolated DNA molecule encoding the amino acid sequence of POL1212 as set forth in SEQ ID NO:38.

2. An expression vector comprising a DNA molecule according to claim 1.

3. An isolated DNA molecule according to claim 1 having the nucleotide sequence of SEQ ID NO:37.

4. An expression vector comprising a DNA molecule according to claim 3.

5. An isolated mammalian host cell containing and replicating an expression vector comprising DNA encoding the amino acid sequence of POL1212 as set forth in SEQ ID NO:38.

6. An isolated mammalian host cell according to claim 5 wherein the vector comprises DNA having the nucleotide sequence of SEQ ID NO:37.

7. A cell according to claim 6 wherein the host cell is BHK CRL-1632.

8. A method for producing a modified porcine factor VIII protein having the amino acid sequence of SEQ ID NO:38 comprising expressing in a mammalian host cell a DNA molecule encoding the amino acid sequence of SEQ ID NO:38.

9. The method of claim 8 wherein the DNA molecule encoding the amino acid sequence of SEQ ID NO:38 also encodes a signal peptide, whereby the modified porcine factor VIII protein is from the most cell.

10. The method of claim 9 wherein the signal peptide has the sequence of amino acids 1–19 of SEQ ID NO:30.

* * * * *

UNITED STATES PATENT AND TRADEMARK OFFICE
CERTIFICATE OF CORRECTION

PATENT NO. : 6,458,563 B1
DATED : October 1, 2002
INVENTOR(S) : Lollar

It is certified that error appears in the above-identified patent and that said Letters Patent is hereby corrected as shown below:

Title page,
Item [63], Related U.S. Application Data, delete the following "Pat No. 5,859,204. application No. 09/523,656, which is a continuation-in-part of application" and replace with -- Pat No. 5,859,204, and of International Patent application --.

Column 1,
Line 26, delete "cascade>a" and replace with -- cascade, a --.

Column 7,
Line 39, delete "Villa" and replace with -- VIIIa --.

Column 14,
Line 38, delete "Mono QT" and replace with -- Mono $Q^{TM}$ --.

Column 17,
Line 38, delete "68using" and replace with -- 68ºC --.

Column 128,
Line 7, delete "is from the most cell" and replace with -- is exported from the mammalian host cell --.

Signed and Sealed this

Twenty-fifth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,458,563 B1  Page 1 of 1
DATED : October 1, 2002
INVENTOR(S) : Lollar It is certified that error appears in the above-identified patent and that said Letters Patent is hereby corrected as shown below:

Title page,
Item [63], Related U.S. Application Data, delete the following "Pat No. 5,859,204. application No. 09/523,656, which is a continuation-in-part of application" and replace with -- Pat No. 5,859,204, and of International Patent application --.

Column 1,
Line 26, delete "cascade>a" and replace with -- cascade, a --.

Column 7,
Line 39, delete "Villa" and replace with -- VIIIa --.

Column 14,
Line 38, delete "Mono QT" and replace with -- Mono $Q^{TM}$ --.

Column 17,
Line 38, delete "68using" and replace with -- 68ºC --.

Column 128,
Line 2, delete "is from the most cell" and replace with -- is exported from the mammalian host cell --.

This certificate supersedes Certificate of Correction issued February 25, 2003.

Signed and Sealed this

Sixth Day of May, 2003

JAMES E. ROGAN
*Director of the United States Patent and Trademark Office*

SEQUENCE LISTING

<160> NUMBER OF SEQ ID NOS: 38

<210> SEQ ID NO 1
<211> LENGTH: 9009
<212> TYPE: DNA
<213> ORGANISM: Homo sapiens
<220> FEATURE:
<221> NAME/KEY: CDS
<222> LOCATION: (208)..(7203)

<400> SEQUENCE: 1

```
cagtgggtaa gttccttaaa tgctctgcaa agaaattggg acttttcatt aaatcagaaa          60
ttttactttt ttcccctcct gggagctaaa gatattttag agaagaatta acctttgct          120 tctccagttg aacatttgta gcaataagtc atgcaaatag agctctccac ctgcttcttt          180
ctgtgccttt tgcgattctg ctttagt gcc acc aga aga tac tac ctg ggt gca          234
                                Ala Thr Arg Arg Tyr Tyr Leu Gly Ala
                                  1               5 gtg gaa ctg tca tgg gac tat atg caa agt gat ctc ggt gag ctg cct           282
Val Glu Leu Ser Trp Asp Tyr Met Gln Ser Asp Leu Gly Glu Leu Pro
 10              15                  20                  25 gtg gac gca aga ttt cct cct aga gtg cca aaa tct ttt cca ttc aac           330
Val Asp Ala Arg Phe Pro Pro Arg Val Pro Lys Ser Phe Pro Phe Asn
             30                  35                  40 acc tca gtc gtg tac aaa aag act ctg ttt gta gaa ttc acg gtt cac           378
Thr Ser Val Val Tyr Lys Lys Thr Leu Phe Val Glu Phe Thr Val His
         45                  50                  55 ctt ttc aac atc gct aag cca agg cca ccc tgg atg ggt ctg cta ggt           426
Leu Phe Asn Ile Ala Lys Pro Arg Pro Pro Trp Met Gly Leu Leu Gly
     60                  65                  70 cct acc atc cag gct gag gtt tat gat aca gtg gtc att aca ctt aag           474
Pro Thr Ile Gln Ala Glu Val Tyr Asp Thr Val Val Ile Thr Leu Lys
 75                  80                  85 aac atg gct tcc cat cct gtc agt ctt cat gct gtt ggt gta tcc tac           522
Asn Met Ala Ser His Pro Val Ser Leu His Ala Val Gly Val Ser Tyr
 90                  95                 100                 105 tgg aaa gct tct gag gga gct gaa tat gat gat cag acc agt caa agg           570
Trp Lys Ala Ser Glu Gly Ala Glu Tyr Asp Asp Gln Thr Ser Gln Arg
                110                 115                 120 gag aaa gaa gat gat aaa gtc ttc cct ggt gga agc cat aca tat gtc           618
Glu Lys Glu Asp Asp Lys Val Phe Pro Gly Gly Ser His Thr Tyr Val
            125                 130                 135 tgg cag gtc ctg aaa gag aat ggt cca atg gcc tct gac cca ctg tgc           666
Trp Gln Val Leu Lys Glu Asn Gly Pro Met Ala Ser Asp Pro Leu Cys
        140                 145                 150 ctt acc tac tca tat ctt tct cat gtg gac ctg gta aaa gac ttg aat           714
Leu Thr Tyr Ser Tyr Leu Ser His Val Asp Leu Val Lys Asp Leu Asn
    155                 160                 165 tca ggc ctc att gga gcc cta cta gta tgt aga gaa ggg agt ctg gcc           762
Ser Gly Leu Ile Gly Ala Leu Leu Val Cys Arg Glu Gly Ser Leu Ala
170                 175                 180                 185 aag gaa aag aca cag acc ttg cac aaa ttt ata cta ctt ttt gct gta           810
Lys Glu Lys Thr Gln Thr Leu His Lys Phe Ile Leu Leu Phe Ala Val
                190                 195                 200 ttt gat gaa ggg aaa agt tgg cac tca gaa aca aag aac tcc ttg atg           858
Phe Asp Glu Gly Lys Ser Trp His Ser Glu Thr Lys Asn Ser Leu Met
            205                 210                 215 cag gat agg gat gct gca tct gct cgg gcc tgg cct aaa atg cac aca           906
Gln Asp Arg Asp Ala Ala Ser Ala Arg Ala Trp Pro Lys Met His Thr
```

```
              220                 225                 230
gtc aat ggt tat gta aac agg tct ctg cca ggt ctg att gga tgc cac    954
Val Asn Gly Tyr Val Asn Arg Ser Leu Pro Gly Leu Ile Gly Cys His
    235                 240                 245 agg aaa tca gtc tat tgg cat gtg att gga atg ggc acc act cct gaa   1002
Arg Lys Ser Val Tyr Trp His Val Ile Gly Met Gly Thr Thr Pro Glu
250                 255                 260                 265 gtg cac tca ata ttc ctc gaa ggt cac aca ttt ctt gtg agg aac cat   1050
Val His Ser Ile Phe Leu Glu Gly His Thr Phe Leu Val Arg Asn His
                270                 275                 280 cgc cag gcg tcc ttg gaa atc tcg cca ata act ttc ctt act gct caa   1098
Arg Gln Ala Ser Leu Glu Ile Ser Pro Ile Thr Phe Leu Thr Ala Gln
            285                 290                 295 aca ctc ttg atg gac ctt gga cag ttt cta ctg ttt tgt cat atc tct   1146
Thr Leu Leu Met Asp Leu Gly Gln Phe Leu Leu Phe Cys His Ile Ser
        300                 305                 310 tcc cac caa cat gat ggc atg gaa gct tat gtc aaa gta gac agc tgt   1194
Ser His Gln His Asp Gly Met Glu Ala Tyr Val Lys Val Asp Ser Cys
    315                 320                 325 cca gag gaa ccc caa cta cga atg aaa aat aat gaa gaa gcg gaa gac   1242
Pro Glu Glu Pro Gln Leu Arg Met Lys Asn Asn Glu Glu Ala Glu Asp
330                 335                 340                 345 tat gat gat gat ctt act gat tct gaa atg gat gtg gtc agg ttt gat   1290
Tyr Asp Asp Asp Leu Thr Asp Ser Glu Met Asp Val Val Arg Phe Asp
                350                 355                 360 gat gac aac tct cct tcc ttt atc caa att cgc tca gtt gcc aag aag   1338
Asp Asp Asn Ser Pro Ser Phe Ile Gln Ile Arg Ser Val Ala Lys Lys
            365                 370                 375 cat cct aaa act tgg gta cat tac att gct gct gaa gag gag gac tgg   1386
His Pro Lys Thr Trp Val His Tyr Ile Ala Ala Glu Glu Glu Asp Trp
        380                 385                 390 gac tat gct ccc tta gtc ctc gcc ccc gat gac aga agt tat aaa agt   1434
Asp Tyr Ala Pro Leu Val Leu Ala Pro Asp Asp Arg Ser Tyr Lys Ser
    395                 400                 405 caa tat ttg aac aat ggc cct cag cgg att ggt agg aag tac aaa aaa   1482
Gln Tyr Leu Asn Asn Gly Pro Gln Arg Ile Gly Arg Lys Tyr Lys Lys
410                 415                 420                 425 gtc cga ttt atg gca tac aca gat gaa acc ttt aag act cgt gaa gct   1530
Val Arg Phe Met Ala Tyr Thr Asp Glu Thr Phe Lys Thr Arg Glu Ala
                430                 435                 440 att cag cat gaa tca gga atc ttg gga cct tta ctt tat ggg gaa gtt   1578
Ile Gln His Glu Ser Gly Ile Leu Gly Pro Leu Leu Tyr Gly Glu Val
            445                 450                 455 gga gac aca ctg ttg att ata ttt aag aat caa gca agc aga cca tat   1626
Gly Asp Thr Leu Leu Ile Ile Phe Lys Asn Gln Ala Ser Arg Pro Tyr
        460                 465                 470 aac atc tac cct cac gga atc act gat gtc cgt cct ttg tat tca agg   1674
Asn Ile Tyr Pro His Gly Ile Thr Asp Val Arg Pro Leu Tyr Ser Arg
    475                 480                 485 aga tta cca aaa ggt gta aaa cat ttg aag gat ttt cca att ctg cca   1722
Arg Leu Pro Lys Gly Val Lys His Leu Lys Asp Phe Pro Ile Leu Pro
490                 495                 500                 505 gga gaa ata ttc aaa tat aaa tgg aca gtg act gta gaa gat ggg cca   1770
Gly Glu Ile Phe Lys Tyr Lys Trp Thr Val Thr Val Glu Asp Gly Pro
                510                 515                 520 act aaa tca gat cct cgg tgc ctg acc cgc tat tac tct agt ttc gtt   1818
Thr Lys Ser Asp Pro Arg Cys Leu Thr Arg Tyr Tyr Ser Ser Phe Val
            525                 530                 535 aat atg gag aga gat cta gct tca gga ctc att ggc cct ctc ctc atc   1866
```

```
                Asn Met Glu Arg Asp Leu Ala Ser Gly Leu Ile Gly Pro Leu Leu Ile
                    540                 545                 550 tgc tac aaa gaa tct gta gat caa aga gga aac cag ata atg tca gac         1914
Cys Tyr Lys Glu Ser Val Asp Gln Arg Gly Asn Gln Ile Met Ser Asp
555                 560                 565 aag agg aat gtc atc ctg ttt tct gta ttt gat gag aac cga agc tgg         1962
Lys Arg Asn Val Ile Leu Phe Ser Val Phe Asp Glu Asn Arg Ser Trp
570                 575                 580                 585 tac ctc aca gag aat ata caa cgc ttt ctc ccc aat cca gct gga gtg         2010
Tyr Leu Thr Glu Asn Ile Gln Arg Phe Leu Pro Asn Pro Ala Gly Val
                590                 595                 600 cag ctt gag gat cca gag ttc caa gcc tcc aac atc atg cac agc atc         2058
Gln Leu Glu Asp Pro Glu Phe Gln Ala Ser Asn Ile Met His Ser Ile
                605                 610                 615 aat ggc tat gtt ttt gat agt ttg cag ttg tca gtt tgt ttg cat gag         2106
Asn Gly Tyr Val Phe Asp Ser Leu Gln Leu Ser Val Cys Leu His Glu
                620                 625                 630 gtg gca tac tgg tac att cta agc att gga gca cag act gac ttc ctt         2154
Val Ala Tyr Trp Tyr Ile Leu Ser Ile Gly Ala Gln Thr Asp Phe Leu
635                 640                 645 tct gtc ttc ttc tct gga tat acc ttc aaa cac aaa atg gtc tat gaa         2202
Ser Val Phe Phe Ser Gly Tyr Thr Phe Lys His Lys Met Val Tyr Glu
650                 655                 660                 665 gac aca ctc acc cta ttc cca ttc tca gga gaa act gtc ttc atg tcg         2250
Asp Thr Leu Thr Leu Phe Pro Phe Ser Gly Glu Thr Val Phe Met Ser
                670                 675                 680 atg gaa aac cca ggt cta tgg att ctg ggg tgc cac aac tca gac ttt         2298
Met Glu Asn Pro Gly Leu Trp Ile Leu Gly Cys His Asn Ser Asp Phe
                685                 690                 695 cgg aac aga ggc atg acc gcc tta ctg aag gtt tct agt tgt gac aag         2346
Arg Asn Arg Gly Met Thr Ala Leu Leu Lys Val Ser Ser Cys Asp Lys
                700                 705                 710 aac act ggt gat tat tac gag gac agt tat gaa gat att tca gca tac         2394
Asn Thr Gly Asp Tyr Tyr Glu Asp Ser Tyr Glu Asp Ile Ser Ala Tyr
715                 720                 725 ttg ctg agt aaa aac aat gcc att gaa cca aga agc ttc tcc cag aat         2442
Leu Leu Ser Lys Asn Asn Ala Ile Glu Pro Arg Ser Phe Ser Gln Asn
730                 735                 740                 745 tca aga cac cct agc act agg caa aag caa ttt aat gcc acc aca att         2490
Ser Arg His Pro Ser Thr Arg Gln Lys Gln Phe Asn Ala Thr Thr Ile
                750                 755                 760 cca gaa aat gac ata gag aag act gac cct tgg ttt gca cac aga aca         2538
Pro Glu Asn Asp Ile Glu Lys Thr Asp Pro Trp Phe Ala His Arg Thr
                765                 770                 775 cct atg cct aaa ata caa aat gtc tcc tct agt gat ttg ttg atg ctc         2586
Pro Met Pro Lys Ile Gln Asn Val Ser Ser Ser Asp Leu Leu Met Leu
                780                 785                 790 ttg cga cag agt cct act cca cat ggg cta tcc tta tct gat ctc caa         2634
Leu Arg Gln Ser Pro Thr Pro His Gly Leu Ser Leu Ser Asp Leu Gln
795                 800                 805 gaa gcc aaa tat gag act ttt tct gat gat cca tca cct gga gca ata         2682
Glu Ala Lys Tyr Glu Thr Phe Ser Asp Asp Pro Ser Pro Gly Ala Ile
810                 815                 820                 825 gac agt aat aac agc ctg tct gaa atg aca cac ttc agg cca cag ctc         2730
Asp Ser Asn Asn Ser Leu Ser Glu Met Thr His Phe Arg Pro Gln Leu
                830                 835                 840 cat cac agt ggg gac atg gta ttt acc cct gag tca ggc ctc caa tta         2778
His His Ser Gly Asp Met Val Phe Thr Pro Glu Ser Gly Leu Gln Leu
                845                 850                 855
```

```
aga tta aat gag aaa ctg ggg aca act gca gca aca gag ttg aag aaa      2826
Arg Leu Asn Glu Lys Leu Gly Thr Thr Ala Ala Thr Glu Leu Lys Lys
        860                 865                 870 ctt gat ttc aaa gtt tct agt aca tca aat aat ctg att tca aca att      2874
Leu Asp Phe Lys Val Ser Ser Thr Ser Asn Asn Leu Ile Ser Thr Ile
875                 880                 885 cca tca gac aat ttg gca gca ggt act gat aat aca agt tcc tta gga      2922
Pro Ser Asp Asn Leu Ala Ala Gly Thr Asp Asn Thr Ser Ser Leu Gly
890                 895                 900                 905 ccc cca agt atg cca gtt cat tat gat agt caa tta gat acc act cta      2970
Pro Pro Ser Met Pro Val His Tyr Asp Ser Gln Leu Asp Thr Thr Leu
            910                 915                 920 ttt ggc aaa aag tca tct ccc ctt act gag tct ggt gga cct ctg agc      3018
Phe Gly Lys Lys Ser Ser Pro Leu Thr Glu Ser Gly Gly Pro Leu Ser
        925                 930                 935 ttg agt gaa gaa aat aat gat tca aag ttg tta gaa tca ggt tta atg      3066
Leu Ser Glu Glu Asn Asn Asp Ser Lys Leu Leu Glu Ser Gly Leu Met
        940                 945                 950 aat agc caa gaa agt tca tgg gga aaa aat gta tcg tca aca gag agt      3114
Asn Ser Gln Glu Ser Ser Trp Gly Lys Asn Val Ser Ser Thr Glu Ser
955                 960                 965 ggt agg tta ttt aaa ggg aaa aga gct cat gga cct gct ttg ttg act      3162
Gly Arg Leu Phe Lys Gly Lys Arg Ala His Gly Pro Ala Leu Leu Thr
970                 975                 980                 985 aaa gat aat gcc tta ttc aaa gtt agc atc tct ttg tta aag aca aac      3210
Lys Asp Asn Ala Leu Phe Lys Val Ser Ile Ser Leu Leu Lys Thr Asn
        990                 995                 1000 aaa act tcc aat aat tca gca act aat aga aag act cac att gat ggc      3258
Lys Thr Ser Asn Asn Ser Ala Thr Asn Arg Lys Thr His Ile Asp Gly
        1005                1010                1015 cca tca tta tta att gag aat agt cca tca gtc tgg caa aat ata tta      3306
Pro Ser Leu Leu Ile Glu Asn Ser Pro Ser Val Trp Gln Asn Ile Leu
    1020                1025                1030 gaa agt gac act gag ttt aaa aaa gtg aca cct ttg att cat gac aga      3354
Glu Ser Asp Thr Glu Phe Lys Lys Val Thr Pro Leu Ile His Asp Arg
    1035                1040                1045 atg ctt atg gac aaa aat gct aca gct ttg agg cta aat cat atg tca      3402
Met Leu Met Asp Lys Asn Ala Thr Ala Leu Arg Leu Asn His Met Ser
1050                1055                1060                1065 aat aaa act act tca tca aaa aac atg gaa atg gtc caa cag aaa aaa      3450
Asn Lys Thr Thr Ser Ser Lys Asn Met Glu Met Val Gln Gln Lys Lys
        1070                1075                1080 gag ggc ccc att cca cca gat gca caa aat cca gat atg tcg ttc ttt      3498
Glu Gly Pro Ile Pro Pro Asp Ala Gln Asn Pro Asp Met Ser Phe Phe
        1085                1090                1095 aag atg cta ttc ttg cca gaa tca gca agg tgg ata caa agg act cat      3546
Lys Met Leu Phe Leu Pro Glu Ser Ala Arg Trp Ile Gln Arg Thr His
    1100                1105                1110 gga aag aac tct ctg aac tct ggg caa ggc ccc agt cca aag caa tta      3594
Gly Lys Asn Ser Leu Asn Ser Gly Gln Gly Pro Ser Pro Lys Gln Leu
    1115                1120                1125 gta tcc tta gga cca gaa aaa tct gtg gaa ggt cag aat ttc ttg tct      3642
Val Ser Leu Gly Pro Glu Lys Ser Val Glu Gly Gln Asn Phe Leu Ser
1130                1135                1140                1145 gag aaa aac aaa gtg gta gta gga aag ggt gaa ttt aca aag gac gta      3690
Glu Lys Asn Lys Val Val Val Gly Lys Gly Glu Phe Thr Lys Asp Val
        1150                1155                1160 gga ctc aaa gag atg gtt ttt cca agc agc aga aac cta ttt ctt act      3738
Gly Leu Lys Glu Met Val Phe Pro Ser Ser Arg Asn Leu Phe Leu Thr
    1165                1170                1175
```

```
aac ttg gat aat tta cat gaa aat aat aca cac aat caa gaa aaa aaa      3786
Asn Leu Asp Asn Leu His Glu Asn Asn Thr His Asn Gln Glu Lys Lys
        1180                1185                1190 att cag gaa gaa ata gaa aag aag gaa aca tta atc caa gag aat gta      3834
Ile Gln Glu Glu Ile Glu Lys Lys Glu Thr Leu Ile Gln Glu Asn Val
1195                1200                1205 gtt ttg cct cag ata cat aca gtg act ggc act aag aat ttc atg aag      3882
Val Leu Pro Gln Ile His Thr Val Thr Gly Thr Lys Asn Phe Met Lys
1210                1215                1220                1225 aac ctt ttc tta ctg agc act agg caa aat gta gaa ggt tca tat gag      3930
Asn Leu Phe Leu Leu Ser Thr Arg Gln Asn Val Glu Gly Ser Tyr Glu
            1230                1235                1240 ggg gca tat gct cca gta ctt caa gat ttt agg tca tta aat gat tca      3978
Gly Ala Tyr Ala Pro Val Leu Gln Asp Phe Arg Ser Leu Asn Asp Ser
                1245                1250                1255 aca aat aga aca aag aaa cac aca gct cat ttc tca aaa aaa ggg gag      4026
Thr Asn Arg Thr Lys Lys His Thr Ala His Phe Ser Lys Lys Gly Glu
                    1260                1265                1270 gaa gaa aac ttg gaa ggc ttg gga aat caa acc aag caa att gta gag      4074
Glu Glu Asn Leu Glu Gly Leu Gly Asn Gln Thr Lys Gln Ile Val Glu
        1275                1280                1285 aaa tat gca tgc acc aca agg ata tct cct aat aca agc cag cag aat      4122
Lys Tyr Ala Cys Thr Thr Arg Ile Ser Pro Asn Thr Ser Gln Gln Asn
1290                1295                1300                1305 ttt gtc acg caa cgt agt aag aga gct ttg aaa caa ttc aga ctc cca      4170
Phe Val Thr Gln Arg Ser Lys Arg Ala Leu Lys Gln Phe Arg Leu Pro
            1310                1315                1320 cta gaa gaa aca gaa ctt gaa aaa agg ata att gtg gat gac acc tca      4218
Leu Glu Glu Thr Glu Leu Glu Lys Arg Ile Ile Val Asp Asp Thr Ser
                1325                1330                1335 acc cag tgg tcc aaa aac atg aaa cat ttg acc ccg agc acc ctc aca      4266
Thr Gln Trp Ser Lys Asn Met Lys His Leu Thr Pro Ser Thr Leu Thr
                    1340                1345                1350 cag ata gac tac aat gag aag gag aaa ggg gcc att act cag tct ccc      4314
Gln Ile Asp Tyr Asn Glu Lys Glu Lys Gly Ala Ile Thr Gln Ser Pro
        1355                1360                1365 tta tca gat tgc ctt acg agg agt cat agc atc cct caa gca aat aga      4362
Leu Ser Asp Cys Leu Thr Arg Ser His Ser Ile Pro Gln Ala Asn Arg
1370                1375                1380                1385 tct cca tta ccc att gca aag gta tca tca ttt cca tct att aga cct      4410
Ser Pro Leu Pro Ile Ala Lys Val Ser Ser Phe Pro Ser Ile Arg Pro
            1390                1395                1400 ata tat ctg acc agg gtc cta ttc caa gac aac tct tct cat ctt cca      4458
Ile Tyr Leu Thr Arg Val Leu Phe Gln Asp Asn Ser Ser His Leu Pro
                1405                1410                1415 gca gca tct tat aga aag aaa gat tct ggg gtc caa gaa agc agt cat      4506
Ala Ala Ser Tyr Arg Lys Lys Asp Ser Gly Val Gln Glu Ser Ser His
                    1420                1425                1430 ttc tta caa gga gcc aaa aaa aat aac ctt tct tta gcc att cta acc      4554
Phe Leu Gln Gly Ala Lys Lys Asn Asn Leu Ser Leu Ala Ile Leu Thr
        1435                1440                1445 ttg gag atg act ggt gat caa aga gag gtt ggc tcc ctg ggg aca agt      4602
Leu Glu Met Thr Gly Asp Gln Arg Glu Val Gly Ser Leu Gly Thr Ser
1450                1455                1460                1465 gcc aca aat tca gtc aca tac aag aaa gtt gag aac act gtt ctc ccg      4650
Ala Thr Asn Ser Val Thr Tyr Lys Lys Val Glu Asn Thr Val Leu Pro
            1470                1475                1480 aaa cca gac ttg ccc aaa aca tct ggc aaa gtt gaa ttg ctt cca aaa      4698
Lys Pro Asp Leu Pro Lys Thr Ser Gly Lys Val Glu Leu Leu Pro Lys
```

-continued

```
                1485                1490                1495
gtt cac att tat cag aag gac cta ttc cct acg gaa act agc aat ggg    4746
Val His Ile Tyr Gln Lys Asp Leu Phe Pro Thr Glu Thr Ser Asn Gly
            1500                1505                1510 tct cct ggc cat ctg gat ctc gtg gaa ggg agc ctt ctt cag gga aca    4794
Ser Pro Gly His Leu Asp Leu Val Glu Gly Ser Leu Leu Gln Gly Thr
        1515                1520                1525 gag gga gcg att aag tgg aat gaa gca aac aga cct gga aaa gtt ccc    4842
Glu Gly Ala Ile Lys Trp Asn Glu Ala Asn Arg Pro Gly Lys Val Pro
1530                1535                1540                1545 ttt ctg aga gta gca aca gaa agc tct gca aag act ccc tcc aag cta    4890
Phe Leu Arg Val Ala Thr Glu Ser Ser Ala Lys Thr Pro Ser Lys Leu
                1550                1555                1560 ttg gat cct ctt gct tgg gat aac cac tat ggt act cag ata cca aaa    4938
Leu Asp Pro Leu Ala Trp Asp Asn His Tyr Gly Thr Gln Ile Pro Lys
            1565                1570                1575 gaa gag tgg aaa tcc caa gag aag tca cca gaa aaa aca gct ttt aag    4986
Glu Glu Trp Lys Ser Gln Glu Lys Ser Pro Glu Lys Thr Ala Phe Lys
        1580                1585                1590 aaa aag gat acc att ttg tcc ctg aac gct tgt gaa agc aat cat gca    5034
Lys Lys Asp Thr Ile Leu Ser Leu Asn Ala Cys Glu Ser Asn His Ala
1595                1600                1605 ata gca gca ata aat gag gga caa aat aag ccc gaa ata gaa gtc acc    5082
Ile Ala Ala Ile Asn Glu Gly Gln Asn Lys Pro Glu Ile Glu Val Thr
1610                1615                1620                1625 tgg gca aag caa ggt agg act gaa agg ctg tgc tct caa aac cca cca    5130
Trp Ala Lys Gln Gly Arg Thr Glu Arg Leu Cys Ser Gln Asn Pro Pro
                1630                1635                1640 gtc ttg aaa cgc cat caa cgg gaa ata act cgt act act ctt cag tca    5178
Val Leu Lys Arg His Gln Arg Glu Ile Thr Arg Thr Thr Leu Gln Ser
            1645                1650                1655 gat caa gag gaa att gac tat gat gat acc ata tca gtt gaa atg aag    5226
Asp Gln Glu Glu Ile Asp Tyr Asp Asp Thr Ile Ser Val Glu Met Lys
        1660                1665                1670 aag gaa gat ttt gac att tat gat gag gat gaa aat cag agc ccc cgc    5274
Lys Glu Asp Phe Asp Ile Tyr Asp Glu Asp Glu Asn Gln Ser Pro Arg
    1675                1680                1685 agc ttt caa aag aaa aca cga cac tat ttt att gct gca gtg gag agg    5322
Ser Phe Gln Lys Lys Thr Arg His Tyr Phe Ile Ala Ala Val Glu Arg
1690                1695                1700                1705 ctc tgg gat tat ggg atg agt agc tcc cca cat gtt cta aga aac agg    5370
Leu Trp Asp Tyr Gly Met Ser Ser Ser Pro His Val Leu Arg Asn Arg
                1710                1715                1720 gct cag agt ggc agt gtc cct cag ttc aag aaa gtt gtt ttc cag gaa    5418
Ala Gln Ser Gly Ser Val Pro Gln Phe Lys Lys Val Val Phe Gln Glu
            1725                1730                1735 ttt act gat ggc tcc ttt act cag ccc tta tac cgt gga gaa cta aat    5466
Phe Thr Asp Gly Ser Phe Thr Gln Pro Leu Tyr Arg Gly Glu Leu Asn
        1740                1745                1750 gaa cat ttg gga ctc ctg ggg cca tat ata aga gca gaa gtt gaa gat    5514
Glu His Leu Gly Leu Leu Gly Pro Tyr Ile Arg Ala Glu Val Glu Asp
    1755                1760                1765 aat atc atg gta act ttc aga aat cag gcc tct cgt ccc tat tcc ttc    5562
Asn Ile Met Val Thr Phe Arg Asn Gln Ala Ser Arg Pro Tyr Ser Phe
1770                1775                1780                1785 tat tct agc ctt att tct tat gag gaa gat cag agg caa gga gca gaa    5610
Tyr Ser Ser Leu Ile Ser Tyr Glu Glu Asp Gln Arg Gln Gly Ala Glu
                1790                1795                1800 cct aga aaa aac ttt gtc aag cct aat gaa acc aaa act tac ttt tgg    5658
```

-continued

```
Pro Arg Lys Asn Phe Val Lys Pro Asn Glu Thr Lys Thr Tyr Phe Trp
        1805                1810                1815 aaa gtg caa cat cat atg gca ccc act aaa gat gag ttt gac tgc aaa      5706
Lys Val Gln His His Met Ala Pro Thr Lys Asp Glu Phe Asp Cys Lys
    1820                1825                1830 gcc tgg gct tat ttc tct gat gtt gac ctg gaa aaa gat gtg cac tca      5754
Ala Trp Ala Tyr Phe Ser Asp Val Asp Leu Glu Lys Asp Val His Ser
1835                1840                1845 ggc ctg att gga ccc ctt ctg gtc tgc cac act aac aca ctg aac cct      5802
Gly Leu Ile Gly Pro Leu Leu Val Cys His Thr Asn Thr Leu Asn Pro
1850                1855                1860                1865 gct cat ggg aga caa gtg aca gta cag gaa ttt gct ctg ttt ttc acc      5850
Ala His Gly Arg Gln Val Thr Val Gln Glu Phe Ala Leu Phe Phe Thr
        1870                1875                1880 atc ttt gat gag acc aaa agc tgg tac ttc act gaa aat atg gaa aga      5898
Ile Phe Asp Glu Thr Lys Ser Trp Tyr Phe Thr Glu Asn Met Glu Arg
    1885                1890                1895 aac tgc agg gct ccc tgc aat atc cag atg gaa gat ccc act ttt aaa      5946
Asn Cys Arg Ala Pro Cys Asn Ile Gln Met Glu Asp Pro Thr Phe Lys
1900                1905                1910 gag aat tat cgc ttc cat gca atc aat ggc tac ata atg gat aca cta      5994
Glu Asn Tyr Arg Phe His Ala Ile Asn Gly Tyr Ile Met Asp Thr Leu
    1915                1920                1925 cct ggc tta gta atg gct cag gat caa agg att cga tgg tat ctg ctc      6042
Pro Gly Leu Val Met Ala Gln Asp Gln Arg Ile Arg Trp Tyr Leu Leu
1930                1935                1940                1945 agc atg ggc agc aat gaa aac atc cat tct att cat ttc agt gga cat      6090
Ser Met Gly Ser Asn Glu Asn Ile His Ser Ile His Phe Ser Gly His
                1950                1955                1960 gtg ttc act gta cga aaa aaa gag gag tat aaa atg gca ctg tac aat      6138
Val Phe Thr Val Arg Lys Lys Glu Glu Tyr Lys Met Ala Leu Tyr Asn
        1965                1970                1975 ctc tat cca ggt gtt ttt gag aca gtg gaa atg tta cca tcc aaa gct      6186
Leu Tyr Pro Gly Val Phe Glu Thr Val Glu Met Leu Pro Ser Lys Ala
    1980                1985                1990 gga att tgg cgg gtg gaa tgc ctt att ggc gag cat cta cat gct ggg      6234
Gly Ile Trp Arg Val Glu Cys Leu Ile Gly Glu His Leu His Ala Gly
1995                2000                2005 atg agc aca ctt ttt ctg gtg tac agc aat aag tgt cag act ccc ctg      6282
Met Ser Thr Leu Phe Leu Val Tyr Ser Asn Lys Cys Gln Thr Pro Leu
2010                2015                2020                2025 gga atg gct tct gga cac att aga gat ttt cag att aca gct tca gga      6330
Gly Met Ala Ser Gly His Ile Arg Asp Phe Gln Ile Thr Ala Ser Gly
                2030                2035                2040 caa tat gga cag tgg gcc cca aag ctg gcc aga ctt cat tat tcc gga      6378
Gln Tyr Gly Gln Trp Ala Pro Lys Leu Ala Arg Leu His Tyr Ser Gly
        2045                2050                2055 tca atc aat gcc tgg agc acc aag gag ccc ttt tct tgg atc aag gtg      6426
Ser Ile Asn Ala Trp Ser Thr Lys Glu Pro Phe Ser Trp Ile Lys Val
    2060                2065                2070 gat ctg ttg gca cca atg att att cac ggc atc aag acc cag ggt gcc      6474
Asp Leu Leu Ala Pro Met Ile Ile His Gly Ile Lys Thr Gln Gly Ala
2075                2080                2085 cgt cag aag ttc tcc agc ctc tac atc tct cag ttt atc atc atg tat      6522
Arg Gln Lys Phe Ser Ser Leu Tyr Ile Ser Gln Phe Ile Ile Met Tyr
2090                2095                2100                2105 agt ctt gat ggg aag aag tgg cag act tat cga gga aat tcc act gga      6570
Ser Leu Asp Gly Lys Lys Trp Gln Thr Tyr Arg Gly Asn Ser Thr Gly
                2110                2115                2120
```

-continued

| | |
|---|---|
| acc tta atg gtc ttc ttt ggc aat gtg gat tca tct ggg ata aaa cac<br>Thr Leu Met Val Phe Phe Gly Asn Val Asp Ser Ser Gly Ile Lys His<br>        2125                2130                     2135 | 6618 |
| aat att ttt aac cct cca att att gct cga tac atc cgt ttg cac cca<br>Asn Ile Phe Asn Pro Pro Ile Ile Ala Arg Tyr Ile Arg Leu His Pro<br>    2140                     2145                      2150 | 6666 |
| act cat tat agc att cgc agc act ctt cgc atg gag ttg atg ggc tgt<br>Thr His Tyr Ser Ile Arg Ser Thr Leu Arg Met Glu Leu Met Gly Cys<br>        2155                2160                     2165 | 6714 |
| gat tta aat agt tgc agc atg cca ttg gga atg gag agt aaa gca ata<br>Asp Leu Asn Ser Cys Ser Met Pro Leu Gly Met Glu Ser Lys Ala Ile<br>2170                 2175                   2180                    2185 | 6762 |
| tca gat gca cag att act gct tca tcc tac ttt acc aat atg ttt gcc<br>Ser Asp Ala Gln Ile Thr Ala Ser Ser Tyr Phe Thr Asn Met Phe Ala<br>    2190                     2195                      2200 | 6810 |
| acc tgg tct cct tca aaa gct cga ctt cac ctc caa ggg agg agt aat<br>Thr Trp Ser Pro Ser Lys Ala Arg Leu His Leu Gln Gly Arg Ser Asn<br>        2205                2210                     2215 | 6858 |
| gcc tgg aga cct cag gtg aat aat cca aaa gag tgg ctg caa gtg gac<br>Ala Trp Arg Pro Gln Val Asn Asn Pro Lys Glu Trp Leu Gln Val Asp<br>2220                 2225                   2230 | 6906 |
| ttc cag aag aca atg aaa gtc aca gga gta act act cag gga gta aaa<br>Phe Gln Lys Thr Met Lys Val Thr Gly Val Thr Thr Gln Gly Val Lys<br>    2235                     2240                     2245 | 6954 |
| tct ctg ctt acc agc atg tat gtg aag gag ttc ctc atc tcc agc agt<br>Ser Leu Leu Thr Ser Met Tyr Val Lys Glu Phe Leu Ile Ser Ser Ser<br>2250                 2255                   2260                    2265 | 7002 |
| caa gat ggc cat cag tgg act ctc ttt ttt cag aat ggc aaa gta aag<br>Gln Asp Gly His Gln Trp Thr Leu Phe Phe Gln Asn Gly Lys Val Lys<br>        2270                2275                     2280 | 7050 |
| gtt ttt cag gga aat caa gac tcc ttc aca cct gtg gtg aac tct cta<br>Val Phe Gln Gly Asn Gln Asp Ser Phe Thr Pro Val Val Asn Ser Leu<br>    2285                     2290                     2295 | 7098 |
| gac cca ccg tta ctg act cgc tac ctt cga att cac ccc cag agt tgg<br>Asp Pro Pro Leu Leu Thr Arg Tyr Leu Arg Ile His Pro Gln Ser Trp<br>2300                 2305                    2310 | 7146 |
| gtg cac cag att gcc ctg agg atg gag gtt ctg ggc tgc gag gca cag<br>Val His Gln Ile Ala Leu Arg Met Glu Val Leu Gly Cys Glu Ala Gln<br>    2315                     2320                     2325 | 7194 |
| gac ctc tac tgagggtggc cactgcagca cctgccactg ccgtcacctc<br>Asp Leu Tyr<br>2330 | 7243 |
| tccctcctca gctccagggc agtgtccctc cctggcttgc cttctacctt tgtgctaaat | 7303 |
| cctagcagac actgccttga agcctcctga attaactatc atcagtcctg catttctttg | 7363 |
| gtgggggggcc aggagggtgc atccaattta acttaactct tacctatttt ctgcagctgc | 7423 |
| tcccagatta ctccttcctt ccaatataac taggcaaaaa gaagtgagga gaaacctgca | 7483 |
| tgaaagcatt cttccctgaa aagttaggcc tctcagagtc accacttcct ctgttgtaga | 7543 |
| aaaactatgt gatgaaactt tgaaaaagat atttatgatg ttaacatttc aggttaagcc | 7603 |
| tcatacgttt aaaataaaac tctcagttgt ttattatcct gatcaagcat ggaacaaagc | 7663 |
| atgtttcagg atcagatcaa tacaatcttg gagtcaaaag gcaaatcatt tggacaatct | 7723 |
| gcaaaatgga gagaatacaa taactactac agtaaagtct gtttctgctt ccttacacat | 7783 |
| agatataatt atgttatttta gtcattatga ggggcacatt cttatctcca aaactagcat | 7843 |
| tcttaaactg agaattatag atggggttca agaatcccta agtcccctga aattatataa | 7903 |
| ggcattctgt ataaatgcaa atgtgcattt ttctgacgag tgtccataga tataaagcca | 7963 |

```
ttggtcttaa ttctgaccaa taaaaaaata agtcaggagg atgcaattgt tgaaagcttt    8023
gaaataaaat aacatgtctt cttgaaattt gtgatggcca agaaagaaaa tgatgatgac    8083
attaggcttc taaaggacat acatttaata tttctgtgga aatatgagga aaatccatgg    8143
ttatctgaga taggagatac aaactttgta attctaataa tgcactcagt ttactctctc    8203
cctctactaa tttcctgctg aaaataacac aacaaaaatg taacagggga aattatatac    8263
cgtgactgaa aactagagtc ctacttacat agttgaaata tcaaggaggt cagaagaaaa    8323
ttggactggt gaaaacagaa aaaacactcc agtctgccat atcaccacac aataggatcc    8383
cccttcttgc cctccacccc cataagattg tgaagggttt actgctcctt ccatctgcct    8443
gcaccccttc actatgacta cacagaactc tcctgatagt aaaggggget ggaggcaagg    8503 ataagttata gagcagttgg aggaagcatc caaagactgc aacccagggc aaatggaaaa    8563
caggagatcc taatatgaaa gaaaatgga tcccaatctg agaaaaggca aaagaatggc    8623 tactttttc tatgctggag tattttctaa taatcctgct tgacccttat ctgacctctt    8683
tggaaactat aacatagctg tcacagtata gtcacaatcc acaaatgatg caggtgcaaa    8743
tggtttatag ccctgtgaag ttcttaaagt ttagaggcta acttacagaa atgaataagt    8803
tgttttgttt tatagcccgg tagaggagtt aaccccaaag gtgatatggt tttatttcct    8863
gttatgttta acttgataat cttatttttgg cattcttttc ccattgacta tatacatctc    8923
tatttctcaa atgttcatgg aactagctct tttattttcc tgctggtttc ttcagtaatg    8983
agttaaataa aacattgaca cataca                                        9009
```

<210> SEQ ID NO 2
<211> LENGTH: 2332
<212> TYPE: PRT
<213> ORGANISM: Homo sapiens

<400> SEQUENCE: 2

```
Ala Thr Arg Arg Tyr Tyr Leu Gly Ala Val Glu Leu Ser Trp Asp Tyr
  1               5                  10                  15

Met Gln Ser Asp Leu Gly Glu Leu Pro Val Asp Ala Arg Phe Pro Pro
                 20                  25                  30

Arg Val Pro Lys Ser Phe Pro Phe Asn Thr Ser Val Val Tyr Lys Lys
             35                  40                  45

Thr Leu Phe Val Glu Phe Thr Val His Leu Phe Asn Ile Ala Lys Pro
         50                  55                  60

Arg Pro Pro Trp Met Gly Leu Leu Gly Pro Thr Ile Gln Ala Glu Val
     65                  70                  75                  80

Tyr Asp Thr Val Val Ile Thr Leu Lys Asn Met Ala Ser His Pro Val
                     85                  90                  95

Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
        130                 135                 140

Gly Pro Met Ala Ser Asp Pro Leu Cys Leu Thr Tyr Ser Tyr Leu Ser
    145                 150                 155                 160

His Val Asp Leu Val Lys Asp Leu Asn Ser Gly Leu Ile Gly Ala Leu
                    165                 170                 175

Leu Val Cys Arg Glu Gly Ser Leu Ala Lys Glu Lys Thr Gln Thr Leu
```

-continued

```
                180                 185                 190
His Lys Phe Ile Leu Phe Ala Val Phe Asp Glu Gly Lys Ser Trp
            195                 200                 205
His Ser Glu Thr Lys Asn Ser Leu Met Gln Asp Arg Asp Ala Ala Ser
    210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
                260                 265                 270
Gly His Thr Phe Leu Val Arg Asn His Arg Gln Ala Ser Leu Glu Ile
            275                 280                 285
Ser Pro Ile Thr Phe Leu Thr Ala Gln Thr Leu Leu Met Asp Leu Gly
            290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Asp Leu Thr Asp
                340                 345                 350
Ser Glu Met Asp Val Val Arg Phe Asp Asp Asp Asn Ser Pro Ser Phe
            355                 360                 365
Ile Gln Ile Arg Ser Val Ala Lys Lys His Pro Lys Thr Trp Val His
            370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
                420                 425                 430
Asp Glu Thr Phe Lys Thr Arg Glu Ala Ile Gln His Glu Ser Gly Ile
            435                 440                 445
Leu Gly Pro Leu Leu Tyr Gly Glu Val Gly Asp Thr Leu Leu Ile Ile
    450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
            515                 520                 525
Leu Thr Arg Tyr Tyr Ser Ser Phe Val Asn Met Glu Arg Asp Leu Ala
    530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
    595                 600                 605
```

```
Gln Ala Ser Asn Ile Met His Ser Ile Asn Gly Tyr Val Phe Asp Ser
    610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Ser Gly Tyr
                645                 650                 655
Thr Phe Lys His Lys Met Val Tyr Glu Asp Thr Leu Thr Leu Phe Pro
                660                 665                 670
Phe Ser Gly Glu Thr Val Phe Met Ser Met Glu Asn Pro Gly Leu Trp
            675                 680                 685
Ile Leu Gly Cys His Asn Ser Asp Phe Arg Asn Arg Gly Met Thr Ala
            690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Ser Arg His Pro Ser Thr Arg
                740                 745                 750
Gln Lys Gln Phe Asn Ala Thr Thr Ile Pro Glu Asn Asp Ile Glu Lys
                755                 760                 765
Thr Asp Pro Trp Phe Ala His Arg Thr Pro Met Pro Lys Ile Gln Asn
770                 775                 780
Val Ser Ser Ser Asp Leu Leu Met Leu Leu Arg Gln Ser Pro Thr Pro
785                 790                 795                 800
His Gly Leu Ser Leu Ser Asp Leu Gln Glu Ala Lys Tyr Glu Thr Phe
                805                 810                 815
Ser Asp Asp Pro Ser Pro Gly Ala Ile Asp Ser Asn Asn Ser Leu Ser
                820                 825                 830
Glu Met Thr His Phe Arg Pro Gln Leu His His Ser Gly Asp Met Val
        835                 840                 845
Phe Thr Pro Glu Ser Gly Leu Gln Leu Arg Leu Asn Glu Lys Leu Gly
850                 855                 860
Thr Thr Ala Ala Thr Glu Leu Lys Lys Leu Asp Phe Lys Val Ser Ser
865                 870                 875                 880
Thr Ser Asn Asn Leu Ile Ser Thr Ile Pro Ser Asp Asn Leu Ala Ala
                885                 890                 895
Gly Thr Asp Asn Thr Ser Ser Leu Gly Pro Pro Ser Met Pro Val His
            900                 905                 910
Tyr Asp Ser Gln Leu Asp Thr Thr Leu Phe Gly Lys Lys Ser Ser Pro
        915                 920                 925
Leu Thr Glu Ser Gly Gly Pro Leu Ser Leu Ser Glu Glu Asn Asn Asp
930                 935                 940
Ser Lys Leu Leu Glu Ser Gly Leu Met Asn Ser Gln Glu Ser Ser Trp
945                 950                 955                 960
Gly Lys Asn Val Ser Ser Thr Glu Ser Gly Arg Leu Phe Lys Gly Lys
                965                 970                 975
Arg Ala His Gly Pro Ala Leu Leu Thr Lys Asp Asn Ala Leu Phe Lys
            980                 985                 990
Val Ser Ile Ser Leu Leu Lys Thr Asn Lys Thr Ser Asn Asn Ser Ala
                995                 1000                1005
Thr Asn Arg Lys Thr His Ile Asp Gly Pro Ser Leu Leu Ile Glu Asn
    1010                1015                1020
```

```
Ser Pro Ser Val Trp Gln Asn Ile Leu Glu Ser Asp Thr Glu Phe Lys
025            1030            1035            1040

Lys Val Thr Pro Leu Ile His Asp Arg Met Leu Met Asp Lys Asn Ala
        1045            1050            1055

Thr Ala Leu Arg Leu Asn His Met Ser Asn Lys Thr Thr Ser Ser Lys
        1060            1065            1070

Asn Met Glu Met Val Gln Gln Lys Lys Glu Gly Pro Ile Pro Pro Asp
    1075            1080            1085

Ala Gln Asn Pro Asp Met Ser Phe Phe Lys Met Leu Phe Leu Pro Glu
    1090            1095            1100

Ser Ala Arg Trp Ile Gln Arg Thr His Gly Lys Asn Ser Leu Asn Ser
105            1110            1115            1120

Gly Gln Gly Pro Ser Pro Lys Gln Leu Val Ser Leu Gly Pro Glu Lys
        1125            1130            1135

Ser Val Glu Gly Gln Asn Phe Leu Ser Glu Lys Asn Lys Val Val Val
        1140            1145            1150

Gly Lys Gly Glu Phe Thr Lys Asp Val Gly Leu Lys Glu Met Val Phe
        1155            1160            1165

Pro Ser Ser Arg Asn Leu Phe Leu Thr Asn Leu Asp Asn Leu His Glu
    1170            1175            1180

Asn Asn Thr His Asn Gln Glu Lys Lys Ile Gln Glu Ile Glu Lys
185            1190            1195            1200

Lys Glu Thr Leu Ile Gln Glu Asn Val Val Leu Pro Gln Ile His Thr
        1205            1210            1215

Val Thr Gly Thr Lys Asn Phe Met Lys Asn Leu Phe Leu Leu Ser Thr
        1220            1225            1230

Arg Gln Asn Val Glu Gly Ser Tyr Glu Gly Ala Tyr Ala Pro Val Leu
        1235            1240            1245

Gln Asp Phe Arg Ser Leu Asn Asp Ser Thr Asn Arg Thr Lys Lys His
    1250            1255            1260

Thr Ala His Phe Ser Lys Lys Gly Glu Glu Asn Leu Glu Gly Leu
265            1270            1275            1280

Gly Asn Gln Thr Lys Gln Ile Val Glu Lys Tyr Ala Cys Thr Thr Arg
        1285            1290            1295

Ile Ser Pro Asn Thr Ser Gln Gln Asn Phe Val Thr Gln Arg Ser Lys
        1300            1305            1310

Arg Ala Leu Lys Gln Phe Arg Leu Pro Leu Glu Glu Thr Glu Leu Glu
    1315            1320            1325

Lys Arg Ile Ile Val Asp Asp Thr Ser Thr Gln Trp Ser Lys Asn Met
        1330            1335            1340

Lys His Leu Thr Pro Ser Thr Leu Thr Gln Ile Asp Tyr Asn Glu Lys
345            1350            1355            1360

Glu Lys Gly Ala Ile Thr Gln Ser Pro Leu Ser Asp Cys Leu Thr Arg
        1365            1370            1375

Ser His Ser Ile Pro Gln Ala Asn Arg Ser Pro Leu Pro Ile Ala Lys
        1380            1385            1390

Val Ser Ser Phe Pro Ser Ile Arg Pro Ile Tyr Leu Thr Arg Val Leu
        1395            1400            1405

Phe Gln Asp Asn Ser Ser His Leu Pro Ala Ala Ser Tyr Arg Lys Lys
    1410            1415            1420

Asp Ser Gly Val Gln Glu Ser Ser His Phe Leu Gln Gly Ala Lys Lys
425            1430            1435            1440

Asn Asn Leu Ser Leu Ala Ile Leu Thr Leu Glu Met Thr Gly Asp Gln
```

-continued

Arg Glu Val Gly Ser Leu Gly Thr Ser Ala Thr Asn Ser Val Thr Tyr
        1445                1450                1455
Lys Lys Val Glu Asn Thr Val Leu Pro Lys Pro Asp Leu Pro Lys Thr
    1460                1465                1470
Ser Gly Lys Val Glu Leu Leu Pro Lys Val His Ile Tyr Gln Lys Asp
1475                1480                1485
Leu Phe Pro Thr Glu Thr Ser Asn Gly Ser Pro Gly His Leu Asp Leu
    1490                1495                1500
Val Glu Gly Ser Leu Leu Gln Gly Thr Glu Gly Ala Ile Lys Trp Asn
505                1510                1515                1520
Glu Ala Asn Arg Pro Gly Lys Val Pro Phe Leu Arg Val Ala Thr Glu
    1525                1530                1535
Ser Ser Ala Lys Thr Pro Ser Lys Leu Leu Asp Pro Leu Ala Trp Asp
        1540                1545                1550
Asn His Tyr Gly Thr Gln Ile Pro Lys Glu Glu Trp Lys Ser Gln Glu
    1555                1560                1565
Lys Ser Pro Glu Lys Thr Ala Phe Lys Lys Asp Thr Ile Leu Ser
        1570                1575                1580
Leu Asn Ala Cys Glu Ser Asn His Ala Ile Ala Ala Ile Asn Glu Gly
585                1590                1595                1600
Gln Asn Lys Pro Glu Ile Glu Val Thr Trp Ala Lys Gln Gly Arg Thr
    1605                1610                1615
Glu Arg Leu Cys Ser Gln Asn Pro Pro Val Leu Lys Arg His Gln Arg
        1620                1625                1630
Glu Ile Thr Arg Thr Thr Leu Gln Ser Asp Gln Glu Glu Ile Asp Tyr
    1635                1640                1645
Asp Asp Thr Ile Ser Val Glu Met Lys Lys Glu Asp Phe Asp Ile Tyr
665                1650                1655                1660
Asp Glu Asp Glu Asn Gln Ser Pro Arg Ser Phe Gln Lys Lys Thr Arg
        1665                1670                1675                1680
His Tyr Phe Ile Ala Ala Val Glu Arg Leu Trp Asp Tyr Gly Met Ser
    1685                1690                1695
Ser Ser Pro His Val Leu Arg Asn Arg Ala Gln Ser Gly Ser Val Pro
        1700                1705                1710
Gln Phe Lys Lys Val Val Phe Gln Glu Phe Thr Asp Gly Ser Phe Thr
    1715                1720                1725
Gln Pro Leu Tyr Arg Gly Glu Leu Asn Glu His Leu Gly Leu Leu Gly
745                1730                1735                1740
Pro Tyr Ile Arg Ala Glu Val Glu Asp Asn Ile Met Val Thr Phe Arg
    1745                1750                1755                1760
Asn Gln Ala Ser Arg Pro Tyr Ser Phe Tyr Ser Ser Leu Ile Ser Tyr
        1765                1770                1775
Glu Glu Asp Gln Arg Gln Gly Ala Glu Pro Arg Lys Asn Phe Val Lys
    1780                1785                1790
Pro Asn Glu Thr Lys Thr Tyr Phe Trp Lys Val Gln His His Met Ala
        1795                1800                1805
Pro Thr Lys Asp Glu Phe Asp Cys Lys Ala Trp Ala Tyr Phe Ser Asp
825                1810                1815                1820
Val Asp Leu Glu Lys Asp Val His Ser Gly Leu Ile Gly Pro Leu Leu
    1825                1830                1835                1840
Val Cys His Thr Asn Thr Leu Asn Pro Ala His Gly Arg Gln Val Thr
        1845                1850                1855
                            1860                1865                1870

```
Val Gln Glu Phe Ala Leu Phe Phe Thr Ile Phe Asp Glu Thr Lys Ser
    1875                1880                1885

Trp Tyr Phe Thr Glu Asn Met Glu Arg Asn Cys Arg Ala Pro Cys Asn
    1890                1895                1900

Ile Gln Met Glu Asp Pro Thr Phe Lys Glu Asn Tyr Arg Phe His Ala
905                 1910                1915                1920

Ile Asn Gly Tyr Ile Met Asp Thr Leu Pro Gly Leu Val Met Ala Gln
                1925                1930                1935

Asp Gln Arg Ile Arg Trp Tyr Leu Leu Ser Met Gly Ser Asn Glu Asn
            1940                1945                1950

Ile His Ser Ile His Phe Ser Gly His Val Phe Thr Val Arg Lys Lys
            1955                1960                1965

Glu Glu Tyr Lys Met Ala Leu Tyr Asn Leu Tyr Pro Gly Val Phe Glu
    1970                1975                1980

Thr Val Glu Met Leu Pro Ser Lys Ala Gly Ile Trp Arg Val Glu Cys
985                 1990                1995                2000

Leu Ile Gly Glu His Leu His Ala Gly Met Ser Thr Leu Phe Leu Val
                2005                2010                2015

Tyr Ser Asn Lys Cys Gln Thr Pro Leu Gly Met Ala Ser Gly His Ile
            2020                2025                2030

Arg Asp Phe Gln Ile Thr Ala Ser Gly Gln Tyr Gly Gln Trp Ala Pro
    2035                2040                2045

Lys Leu Ala Arg Leu His Tyr Ser Gly Ser Ile Asn Ala Trp Ser Thr
    2050                2055                2060

Lys Glu Pro Phe Ser Trp Ile Lys Val Asp Leu Leu Ala Pro Met Ile
065                 2070                2075                2080

Ile His Gly Ile Lys Thr Gln Gly Ala Arg Gln Lys Phe Ser Ser Leu
            2085                2090                2095

Tyr Ile Ser Gln Phe Ile Ile Met Tyr Ser Leu Asp Gly Lys Lys Trp
            2100                2105                2110

Gln Thr Tyr Arg Gly Asn Ser Thr Gly Thr Leu Met Val Phe Phe Gly
    2115                2120                2125

Asn Val Asp Ser Ser Gly Ile Lys His Asn Ile Phe Asn Pro Pro Ile
    2130                2135                2140

Ile Ala Arg Tyr Ile Arg Leu His Pro Thr His Tyr Ser Ile Arg Ser
145                 2150                2155                2160

Thr Leu Arg Met Glu Leu Met Gly Cys Asp Leu Asn Ser Cys Ser Met
                2165                2170                2175

Pro Leu Gly Met Glu Ser Lys Ala Ile Ser Asp Ala Gln Ile Thr Ala
            2180                2185                2190

Ser Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val Asn
    2210                2215                2220

Asn Pro Lys Glu Trp Leu Gln Val Asp Phe Gln Lys Thr Met Lys Val
225                 2230                2235                2240

Thr Gly Val Thr Thr Gln Gly Val Lys Ser Leu Leu Thr Ser Met Tyr
                2245                2250                2255

Val Lys Glu Phe Leu Ile Ser Ser Ser Gln Asp Gly His Gln Trp Thr
            2260                2265                2270

Leu Phe Phe Gln Asn Gly Lys Val Lys Val Phe Gln Gly Asn Gln Asp
    2275                2280                2285
```

```
Ser Phe Thr Pro Val Val Asn Ser Leu Asp Pro Leu Leu Thr Arg
    2290                2295                2300

Tyr Leu Arg Ile His Pro Gln Ser Trp Val His Gln Ile Ala Leu Arg
305                 2310                2315                2320

Met Glu Val Leu Gly Cys Glu Ala Gln Asp Leu Tyr
                2325                2330

<210> SEQ ID NO 3
<211> LENGTH: 1130
<212> TYPE: DNA
<213> ORGANISM: Porcine

<400> SEQUENCE: 3
taagcaccct aagacgtggg tgcactacat ctctgcagag gaggaggact gggactacgc    60
ccccgcggtc cccagcccca gtgacagaag ttataaaagt ctctacttga acagtggtcc   120
tcagcgaatt ggtaggaaat acaaaaaagc tcgattcgtc gcttacacgg atgtaacatt   180
taagactcgt aaagctattc cgtatgaatc aggaatcctg gacctttac tttatggaga    240
agttggagac acacttttga ttatatttaa aataaagcg agccgaccat ataacatcta    300
ccctcatgga atcactgatg tcagcgcttt gcacccaggg agacttctaa aaggttggaa    360
acatttgaaa gacatgccaa ttctgccagg agagactttc aagtataaat ggacagtgac    420
tgtggaagat gggccaacca agtccgatcc tcggtgcctg acccgctact actcgagctc    480
cattaatcta gagaaagatc tggcttcggg actcattggc cctctcctca tctgctacaa    540
agaatctgta gaccaaagag gaaaccagat gatgtcagac aagagaaacg tcatcctgtt    600
ttctgtattc gatgagaatc aaagctggta cctcgcagag aatattcagc gcttcctccc    660
caatccggat ggattacagc cccaggatcc agagttccaa gcttctaaca tcatgcacag    720
catcaatggc tatgttttg atagcttgca gctgtcggtt tgtttgcacg aggtggcata    780
ctggtacatt ctaagtgttg gagcacagac ggacttcctc tccgtcttct tctctggcta    840
cacccttcaaa cacaaaatgg tctatgaaga cacactcacc ctgttcccct tctcaggaga    900
aacggtcttc atgtcaatgg aaaacccagg tctctgggtc ctagggtgcc acaactcaga    960
cttgcggaac agagggatga cagccttact gaaggtgtat agttgtgaca gggacattgg   1020
tgattattat gacaacactt atgaagatat tccaggcttc ttgctgagtg gaaagaatgt   1080
cattgaaccc agaagctttg cccagaattc aagacccccct agtgcgagca              1130

<210> SEQ ID NO 4
<211> LENGTH: 368
<212> TYPE: PRT
<213> ORGANISM: Porcine

<400> SEQUENCE: 4

Ser Val Ala Lys Lys His Pro Lys Thr Trp Val His Tyr Ile Ser Ala
  1               5                  10                  15

Glu Glu Glu Asp Trp Asp Tyr Ala Pro Ala Val Pro Ser Pro Ser Asp
             20                  25                  30

Arg Ser Tyr Lys Ser Leu Tyr Leu Asn Ser Gly Pro Gln Arg Ile Gly
         35                  40                  45

Arg Lys Tyr Lys Lys Ala Arg Phe Val Ala Tyr Thr Asp Val Thr Phe
     50                  55                  60

Lys Thr Arg Lys Ala Ile Pro Tyr Glu Ser Gly Ile Leu Gly Pro Leu
 65                  70                  75                  80

Leu Tyr Gly Glu Val Gly Asp Thr Leu Leu Ile Ile Phe Lys Asn Lys
```

-continued

```
                85                  90                  95
Ala Ser Arg Pro Tyr Asn Ile Tyr Pro His Gly Ile Thr Asp Val Ser
               100                 105                 110
Ala Leu His Pro Gly Arg Leu Leu Lys Gly Trp Lys His Leu Lys Asp
           115                 120                 125
Met Pro Ile Leu Pro Gly Glu Thr Phe Lys Tyr Lys Trp Thr Val Thr
       130                 135                 140
Val Glu Asp Gly Pro Thr Lys Ser Asp Pro Arg Cys Leu Thr Arg Tyr
145                 150                 155                 160
Tyr Ser Ser Ser Ile Asn Leu Glu Lys Asp Leu Ala Ser Gly Leu Ile
               165                 170                 175
Gly Pro Leu Leu Ile Cys Tyr Lys Glu Ser Val Asp Gln Arg Gly Asn
           180                 185                 190
Gln Met Met Ser Asp Lys Arg Asn Val Ile Leu Phe Ser Val Phe Asp
       195                 200                 205
Glu Asn Gln Ser Trp Tyr Leu Ala Glu Asn Ile Gln Arg Phe Leu Pro
   210                 215                 220
Asn Pro Asp Gly Leu Gln Pro Gln Asp Pro Glu Phe Gln Ala Ser Asn
225                 230                 235                 240
Ile Met His Ser Ile Asn Gly Tyr Val Phe Asp Ser Leu Gln Leu Ser
               245                 250                 255
Val Cys Leu His Glu Val Ala Tyr Trp Tyr Ile Leu Ser Val Gly Ala
           260                 265                 270
Gln Thr Asp Phe Leu Ser Val Phe Phe Ser Gly Tyr Thr Phe Lys His
       275                 280                 285
Lys Met Val Tyr Glu Asp Thr Leu Thr Leu Phe Pro Phe Ser Gly Glu
   290                 295                 300
Thr Val Phe Met Ser Met Glu Asn Pro Gly Leu Trp Val Leu Gly Cys
305                 310                 315                 320
His Asn Ser Asp Leu Arg Asn Arg Gly Met Thr Ala Leu Leu Lys Val
               325                 330                 335
Tyr Ser Cys Asp Arg Asp Ile Gly Asp Tyr Tyr Asp Asn Thr Tyr Glu
           340                 345                 350
Asp Ile Pro Gly Phe Leu Leu Ser Gly Lys Asn Val Ile Glu Pro Arg
       355                 360                 365
```

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 5
ctaatacgac tcactatagg gctcgagcgg ccgcccgggc aggt                    44

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 6 catcctaat acgactcact atagggc                                        27

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 7
ccattgacat gaagaccgtt tctc                                    24

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 8
actcactata gggctcgagc ggc                                     23

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 9
gggtgcaaag cgctgacatc agtg                                    24

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 10
cctctcgagc caccatgtcg agccaccatg cagctagagc tctccacctg        50

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 11
cgcgcggccg cgcatctggc aaagctgagt t                            31

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: oligonucleotide primer
<220> FEATURE:
<221> NAME/KEY: misc_feature
<222> LOCATION: (25)
<223> OTHER INFORMATION: At position 25, r is a or g.

<400> SEQUENCE: 12

```
gaaataagcc caggctttgc agtcraa                                                27
```

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer
<220> FEATURE:
<221> NAME/KEY: misc_feature
<222> LOCATION: (22)
<223> OTHER INFORMATION: At position 22, n is a, g, c or t.

<400> SEQUENCE: 13

```
aggaaattcc actggaacct tn                                                     22
```

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer
<220> FEATURE:
<221> NAME/KEY: misc_feature
<222> LOCATION: (25)
<223> OTHER INFORMATION: At position 25, n is a, g, c or t.

<400> SEQUENCE: 14

```
ctgggggtga attcgaaggt agcgn                                                  25
```

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 15

```
gagttcatcg ggaagacctg ttg                                                    23
```

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 16

```
acagcccatc aactccatgc gaag                                                   24
```

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 17

```
tcagggcaat caggactcc                                                         19
```

<210> SEQ ID NO 18
<211> LENGTH: 21

```
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 18
ccgtggtgaa cgctctggac c                                             21

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 19
gtagaggtcc tgtgcctcgc agcc                                          24

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence:
      oligonucleotide primer
<220> FEATURE:
<221> NAME/KEY: misc_feature
<222> LOCATION: (7)..(25)
<223> OTHER INFORMATION: S is g or c, k is g or t, r is a or g, and y is
      c or t.

<400> SEQUENCE: 20
gtagagstsc tgkgcctcrc akccyag                                       27

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 21
cttcgcatgg agttgatggg ctgt                                          24

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 22
aatcaggact cctccacccc cg                                            22

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 23
ggatccaccc cacgagctgg                                               20
```

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 24
cgccctgagg ctcgaggttc tagg         24

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 25
aatcaggact cctccacccc cg           22

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 26
ccttgcagga attcgattca              20

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 27
ccgtggtgaa cgctctggac c            21

<210> SEQ ID NO 28
<211> LENGTH: 2319
<212> TYPE: PRT
<213> ORGANISM: Mus musculus

<400> SEQUENCE: 28

Met Gln Ile Ala Leu Phe Ala Cys Phe Phe Leu Ser Leu Phe Asn Phe
 1               5                  10                  15

Cys Ser Ser Ala Ile Arg Arg Tyr Tyr Leu Gly Ala Val Glu Leu Ser
                20                  25                  30

Trp Asn Tyr Ile Gln Ser Asp Leu Leu Ser Val Leu His Thr Asp Ser
            35                  40                  45

Arg Phe Leu Pro Arg Met Ser Thr Ser Phe Pro Phe Asn Thr Ser Ile
        50                  55                  60

Met Tyr Lys Lys Thr Val Phe Val Glu Tyr Lys Asp Gln Leu Phe Asn
65                  70                  75                  80

Ile Ala Lys Pro Arg Pro Pro Trp Met Gly Leu Leu Gly Pro Thr Ile
                85                  90                  95

-continued

```
Trp Thr Glu Val His Asp Thr Val Ile Thr Leu Lys Asn Met Ala
            100                 105                 110
Ser His Pro Val Ser Leu His Ala Val Gly Val Ser Tyr Trp Lys Ala
            115                 120                 125
Ser Glu Gly Asp Glu Tyr Glu Asp Gln Thr Ser Gln Met Glu Lys Glu
            130                 135                 140
Asp Asp Lys Val Phe Pro Gly Glu Ser His Thr Tyr Val Trp Gln Val
145                 150                 155                 160
Leu Lys Glu Asn Gly Pro Met Ala Ser Asp Pro Pro Cys Leu Thr Tyr
                    165                 170                 175
Ser Tyr Met Ser His Val Asp Leu Val Lys Asp Leu Asn Ser Gly Leu
                    180                 185                 190
Ile Gly Ala Leu Leu Val Cys Lys Glu Gly Ser Leu Ser Lys Glu Arg
            195                 200                 205
Thr Gln Met Leu Tyr Gln Phe Val Leu Leu Phe Ala Val Phe Asp Glu
            210                 215                 220
Gly Lys Ser Trp His Ser Glu Thr Asn Asp Ser Tyr Thr Gln Ser Met
225                 230                 235                 240
Asp Ser Ala Ser Ala Arg Asp Trp Pro Lys Met His Thr Val Asn Gly
                    245                 250                 255
Tyr Val Asn Arg Ser Leu Pro Gly Leu Ile Gly Cys His Arg Lys Ser
                    260                 265                 270
Val Tyr Trp His Val Ile Gly Met Gly Thr Thr Pro Glu Ile His Ser
            275                 280                 285
Ile Phe Leu Glu Gly His Thr Phe Phe Val Arg Asn His Arg Gln Ala
            290                 295                 300
Ser Leu Glu Ile Ser Pro Ile Thr Phe Leu Thr Ala Gln Thr Leu Leu
305                 310                 315                 320
Ile Asp Leu Gly Gln Phe Leu Leu Phe Cys His Ile Ser Ser His Lys
                    325                 330                 335
His Asp Gly Met Glu Ala Tyr Val Lys Val Asp Ser Cys Pro Glu Glu
                    340                 345                 350
Ser Gln Trp Gln Lys Lys Asn Asn Asn Glu Glu Met Glu Asp Tyr Asp
            355                 360                 365
Asp Asp Leu Tyr Ser Glu Met Asp Met Phe Thr Leu Asp Tyr Asp Ser
            370                 375                 380
Ser Pro Phe Ile Gln Ile Arg Ser Val Ala Lys Lys Tyr Pro Lys Thr
385                 390                 395                 400
Trp Ile His Tyr Ile Ser Ala Glu Glu Glu Asp Trp Asp Tyr Ala Pro
                    405                 410                 415
Ser Val Pro Thr Ser Asp Asn Gly Ser Tyr Lys Ser Gln Tyr Leu Ser
                    420                 425                 430
Asn Gly Pro His Arg Ile Gly Arg Lys Tyr Lys Lys Val Arg Phe Ile
            435                 440                 445
Ala Tyr Thr Asp Glu Thr Phe Lys Thr Arg Glu Thr Ile Gln His Glu
            450                 455                 460
Ser Gly Leu Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                    485                 490                 495
His Gly Ile Thr Asp Val Ser Pro Leu His Ala Arg Arg Leu Pro Arg
                    500                 505                 510
Gly Ile Lys His Val Lys Asp Leu Pro Ile His Pro Gly Glu Ile Phe
```

-continued

```
                515                 520                 525
Lys Tyr Lys Trp Thr Val Thr Val Glu Asp Gly Pro Thr Lys Ser Asp
            530                 535                 540
Pro Arg Cys Leu Thr Arg Tyr Tyr Ser Ser Phe Ile Asn Pro Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Met Met Ser Asp Lys Arg Asn Val
            580                 585                 590
Ile Leu Phe Ser Ile Phe Asp Glu Asn Gln Ser Trp Tyr Ile Thr Glu
                595                 600                 605
Asn Met Gln Arg Phe Leu Pro Asn Ala Ala Lys Thr Gln Pro Gln Asp
            610                 615                 620
Pro Gly Phe Gln Ala Ser Asn Ile Met His Ser Ile Asn Gly Tyr Val
625                 630                 635                 640
Phe Asp Ser Leu Glu Leu Thr Val Cys Leu His Glu Val Ala Tyr Trp
                645                 650                 655
His Ile Leu Ser Val Gly Ala Gln Thr Asp Phe Leu Ser Ile Phe Phe
            660                 665                 670
Ser Gly Tyr Thr Phe Lys His Lys Met Val Tyr Glu Asp Thr Leu Thr
            675                 680                 685
Leu Phe Pro Phe Ser Gly Glu Thr Val Phe Met Ser Met Glu Asn Pro
690                 695                 700
Gly Leu Trp Val Leu Gly Cys His Asn Ser Asp Phe Arg Lys Arg Gly
705                 710                 715                 720
Met Thr Ala Leu Leu Lys Val Ser Ser Cys Asp Lys Ser Thr Ser Asp
            725                 730                 735
Tyr Tyr Glu Glu Ile Tyr Glu Asp Ile Pro Thr Gln Leu Val Asn Glu
            740                 745                 750
Asn Asn Val Ile Asp Pro Arg Ser Phe Phe Gln Asn Thr Asn His Pro
            755                 760                 765
Asn Thr Arg Lys Lys Lys Phe Lys Asp Ser Thr Ile Pro Lys Asn Asp
770                 775                 780
Met Glu Lys Ile Glu Pro Gln Phe Glu Glu Ile Ala Glu Met Leu Lys
785                 790                 795                 800
Val Gln Ser Val Ser Val Ser Asp Met Leu Met Leu Leu Gly Gln Ser
                805                 810                 815
His Pro Thr Pro His Gly Leu Phe Leu Ser Asp Gly Gln Glu Ala Ile
            820                 825                 830
Tyr Glu Ala Ile His Asp Asp His Ser Pro Asn Ala Ile Asp Ser Asn
            835                 840                 845
Glu Gly Pro Ser Lys Val Thr Gln Leu Arg Pro Glu Ser His His Ser
850                 855                 860
Glu Lys Ile Val Phe Thr Pro Gln Pro Gly Leu Gln Leu Arg Ser Asn
865                 870                 875                 880
Lys Ser Leu Glu Thr Thr Ile Glu Val Lys Trp Lys Lys Leu Gly Leu
                885                 890                 895
Gln Val Ser Ser Leu Pro Ser Asn Leu Met Thr Thr Thr Ile Leu Ser
            900                 905                 910
Asp Asn Leu Lys Ala Thr Phe Glu Lys Thr Asp Ser Ser Gly Phe Pro
            915                 920                 925
Asp Met Pro Val His Ser Ser Ser Lys Leu Ser Thr Thr Ala Phe Gly
930                 935                 940
```

```
Lys Lys Ala Tyr Ser Leu Val Gly Ser His Val Pro Leu Asn Ala Ser
945                 950                 955                 960

Glu Glu Asn Ser Asp Ser Asn Ile Leu Asp Ser Thr Leu Met Tyr Ser
                965                 970                 975

Gln Glu Ser Leu Pro Arg Asp Asn Ile Leu Ser Ile Glu Asn Asp Arg
            980                 985                 990

Leu Leu Arg Glu Lys Arg Phe His Gly Ile Ala Leu Leu Thr Lys Asp
        995                 1000                1005

Asn Thr Leu Phe Lys Asp Asn Val Ser Leu Met Lys Thr Asn Lys Thr
    1010                1015                1020

Tyr Asn His Ser Thr Thr Asn Glu Lys Leu His Thr Glu Ser Pro Thr
1025                1030                1035                1040

Ser Ile Glu Asn Ser Thr Thr Asp Leu Gln Asp Ala Ile Leu Lys Val
                1045                1050                1055

Asn Ser Glu Ile Gln Glu Val Thr Ala Leu Ile His Asp Gly Thr Leu
            1060                1065                1070

Leu Gly Lys Asn Ser Thr Tyr Leu Arg Leu Asn His Met Leu Asn Arg
        1075                1080                1085

Thr Thr Ser Thr Lys Asn Lys Asp Ile Phe His Arg Lys Asp Glu Asp
    1090                1095                1100

Pro Ile Pro Gln Asp Glu Glu Asn Thr Ile Met Pro Phe Ser Lys Met
1105                1110                1115                1120

Leu Phe Leu Ser Glu Ser Ser Asn Trp Phe Lys Thr Asn Gly Asn
                1125                1130                1135

Asn Ser Leu Asn Ser Glu Gln Glu His Ser Pro Lys Gln Leu Val Tyr
            1140                1145                1150

Leu Met Phe Lys Lys Tyr Val Lys Asn Gln Ser Phe Leu Ser Glu Lys
        1155                1160                1165

Asn Lys Val Thr Val Glu Gln Asp Gly Phe Thr Lys Asn Ile Gly Leu
    1170                1175                1180

Lys Asp Met Ala Phe Pro His Asn Met Ser Ile Phe Leu Thr Thr Leu
1185                1190                1195                1200

Ser Asn Val His Glu Asn Gly Arg His Asn Gln Glu Lys Asn Ile Gln
                1205                1210                1215

Glu Glu Ile Glu Lys Glu Ala Leu Ile Glu Glu Lys Val Val Leu Pro
            1220                1225                1230

Gln Val His Glu Ala Thr Gly Ser Lys Asn Phe Leu Lys Asp Ile Leu
        1235                1240                1245

Ile Leu Gly Thr Arg Gln Asn Ile Ser Leu Tyr Glu Val His Val Pro
    1250                1255                1260

Val Leu Gln Asn Ile Thr Ser Ile Asn Asn Ser Thr Asn Thr Val Gln
1265                1270                1275                1280

Ile His Met Glu His Phe Phe Lys Arg Arg Lys Asp Lys Glu Thr Asn
                1285                1290                1295

Ser Glu Gly Leu Val Asn Lys Thr Arg Glu Met Val Lys Asn Tyr Pro
            1300                1305                1310

Ser Gln Lys Asn Ile Thr Thr Gln Arg Ser Lys Arg Ala Leu Gly Gln
        1315                1320                1325

Phe Arg Leu Ser Thr Gln Trp Leu Lys Thr Ile Asn Cys Ser Thr Gln
    1330                1335                1340

Cys Ile Ile Lys Gln Ile Asp His Ser Lys Glu Met Lys Lys Phe Ile
1345                1350                1355                1360
```

```
-continued

Thr Lys Ser Ser Leu Ser Asp Ser Ser Val Ile Lys Ser Thr Thr Gln
            1365                1370                1375

Thr Asn Ser Ser Asp Ser His Ile Val Lys Thr Ser Ala Phe Pro Pro
            1380                1385                1390

Ile Asp Leu Lys Arg Ser Pro Phe Gln Asn Lys Phe Ser His Val Gln
        1395                1400                1405

Ala Ser Ser Tyr Ile Tyr Asp Phe Lys Thr Lys Ser Ser Arg Ile Gln
    1410                1415                1420

Glu Ser Asn Asn Phe Leu Lys Glu Thr Lys Ile Asn Asn Pro Ser Leu
1425                1430                1435                1440

Ala Ile Leu Pro Trp Asn Met Phe Ile Asp Gln Gly Lys Phe Thr Ser
            1445                1450                1455

Pro Gly Lys Ser Asn Thr Asn Ser Val Thr Tyr Lys Lys Arg Glu Asn
            1460                1465                1470

Ile Ile Phe Leu Lys Pro Thr Leu Pro Glu Glu Ser Gly Lys Ile Glu
        1475                1480                1485

Leu Leu Pro Gln Val Ser Ile Gln Glu Glu Ile Leu Pro Thr Glu
        1490                1495                1500

Thr Ser His Gly Ser Pro Gly His Leu Asn Leu Met Lys Glu Val Phe
1505                1510                1515                1520

Leu Gln Lys Ile Gln Gly Pro Thr Lys Trp Asn Lys Ala Lys Arg His
            1525                1530                1535

Gly Glu Ser Ile Lys Gly Lys Thr Glu Ser Ser Lys Asn Thr Arg Ser
            1540                1545                1550

Lys Leu Leu Asn His His Ala Trp Asp Tyr His Tyr Ala Ala Gln Ile
        1555                1560                1565

Pro Lys Asp Met Trp Lys Ser Lys Glu Lys Ser Pro Glu Ile Ile Ser
    1570                1575                1580

Ile Lys Gln Glu Asp Thr Ile Leu Ser Leu Arg Pro His Gly Asn Ser
1585                1590                1595                1600

His Ser Ile Gly Ala Asn Glu Lys Gln Asn Trp Pro Gln Arg Glu Thr
            1605                1610                1615

Thr Trp Val Lys Gln Gly Gln Thr Gln Arg Thr Cys Ser Gln Ile Pro
            1620                1625                1630

Pro Val Leu Lys Arg His Gln Arg Glu Leu Ser Ala Phe Gln Ser Glu
        1635                1640                1645

Gln Glu Ala Thr Asp Tyr Asp Asp Ala Ile Thr Ile Glu Thr Ile Glu
    1650                1655                1660

Asp Phe Asp Ile Tyr Ser Glu Asp Ile Lys Gln Gly Pro Arg Ser Phe
1665                1670                1675                1680

Gln Gln Lys Thr Arg His Tyr Phe Ile Ala Ala Val Glu Arg Leu Trp
            1685                1690                1695

Asp Tyr Gly Met Ser Thr Ser His Val Leu Arg Asn Arg Tyr Gln Ser
            1700                1705                1710

Asp Asn Val Pro Gln Phe Lys Lys Val Val Phe Gln Glu Phe Thr Asp
        1715                1720                1725

Gly Ser Phe Ser Gln Pro Leu Tyr Arg Gly Glu Leu Asn Glu His Leu
    1730                1735                1740

Gly Leu Leu Gly Pro Tyr Ile Arg Ala Glu Val Glu Asp Asn Ile Met
1745                1750                1755                1760

Val Thr Phe Lys Asn Gln Ala Ser Arg Pro Tyr Ser Phe Tyr Ser Ser
            1765                1770                1775

Leu Ile Ser Tyr Lys Glu Asp Gln Arg Gly Glu Glu Pro Arg Arg Asn
```

-continued

```
                    1780                1785                1790
Phe Val Lys Pro Asn Glu Thr Lys Ile Tyr Phe Trp Lys Val Gln His
        1795                1800                1805
His Met Ala Pro Thr Glu Asp Glu Phe Asp Cys Lys Ala Trp Ala Tyr
    1810                1815                1820
Phe Ser Asp Val Asp Leu Glu Arg Asp Met His Ser Gly Leu Ile Gly
1825                1830                1835                1840
Pro Leu Leu Ile Cys His Ala Asn Thr Leu Asn Pro Ala His Gly Arg
            1845                1850                1855
Gln Val Ser Val Gln Glu Phe Ala Leu Leu Phe Thr Ile Phe Asp Glu
        1860                1865                1870
Thr Lys Ser Trp Tyr Phe Thr Glu Asn Val Lys Arg Asn Cys Lys Thr
    1875                1880                1885
Pro Cys Asn Phe Gln Met Glu Asp Pro Thr Leu Lys Glu Asn Tyr Arg
    1890                1895                1900
Phe His Ala Ile Asn Gly Tyr Val Met Asp Thr Leu Pro Gly Leu Val
1905                1910                1915                1920
Met Ala Gln Asp Gln Arg Ile Arg Trp Tyr Leu Leu Ser Met Gly Asn
            1925                1930                1935
Asn Glu Asn Ile Gln Ser Ile His Phe Ser Gly His Val Phe Thr Val
        1940                1945                1950
Arg Lys Lys Glu Glu Tyr Lys Met Ala Val Tyr Asn Leu Tyr Pro Gly
        1955                1960                1965
Val Phe Glu Thr Leu Glu Met Ile Pro Ser Arg Ala Gly Ile Trp Arg
    1970                1975                1980
Val Glu Cys Leu Ile Gly Glu His Leu Gln Ala Gly Met Ser Thr Leu
1985                1990                1995                2000
Phe Leu Val Tyr Ser Lys Gln Cys Gln Ile Pro Leu Gly Met Ala Ser
            2005                2010                2015
Gly Ser Ile Arg Asp Phe Gln Ile Thr Ala Ser Gly His Tyr Gly Gln
        2020                2025                2030
Trp Ala Pro Asn Leu Ala Arg Leu His Tyr Ser Gly Ser Ile Asn Ala
    2035                2040                2045
Trp Ser Thr Lys Glu Pro Phe Ser Trp Ile Lys Val Asp Leu Leu Ala
    2050                2055                2060
Pro Met Ile Val His Gly Ile Lys Thr Gln Gly Ala Arg Gln Lys Phe
2065                2070                2075                2080
Ser Ser Leu Tyr Ile Ser Gln Phe Ile Ile Met Tyr Ser Leu Asp Gly
            2085                2090                2095
Lys Lys Trp Leu Ser Tyr Gln Gly Asn Ser Thr Gly Thr Leu Met Val
        2100                2105                2110
Phe Phe Gly Asn Val Asp Ser Ser Gly Ile Lys His Asn Ser Phe Asn
    2115                2120                2125
Pro Pro Ile Ile Ala Arg Tyr Ile Arg Leu His Pro Thr His Ser Ser
    2130                2135                2140
Ile Arg Ser Thr Leu Arg Met Glu Leu Met Gly Cys Asp Leu Asn Ser
2145                2150                2155                2160
Cys Ser Ile Pro Leu Gly Met Glu Ser Lys Val Ile Ser Asp Thr Gln
            2165                2170                2175
Ile Thr Ala Ser Ser Tyr Phe Thr Asn Met Phe Ala Thr Trp Ser Pro
        2180                2185                2190
Ser Gln Ala Arg Leu His Leu Gln Gly Arg Thr Asn Ala Trp Arg Pro
    2195                2200                2205
```

```
Gln Val Asn Asp Pro Lys Gln Trp Leu Gln Val Asp Leu Gln Lys Thr
    2210                2215                2220
Met Lys Val Thr Gly Ile Ile Thr Gln Gly Val Lys Ser Leu Phe Thr
2225                2230                2235                2240
Ser Met Phe Val Lys Glu Phe Leu Ile Ser Ser Ser Gln Asp Gly His
            2245                2250                2255
His Trp Thr Gln Ile Leu Tyr Asn Gly Lys Val Lys Val Phe Gln Gly
            2260                2265                2270
Asn Gln Asp Ser Ser Thr Pro Met Met Asn Ser Leu Asp Pro Pro Leu
    2275                2280                2285
Leu Thr Arg Tyr Leu Arg Ile His Pro Gln Ile Trp Glu His Gln Ile
    2290                2295                2300
Ala Leu Arg Leu Glu Ile Leu Gly Cys Glu Ala Gln Gln Gln Tyr
2305                2310                2315

<210> SEQ ID NO 29
<211> LENGTH: 6402
<212> TYPE: DNA
<213> ORGANISM: Porcine
<220> FEATURE:
<221> NAME/KEY: CDS
<222> LOCATION: (1)..(6399)

<400> SEQUENCE: 29 atg cag cta gag ctc tcc acc tgt gtc ttt ctg tgt ctc ttg cca ctc        48
Met Gln Leu Glu Leu Ser Thr Cys Val Phe Leu Cys Leu Leu Pro Leu
 1               5                  10                  15 ggc ttt agt gcc atc agg aga tac tac ctg ggc gca gtg gaa ctg tcc        96
Gly Phe Ser Ala Ile Arg Arg Tyr Tyr Leu Gly Ala Val Glu Leu Ser
            20                  25                  30 tgg gac tac cgg caa agt gaa ctc ctc cgt gag ctg cac gtg gac acc       144
Trp Asp Tyr Arg Gln Ser Glu Leu Leu Arg Glu Leu His Val Asp Thr
        35                  40                  45 aga ttt cct gct aca gcg cca gga gct ctt ccg ttg ggc ccg tca gtc       192
Arg Phe Pro Ala Thr Ala Pro Gly Ala Leu Pro Leu Gly Pro Ser Val
    50                  55                  60 ctg tac aaa aag act gtg ttc gta gag ttc acg gat caa ctt ttc agc       240
Leu Tyr Lys Lys Thr Val Phe Val Glu Phe Thr Asp Gln Leu Phe Ser
65                  70                  75                  80 gtt gcc agg ccc agg cca cca tgg atg ggt ctg ctg ggt cct acc atc       288
Val Ala Arg Pro Arg Pro Pro Trp Met Gly Leu Leu Gly Pro Thr Ile
                85                  90                  95 cag gct gag gtt tac gac acg gtg gtc gtt acc ctg aag aac atg gct       336
Gln Ala Glu Val Tyr Asp Thr Val Val Val Thr Leu Lys Asn Met Ala
            100                 105                 110 tct cat ccc gtt agt ctt cac gct gtc ggc gtc tcc ttc tgg aaa tct       384
Ser His Pro Val Ser Leu His Ala Val Gly Val Ser Phe Trp Lys Ser
        115                 120                 125 tcc gaa ggc gct gaa tat gag gat cac acc agc caa agg gag aag gaa       432
Ser Glu Gly Ala Glu Tyr Glu Asp His Thr Ser Gln Arg Glu Lys Glu
    130                 135                 140 gac gat aaa gtc ctt ccc ggt aaa agc caa acc tac gtc tgg cag gtc       480
Asp Asp Lys Val Leu Pro Gly Lys Ser Gln Thr Tyr Val Trp Gln Val
145                 150                 155                 160 ctg aaa gaa aat ggt cca aca gcc tct gac cca cca tgt ctc acc tac       528
Leu Lys Glu Asn Gly Pro Thr Ala Ser Asp Pro Pro Cys Leu Thr Tyr
                165                 170                 175 tca tac ctg tct cac gtg gac ctg gtg aaa gac ctg aat tcg ggc ctc       576
Ser Tyr Leu Ser His Val Asp Leu Val Lys Asp Leu Asn Ser Gly Leu
```

-continued

```
                180                 185                 190
att gga gcc ctg ctg gtt tgt aga gaa ggg agt ctg acc aga gaa agg      624
Ile Gly Ala Leu Leu Val Cys Arg Glu Gly Ser Leu Thr Arg Glu Arg
        195                 200                 205 acc cag aac ctg cac gaa ttt gta cta ctt ttt gct gtc ttt gat gaa      672
Thr Gln Asn Leu His Glu Phe Val Leu Leu Phe Ala Val Phe Asp Glu
    210                 215                 220 ggg aaa agt tgg cac tca gca aga aat gac tcc tgg aca cgg gcc atg      720
Gly Lys Ser Trp His Ser Ala Arg Asn Asp Ser Trp Thr Arg Ala Met
225                 230                 235                 240 gat ccc gca cct gcc agg gcc cag cct gca atg cac aca gtc aat ggc      768
Asp Pro Ala Pro Ala Arg Ala Gln Pro Ala Met His Thr Val Asn Gly
                245                 250                 255 tat gtc aac agg tct ctg cca ggt ctg atc gga tgt cat aag aaa tca      816
Tyr Val Asn Arg Ser Leu Pro Gly Leu Ile Gly Cys His Lys Lys Ser
            260                 265                 270 gtc tac tgg cac gtg att gga atg ggc acc agc ccg gaa gtg cac tcc      864
Val Tyr Trp His Val Ile Gly Met Gly Thr Ser Pro Glu Val His Ser
        275                 280                 285 att ttt ctt gaa ggc cac acg ttt ctc gtg agg cac cat cgc cag gct      912
Ile Phe Leu Glu Gly His Thr Phe Leu Val Arg His His Arg Gln Ala
    290                 295                 300 tcc ttg gag atc tcg cca cta act ttc ctc act gct cag aca ttc ctg      960
Ser Leu Glu Ile Ser Pro Leu Thr Phe Leu Thr Ala Gln Thr Phe Leu
305                 310                 315                 320 atg gac ctt ggc cag ttc cta ctg ttt tgt cat atc tct tcc cac cac     1008
Met Asp Leu Gly Gln Phe Leu Leu Phe Cys His Ile Ser Ser His His
                325                 330                 335 cat ggt ggc atg gag gct cac gtc aga gta gaa agc tgc gcc gag gag     1056
His Gly Gly Met Glu Ala His Val Arg Val Glu Ser Cys Ala Glu Glu
            340                 345                 350 ccc cag ctg cgg agg aaa gct gat gaa gag gaa gat tat gat gac aat     1104
Pro Gln Leu Arg Arg Lys Ala Asp Glu Glu Glu Asp Tyr Asp Asp Asn
        355                 360                 365 ttg tac gac tcg gac atg gac gtg gtc cgg ctc gat ggt gac gac gtg     1152
Leu Tyr Asp Ser Asp Met Asp Val Val Arg Leu Asp Gly Asp Asp Val
    370                 375                 380 tct ccc ttt atc caa atc cgc tcg gtt gcc aag aag cat ccc aaa acc     1200
Ser Pro Phe Ile Gln Ile Arg Ser Val Ala Lys Lys His Pro Lys Thr
385                 390                 395                 400 tgg gtg cac tac atc tct gca gag gag gag gac tgg gac tac gcc ccc     1248
Trp Val His Tyr Ile Ser Ala Glu Glu Glu Asp Trp Asp Tyr Ala Pro
                405                 410                 415 gcg gtc ccc agc ccc agt gac aga agt tat aaa agt ctc tac ttg aac     1296
Ala Val Pro Ser Pro Ser Asp Arg Ser Tyr Lys Ser Leu Tyr Leu Asn
            420                 425                 430 agt ggt cct cag cga att ggt agg aaa tac aaa aaa gct cga ttc gtc     1344
Ser Gly Pro Gln Arg Ile Gly Arg Lys Tyr Lys Lys Ala Arg Phe Val
        435                 440                 445 gct tac acg gat gta aca ttt aag act cgt aaa gct att ccg tat gaa     1392
Ala Tyr Thr Asp Val Thr Phe Lys Thr Arg Lys Ala Ile Pro Tyr Glu
    450                 455                 460 tca gga atc ctg gga cct tta ctt tat gga gaa gtt gga gac aca ctt     1440
Ser Gly Ile Leu Gly Pro Leu Leu Tyr Gly Glu Val Gly Asp Thr Leu
465                 470                 475                 480 ttg att ata ttt aag aat aaa gcg agc cga cca tat aac atc tac cct     1488
Leu Ile Ile Phe Lys Asn Lys Ala Ser Arg Pro Tyr Asn Ile Tyr Pro
                485                 490                 495 cat gga atc act gat gtc agc gct ttg cac cca ggg aga ctt cta aaa     1536
```

```
                        -continued

His Gly Ile Thr Asp Val Ser Ala Leu His Pro Gly Arg Leu Leu Lys
            500                 505                 510 ggt tgg aaa cat ttg aaa gac atg cca att ctg cca gga gag act ttc      1584
Gly Trp Lys His Leu Lys Asp Met Pro Ile Leu Pro Gly Glu Thr Phe
            515                 520                 525 aag tat aaa tgg aca gtg act gtg gaa gat ggg cca acc aag tcc gat      1632
Lys Tyr Lys Trp Thr Val Thr Val Glu Asp Gly Pro Thr Lys Ser Asp
        530                 535                 540 cct cgg tgc ctg acc cgc tac tac tcg agc tcc att aat cta gag aaa      1680
Pro Arg Cys Leu Thr Arg Tyr Tyr Ser Ser Ser Ile Asn Leu Glu Lys
545                 550                 555                 560 gat ctg gct tcg gga ctc att ggc cct ctc ctc atc tgc tac aaa gaa      1728
Asp Leu Ala Ser Gly Leu Ile Gly Pro Leu Leu Ile Cys Tyr Lys Glu
                565                 570                 575 tct gta gac caa aga gga aac cag atg atg tca gac aag aga aac gtc      1776
Ser Val Asp Gln Arg Gly Asn Gln Met Met Ser Asp Lys Arg Asn Val
            580                 585                 590 atc ctg ttt tct gta ttc gat gag aat caa agc tgg tac ctc gca gag      1824
Ile Leu Phe Ser Val Phe Asp Glu Asn Gln Ser Trp Tyr Leu Ala Glu
            595                 600                 605 aat att cag cgc ttc ctc ccc aat ccg gat gga tta cag ccc cag gat      1872
Asn Ile Gln Arg Phe Leu Pro Asn Pro Asp Gly Leu Gln Pro Gln Asp
        610                 615                 620 cca gag ttc caa gct tct aac atc atg cac agc atc aat ggc tat gtt      1920
Pro Glu Phe Gln Ala Ser Asn Ile Met His Ser Ile Asn Gly Tyr Val
625                 630                 635                 640 ttt gat agc ttg cag ctg tcg gtt tgt ttg cac gag gtg gca tac tgg      1968
Phe Asp Ser Leu Gln Leu Ser Val Cys Leu His Glu Val Ala Tyr Trp
                645                 650                 655 tac att cta agt gtt gga gca cag acg gac ttc ctc tcc gtc ttc ttc      2016
Tyr Ile Leu Ser Val Gly Ala Gln Thr Asp Phe Leu Ser Val Phe Phe
            660                 665                 670 tct ggc tac acc ttc aaa cac aaa atg gtc tat gaa gac aca ctc acc      2064
Ser Gly Tyr Thr Phe Lys His Lys Met Val Tyr Glu Asp Thr Leu Thr
            675                 680                 685 ctg ttc ccc ttc tca gga gaa acg gtc ttc atg tca atg gaa aac cca      2112
Leu Phe Pro Phe Ser Gly Glu Thr Val Phe Met Ser Met Glu Asn Pro
        690                 695                 700 ggt ctc tgg gtc cta ggg tgc cac aac tca gac ttg cgg aac aga ggg      2160
Gly Leu Trp Val Leu Gly Cys His Asn Ser Asp Leu Arg Asn Arg Gly
705                 710                 715                 720 atg aca gcc tta ctg aag gtg tat agt tgt gac agg gac att ggt gat      2208
Met Thr Ala Leu Leu Lys Val Tyr Ser Cys Asp Arg Asp Ile Gly Asp
                725                 730                 735 tat tat gac aac act tat gaa gat att cca ggc ttc ttg ctg agt gga      2256
Tyr Tyr Asp Asn Thr Tyr Glu Asp Ile Pro Gly Phe Leu Leu Ser Gly
            740                 745                 750 aag aat gtc att gaa ccc aga agc ttt gcc cag aat tca aga ccc cct      2304
Lys Asn Val Ile Glu Pro Arg Ser Phe Ala Gln Asn Ser Arg Pro Pro
            755                 760                 765 agt gcg agc caa aag caa ttc caa acc atc aca agt cca gaa gat gac      2352
Ser Ala Ser Gln Lys Gln Phe Gln Thr Ile Thr Ser Pro Glu Asp Asp
        770                 775                 780 gtg gag ctt gac ccg cag tct gga gag aga acc caa gca ctg gaa gaa      2400
Val Glu Leu Asp Pro Gln Ser Gly Glu Arg Thr Gln Ala Leu Glu Glu
785                 790                 795                 800 cta agt gtc ccc tct ggt gat ggg tcg atg ctc ttg gga cag aat cct      2448
Leu Ser Val Pro Ser Gly Asp Gly Ser Met Leu Leu Gly Gln Asn Pro
                805                 810                 815
```

```
gct cca cat ggc tca tcc tca tct gat ctt caa gaa gcc agg aat gag      2496
Ala Pro His Gly Ser Ser Ser Ser Asp Leu Gln Glu Ala Arg Asn Glu
            820                 825                 830 gct gat gat tat tta cct gga gca aga gaa aga ggc acg gcc cca tcc      2544
Ala Asp Asp Tyr Leu Pro Gly Ala Arg Glu Arg Gly Thr Ala Pro Ser
        835                 840                 845 gca gcg gca cgt ctc aga cca gag ctg cat cac agt gcc gaa aga gta      2592
Ala Ala Ala Arg Leu Arg Pro Glu Leu His His Ser Ala Glu Arg Val
850                 855                 860 ctt act cct gag cca gag aaa gag ttg aag aaa ctt gat tca aaa atg      2640
Leu Thr Pro Glu Pro Glu Lys Glu Leu Lys Lys Leu Asp Ser Lys Met
865                 870                 875                 880 tct agt tca tca gac ctt cta aag act tcg cca aca att cca tca gac      2688
Ser Ser Ser Ser Asp Leu Leu Lys Thr Ser Pro Thr Ile Pro Ser Asp
                885                 890                 895 acg ttg tca gcg gag act gaa agg aca cat tcc tta ggc ccc cca cac      2736
Thr Leu Ser Ala Glu Thr Glu Arg Thr His Ser Leu Gly Pro Pro His
            900                 905                 910 ccg cag gtt aat ttc agg agt caa tta ggt gcc att gta ctt ggc aaa      2784
Pro Gln Val Asn Phe Arg Ser Gln Leu Gly Ala Ile Val Leu Gly Lys
        915                 920                 925 aat tca tct cac ttt att ggg gct ggt gtc cct ttg ggc tcg act gag      2832
Asn Ser Ser His Phe Ile Gly Ala Gly Val Pro Leu Gly Ser Thr Glu
930                 935                 940 gag gat cat gaa agc tcc ctg gga gaa aat gta tca cca gtg gag agt      2880
Glu Asp His Glu Ser Ser Leu Gly Glu Asn Val Ser Pro Val Glu Ser
945                 950                 955                 960 gac ggg ata ttt gaa aag gaa aga gct cat gga cct gct tca ctg acc      2928
Asp Gly Ile Phe Glu Lys Glu Arg Ala His Gly Pro Ala Ser Leu Thr
                965                 970                 975 aaa gac gat gtt tta ttt aaa gtt aat atc tct ttg gta aag aca aac      2976
Lys Asp Asp Val Leu Phe Lys Val Asn Ile Ser Leu Val Lys Thr Asn
            980                 985                 990 aag gca cga gtt tac tta aaa act aat aga aag att cac att gat gac      3024
Lys Ala Arg Val Tyr Leu Lys Thr Asn Arg Lys Ile His Ile Asp Asp
        995                 1000                1005 gca gct tta tta act gag aat agg gca tct gca acg ttt atg gac aaa      3072
Ala Ala Leu Leu Thr Glu Asn Arg Ala Ser Ala Thr Phe Met Asp Lys
    1010                1015                1020 aat act aca gct tcg gga tta aat cat gtg tca aat tgg ata aaa ggg      3120
Asn Thr Thr Ala Ser Gly Leu Asn His Val Ser Asn Trp Ile Lys Gly
1025                1030                1035                1040 ccc ctt ggc aag aac ccc cta agc tcg gag cga ggc ccc agt cca gag      3168
Pro Leu Gly Lys Asn Pro Leu Ser Ser Glu Arg Gly Pro Ser Pro Glu
                1045                1050                1055 ctt ctg aca tct tca gga tca gga aaa tct gtg aaa ggt cag agt tct      3216
Leu Leu Thr Ser Ser Gly Ser Gly Lys Ser Val Lys Gly Gln Ser Ser
            1060                1065                1070 ggg cag ggg aga ata cgg gtg gca gtg gaa gag gaa gaa ctg agc aaa      3264
Gly Gln Gly Arg Ile Arg Val Ala Val Glu Glu Glu Glu Leu Ser Lys
        1075                1080                1085 ggc aaa gag atg atg ctt ccc aac agc gag ctc acc ttt ctc act aac      3312
Gly Lys Glu Met Met Leu Pro Asn Ser Glu Leu Thr Phe Leu Thr Asn
    1090                1095                1100 tcg gct gat gtc caa gga aac gat aca cac agt caa gga aaa aag tct      3360
Ser Ala Asp Val Gln Gly Asn Asp Thr His Ser Gln Gly Lys Lys Ser
1105                1110                1115                1120 cgg gaa gag atg gaa agg aga gaa aaa tta gtc caa gaa aaa gtc gac      3408
Arg Glu Glu Met Glu Arg Arg Glu Lys Leu Val Gln Glu Lys Val Asp
                1125                1130                1135
```

```
ttg cct cag gtg tat aca gcg act gga act aag aat ttc ctg aga aac     3456
Leu Pro Gln Val Tyr Thr Ala Thr Gly Thr Lys Asn Phe Leu Arg Asn
            1140                1145                1150 att ttt cac caa agc act gag ccc agt gta gaa ggg ttt gat ggg ggg     3504
Ile Phe His Gln Ser Thr Glu Pro Ser Val Glu Gly Phe Asp Gly Gly
        1155                1160                1165 tca cat gcg ccg gtg cct caa gac agc agg tca tta aat gat tcg gca     3552
Ser His Ala Pro Val Pro Gln Asp Ser Arg Ser Leu Asn Asp Ser Ala
    1170                1175                1180 gag aga gca gag act cac ata gcc cat ttc tca gca att agg gaa gag     3600
Glu Arg Ala Glu Thr His Ile Ala His Phe Ser Ala Ile Arg Glu Glu
1185                1190                1195                1200 gca ccc ttg gaa gcc ccg gga aat cga aca ggt cca ggt ccg agg agt     3648
Ala Pro Leu Glu Ala Pro Gly Asn Arg Thr Gly Pro Gly Pro Arg Ser
            1205                1210                1215 gcg gtt ccc cgc cgc gtt aag cag agc ttg aaa cag atc aga ctc ccg     3696
Ala Val Pro Arg Arg Val Lys Gln Ser Leu Lys Gln Ile Arg Leu Pro
        1220                1225                1230 cta gaa gaa ata aag cct gaa agg ggg gtg gtt ctg aat gcc acc tca     3744
Leu Glu Glu Ile Lys Pro Glu Arg Gly Val Val Leu Asn Ala Thr Ser
    1235                1240                1245 acc cgg tgg tct gaa agc agt cct atc tta caa gga gcc aaa aga aat     3792
Thr Arg Trp Ser Glu Ser Ser Pro Ile Leu Gln Gly Ala Lys Arg Asn
1250                1255                1260 aac ctt tct tta cct ttc ctg acc ttg gaa atg gcc gga ggt caa gga     3840
Asn Leu Ser Leu Pro Phe Leu Thr Leu Glu Met Ala Gly Gly Gln Gly
1265                1270                1275                1280 aag atc agc gcc ctg ggg aaa agt gcc gca ggc ccg ctg gcg tcc ggg     3888
Lys Ile Ser Ala Leu Gly Lys Ser Ala Ala Gly Pro Leu Ala Ser Gly
            1285                1290                1295 aag ctg gag aag gct gtt ctc tct tca gca ggc ttg tct gaa gca tct     3936
Lys Leu Glu Lys Ala Val Leu Ser Ser Ala Gly Leu Ser Glu Ala Ser
        1300                1305                1310 ggc aaa gct gag ttt ctt cct aaa gtt cga gtt cat cgg gaa gac ctg     3984
Gly Lys Ala Glu Phe Leu Pro Lys Val Arg Val His Arg Glu Asp Leu
    1315                1320                1325 ttg cct caa aaa acc agc aat gtt tct tgc gca cac ggg gat ctc ggc     4032
Leu Pro Gln Lys Thr Ser Asn Val Ser Cys Ala His Gly Asp Leu Gly
1330                1335                1340 cag gag atc ttc ctg cag aaa aca cgg gga cct gtt aac ctg aac aaa     4080
Gln Glu Ile Phe Leu Gln Lys Thr Arg Gly Pro Val Asn Leu Asn Lys
1345                1350                1355                1360 gta aat aga cct gga agg act ccc tcc aag ctt ctg ggt ccc ccg atg     4128
Val Asn Arg Pro Gly Arg Thr Pro Ser Lys Leu Leu Gly Pro Pro Met
            1365                1370                1375 ccc aaa gag tgg gaa tcc cta gag aag tca cca aaa agc aca gct ctc     4176
Pro Lys Glu Trp Glu Ser Leu Glu Lys Ser Pro Lys Ser Thr Ala Leu
        1380                1385                1390 agg acg aaa gac atc atc agt tta ccc ctg gac cgt cac gaa agc aat     4224
Arg Thr Lys Asp Ile Ile Ser Leu Pro Leu Asp Arg His Glu Ser Asn
    1395                1400                1405 cat tca ata gca gca aaa aat gaa gga caa gcc gag acc caa aga gaa     4272
His Ser Ile Ala Ala Lys Asn Glu Gly Gln Ala Glu Thr Gln Arg Glu
1410                1415                1420 gcc gcc tgg acg aag cag gga ggg cct gga agg ctg tgc gct cca aag     4320
Ala Ala Trp Thr Lys Gln Gly Gly Pro Gly Arg Leu Cys Ala Pro Lys
1425                1430                1435                1440 cct ccg gtc ctg cga cgg cat cag agg gac ata agc ctt cct act ttt     4368
Pro Pro Val Leu Arg Arg His Gln Arg Asp Ile Ser Leu Pro Thr Phe
```

-continued

|  |  |  |  |  |  |  |  |  |  |  |  |  |  |
|---|---|---|---|---|---|---|---|---|---|---|---|---|---|
|  |  | 1445 |  |  | 1450 |  |  |  | 1455 |  |  |  |  | cag ccg gag gaa gac aaa atg gac tat gat gat atc ttc tca act gaa     4416
Gln Pro Glu Glu Asp Lys Met Asp Tyr Asp Asp Ile Phe Ser Thr Glu
         1460          1465          1470 acg aag gga gaa gat ttt gac att tac ggt gag gat gaa aat cag gac     4464
Thr Lys Gly Glu Asp Phe Asp Ile Tyr Gly Glu Asp Glu Asn Gln Asp
    1475          1480          1485 cct cgc agc ttt cag aag aga acc cga cac tat ttc att gct gcg gtg     4512
Pro Arg Ser Phe Gln Lys Arg Thr Arg His Tyr Phe Ile Ala Ala Val
         1490          1495          1500 gag cag ctc tgg gat tac ggg atg agc gaa tcc ccc cgg gcg cta aga     4560
Glu Gln Leu Trp Asp Tyr Gly Met Ser Glu Ser Pro Arg Ala Leu Arg
1505          1510          1515          1520 aac agg gct cag aac gga gag gtg cct cgg ttc aag aag gtg gtc ttc     4608
Asn Arg Ala Gln Asn Gly Glu Val Pro Arg Phe Lys Lys Val Val Phe
         1525          1530          1535 cgg gaa ttt gct gac ggc tcc ttc acg cag ccg tcg tac cgc ggg gaa     4656
Arg Glu Phe Ala Asp Gly Ser Phe Thr Gln Pro Ser Tyr Arg Gly Glu
    1540          1545          1550 ctc aac aaa cac ttg ggg ctc ttg gga ccc tac atc aga gcg gaa gtt     4704
Leu Asn Lys His Leu Gly Leu Leu Gly Pro Tyr Ile Arg Ala Glu Val
         1555          1560          1565 gaa gac aac atc atg gta act ttc aaa aac cag gcg tct cgt ccc tat     4752
Glu Asp Asn Ile Met Val Thr Phe Lys Asn Gln Ala Ser Arg Pro Tyr
    1570          1575          1580 tcc ttc tac tcg agc ctt att tct tat ccg gat gat cag gag caa ggg     4800
Ser Phe Tyr Ser Ser Leu Ile Ser Tyr Pro Asp Asp Gln Glu Gln Gly
1585          1590          1595          1600 gca gaa cct cga cac aac ttc gtc cag cca aat gaa acc aga act tac     4848
Ala Glu Pro Arg His Asn Phe Val Gln Pro Asn Glu Thr Arg Thr Tyr
         1605          1610          1615 ttt tgg aaa gtg cag cat cac atg gca ccc aca gaa gac gag ttt gac     4896
Phe Trp Lys Val Gln His His Met Ala Pro Thr Glu Asp Glu Phe Asp
    1620          1625          1630 tgc aaa gcc tgg gcc tac ttt tct gat gtt gac ctg gaa aaa gat gtg     4944
Cys Lys Ala Trp Ala Tyr Phe Ser Asp Val Asp Leu Glu Lys Asp Val
         1635          1640          1645 cac tca ggc ttg atc ggc ccc ctt ctg atc tgc cgc gcc aac acc ctg     4992
His Ser Gly Leu Ile Gly Pro Leu Leu Ile Cys Arg Ala Asn Thr Leu
    1650          1655          1660 aac gct gct cac ggt aga caa gtg acc gtg caa gaa ttt gct ctg ttt     5040
Asn Ala Ala His Gly Arg Gln Val Thr Val Gln Glu Phe Ala Leu Phe
1665          1670          1675          1680 ttc act att ttt gat gag aca aag agc tgg tac ttc act gaa aat gtg     5088
Phe Thr Ile Phe Asp Glu Thr Lys Ser Trp Tyr Phe Thr Glu Asn Val
         1685          1690          1695 gaa agg aac tgc cgg gcc ccc tgc cac ctg cag atg gag gac ccc act     5136
Glu Arg Asn Cys Arg Ala Pro Cys His Leu Gln Met Glu Asp Pro Thr
    1700          1705          1710 ctg aaa gaa aac tat cgc ttc cat gca atc aat ggc tat gtg atg gat     5184
Leu Lys Glu Asn Tyr Arg Phe His Ala Ile Asn Gly Tyr Val Met Asp
         1715          1720          1725 aca ctc cct ggc tta gta atg gct cag aat caa agg atc cga tgg tat     5232
Thr Leu Pro Gly Leu Val Met Ala Gln Asn Gln Arg Ile Arg Trp Tyr
    1730          1735          1740 ctg ctc agc atg ggc agc aat gaa aat atc cat tcg att cat ttt agc     5280
Leu Leu Ser Met Gly Ser Asn Glu Asn Ile His Ser Ile His Phe Ser
1745          1750          1755          1760 gga cac gtg ttc agt gta cgg aaa aag gag gag tat aaa atg gcc gtg     5328

-continued

| | |
|---|---|
| Gly His Val Phe Ser Val Arg Lys Lys Glu Glu Tyr Lys Met Ala Val<br>                    1765                    1770                    1775 | |
| tac aat ctc tat ccg ggt gtc ttt gag aca gtg gaa atg cta ccg tcc<br>Tyr Asn Leu Tyr Pro Gly Val Phe Glu Thr Val Glu Met Leu Pro Ser<br>                    1780                    1785                    1790 | 5376 |
| aaa gtt gga att tgg cga ata gaa tgc ctg att ggc gag cac ctg caa<br>Lys Val Gly Ile Trp Arg Ile Glu Cys Leu Ile Gly Glu His Leu Gln<br>                    1795                    1800                    1805 | 5424 |
| gct ggg atg agc acg act ttc ctg gtg tac agc aag gag tgt cag gct<br>Ala Gly Met Ser Thr Thr Phe Leu Val Tyr Ser Lys Glu Cys Gln Ala<br>                    1810                    1815                    1820 | 5472 |
| cca ctg gga atg gct tct gga cgc att aga gat ttt cag atc aca gct<br>Pro Leu Gly Met Ala Ser Gly Arg Ile Arg Asp Phe Gln Ile Thr Ala<br>1825                    1830                    1835                    1840 | 5520 |
| tca gga cag tat gga cag tgg gcc cca aag ctg gcc aga ctt cat tat<br>Ser Gly Gln Tyr Gly Gln Trp Ala Pro Lys Leu Ala Arg Leu His Tyr<br>                    1845                    1850                    1855 | 5568 |
| tcc gga tca atc aat gcc tgg agc acc aag gat ccc cac tcc tgg atc<br>Ser Gly Ser Ile Asn Ala Trp Ser Thr Lys Asp Pro His Ser Trp Ile<br>                    1860                    1865                    1870 | 5616 |
| aag gtg gat ctg ttg gca cca atg atc att cac ggc atc atg acc cag<br>Lys Val Asp Leu Leu Ala Pro Met Ile Ile His Gly Ile Met Thr Gln<br>                    1875                    1880                    1885 | 5664 |
| ggt gcc cgt cag aag ttt tcc agc ctc tac atc tcc cag ttt atc atc<br>Gly Ala Arg Gln Lys Phe Ser Ser Leu Tyr Ile Ser Gln Phe Ile Ile<br>                    1890                    1895                    1900 | 5712 |
| atg tac agt ctt gac ggg agg aac tgg cag agt tac cga ggg aat tcc<br>Met Tyr Ser Leu Asp Gly Arg Asn Trp Gln Ser Tyr Arg Gly Asn Ser<br>1905                    1910                    1915                    1920 | 5760 |
| acg ggc acc tta atg gtc ttc ttt ggc aat gtg gac gca tct ggg att<br>Thr Gly Thr Leu Met Val Phe Phe Gly Asn Val Asp Ala Ser Gly Ile<br>                    1925                    1930                    1935 | 5808 |
| aaa cac aat att ttt aac cct ccg att gtg gct cgg tac atc cgt ttg<br>Lys His Asn Ile Phe Asn Pro Pro Ile Val Ala Arg Tyr Ile Arg Leu<br>                    1940                    1945                    1950 | 5856 |
| cac cca aca cat tac agc atc cgc agc act ctt cgc atg gag ttg atg<br>His Pro Thr His Tyr Ser Ile Arg Ser Thr Leu Arg Met Glu Leu Met<br>                    1955                    1960                    1965 | 5904 |
| ggc tgt gat tta aac agt tgc agc atg ccc ctg gga atg cag aat aaa<br>Gly Cys Asp Leu Asn Ser Cys Ser Met Pro Leu Gly Met Gln Asn Lys<br>1970                    1975                    1980 | 5952 |
| gcg ata tca gac tca cag atc acg gcc tcc tcc cac cta agc aat ata<br>Ala Ile Ser Asp Ser Gln Ile Thr Ala Ser Ser His Leu Ser Asn Ile<br>1985                    1990                    1995                    2000 | 6000 |
| ttt gcc acc tgg tct cct tca caa gcc cga ctt cac ctc cag ggg cgg<br>Phe Ala Thr Trp Ser Pro Ser Gln Ala Arg Leu His Leu Gln Gly Arg<br>                    2005                    2010                    2015 | 6048 |
| acg aat gcc tgg cga ccc cgg gtg agc agc gca gag gag tgg ctg cag<br>Thr Asn Ala Trp Arg Pro Arg Val Ser Ser Ala Glu Glu Trp Leu Gln<br>                    2020                    2025                    2030 | 6096 |
| gtg gac ctg cag aag acg gtg aag gtc aca ggc atc acc acc cag ggc<br>Val Asp Leu Gln Lys Thr Val Lys Val Thr Gly Ile Thr Thr Gln Gly<br>                    2035                    2040                    2045 | 6144 |
| gtg aag tcc ctg ctc agc agc atg tat gtg aag gag ttc ctc gtg tcc<br>Val Lys Ser Leu Leu Ser Ser Met Tyr Val Lys Glu Phe Leu Val Ser<br>2050                    2055                    2060 | 6192 |
| agt agt cag gac ggc cgc cgc tgg acc ctg ttt ctt cag gac ggc cac<br>Ser Ser Gln Asp Gly Arg Arg Trp Thr Leu Phe Leu Gln Asp Gly His<br>2065                    2070                    2075                    2080 | 6240 |

| | | | | | | | | | | | | | |
|---|---|---|---|---|---|---|---|---|---|---|---|---|---|
| acg | aag | gtt | ttt | cag | ggc | aat | cag | gac | tcc | tcc | acc | ccc | gtg gtg aac |
| Thr | Lys | Val | Phe | Gln | Gly | Asn | Gln | Asp | Ser | Ser | Thr | Pro | Val Val Asn |
| | | | 2085 | | | | 2090 | | | | | 2095 | |

6288

| | | | | | | | | | | | | |
|---|---|---|---|---|---|---|---|---|---|---|---|---|
| gct | ctg | gac | ccc | ccg | ctg | ttc | acg | cgc | tac | ctg | agg | atc cac ccc acg |
| Ala | Leu | Asp | Pro | Pro | Leu | Phe | Thr | Arg | Tyr | Leu | Arg | Ile His Pro Thr |
| | | 2100 | | | | | 2105 | | | | | 2110 |

6336

| | | | | | | | | | | | | |
|---|---|---|---|---|---|---|---|---|---|---|---|---|
| agc | tgg | gcg | cag | cac | atc | gcc | ctg | agg | ctc | gag | gtt | cta gga tgt gag |
| Ser | Trp | Ala | Gln | His | Ile | Ala | Leu | Arg | Leu | Glu | Val | Leu Gly Cys Glu |
| | | 2115 | | | | | 2120 | | | | | 2125 |

6384 gca cag gat ctc tac tga
Ala Gln Asp Leu Tyr
    2130

6402

<210> SEQ ID NO 30
<211> LENGTH: 2133
<212> TYPE: PRT
<213> ORGANISM: Porcine

<400> SEQUENCE: 30

Met Gln Leu Glu Leu Ser Thr Cys Val Phe Leu Cys Leu Leu Pro Leu
 1               5                  10                  15

Gly Phe Ser Ala Ile Arg Arg Tyr Tyr Leu Gly Ala Val Glu Leu Ser
                20                  25                  30

Trp Asp Tyr Arg Gln Ser Glu Leu Leu Arg Glu Leu His Val Asp Thr
            35                  40                  45

Arg Phe Pro Ala Thr Ala Pro Gly Ala Leu Pro Leu Gly Pro Ser Val
        50                  55                  60

Leu Tyr Lys Lys Thr Val Phe Val Glu Phe Thr Asp Gln Leu Phe Ser
65                  70                  75                  80

Val Ala Arg Pro Arg Pro Pro Trp Met Gly Leu Leu Gly Pro Thr Ile
                85                  90                  95

Gln Ala Glu Val Tyr Asp Thr Val Val Thr Leu Lys Asn Met Ala
            100                 105                 110

Ser His Pro Val Ser Leu His Ala Val Gly Val Ser Phe Trp Lys Ser
        115                 120                 125

Ser Glu Gly Ala Glu Tyr Glu Asp His Thr Ser Gln Arg Glu Lys Glu
    130                 135                 140

Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Arg Glu Arg
        195                 200                 205

Thr Gln Asn Leu His Glu Phe Val Leu Leu Phe Ala Val Phe Asp Glu
    210                 215                 220

Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
                245                 250                 255

Tyr Val Asn Arg Ser Leu Pro Gly Leu Ile Gly Cys His Lys Lys Ser
            260                 265                 270

Val Tyr Trp His Val Ile Gly Met Gly Thr Ser Pro Glu Val His Ser
        275                 280                 285

Ile Phe Leu Glu Gly His Thr Phe Leu Val Arg His His Arg Gln Ala

```
                  290                 295                 300
Ser Leu Glu Ile Ser Pro Leu Thr Phe Leu Thr Ala Gln Thr Phe Leu
305                 310                 315                 320

Met Asp Leu Gly Gln Phe Leu Leu Phe Cys His Ile Ser Ser His His
                325                 330                 335

His Gly Gly Met Glu Ala His Val Arg Val Glu Ser Cys Ala Glu Glu
                340                 345                 350

Pro Gln Leu Arg Arg Lys Ala Asp Glu Glu Asp Tyr Asp Asp Asn
                355                 360                 365

Leu Tyr Asp Ser Asp Met Asp Val Val Arg Leu Asp Gly Asp Val
370                 375                 380

Ser Pro Phe Ile Gln Ile Arg Ser Val Ala Lys Lys His Pro Lys Thr
385                 390                 395                 400

Trp Val His Tyr Ile Ser Ala Glu Glu Asp Trp Asp Tyr Ala Pro
                405                 410                 415

Ala Val Pro Ser Pro Ser Asp Arg Ser Tyr Lys Ser Leu Tyr Leu Asn
                420                 425                 430

Ser Gly Pro Gln Arg Ile Gly Arg Lys Tyr Lys Lys Ala Arg Phe Val
                435                 440                 445

Ala Tyr Thr Asp Val Thr Phe Lys Thr Arg Lys Ala Ile Pro Tyr Glu
                450                 455                 460

Ser Gly Ile Leu Gly Pro Leu Leu Tyr Gly Glu Val Gly Asp Thr Leu
465                 470                 475                 480

Leu Ile Ile Phe Lys Asn Lys Ala Ser Arg Pro Tyr Asn Ile Tyr Pro
                485                 490                 495

His Gly Ile Thr Asp Val Ser Ala Leu His Pro Gly Arg Leu Leu Lys
                500                 505                 510

Gly Trp Lys His Leu Lys Asp Met Pro Ile Leu Pro Gly Glu Thr Phe
                515                 520                 525

Lys Tyr Lys Trp Thr Val Thr Val Glu Asp Gly Pro Thr Lys Ser Asp
                530                 535                 540

Pro Arg Cys Leu Thr Arg Tyr Tyr Ser Ser Ser Ile Asn Leu Glu Lys
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Met Met Ser Asp Lys Arg Asn Val
                580                 585                 590

Ile Leu Phe Ser Val Phe Asp Glu Asn Gln Ser Trp Tyr Leu Ala Glu
                595                 600                 605

Asn Ile Gln Arg Phe Leu Pro Asn Pro Asp Gly Leu Gln Pro Gln Asp
                610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Val Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
                690                 695                 700

Gly Leu Trp Val Leu Gly Cys His Asn Ser Asp Leu Arg Asn Arg Gly
705                 710                 715                 720
```

-continued

```
Met Thr Ala Leu Leu Lys Val Tyr Ser Cys Asp Arg Asp Ile Gly Asp
                725                 730                 735

Tyr Tyr Asp Asn Thr Tyr Glu Asp Ile Pro Gly Phe Leu Leu Ser Gly
            740                 745                 750

Lys Asn Val Ile Glu Pro Arg Ser Phe Ala Gln Asn Ser Arg Pro Pro
            755                 760             765

Ser Ala Ser Gln Lys Gln Phe Gln Thr Ile Thr Ser Pro Glu Asp Asp
    770                 775                 780

Val Glu Leu Asp Pro Gln Ser Gly Glu Arg Thr Gln Ala Leu Glu Glu
785                 790                 795                 800

Leu Ser Val Pro Ser Gly Asp Gly Ser Met Leu Leu Gly Gln Asn Pro
                805                 810                 815

Ala Pro His Gly Ser Ser Ser Asp Leu Gln Glu Ala Arg Asn Glu
                820                 825             830

Ala Asp Asp Tyr Leu Pro Gly Ala Arg Glu Arg Gly Thr Ala Pro Ser
            835                 840                 845

Ala Ala Ala Arg Leu Arg Pro Glu Leu His His Ser Ala Glu Arg Val
    850                 855                 860

Leu Thr Pro Glu Pro Glu Lys Glu Leu Lys Lys Leu Asp Ser Lys Met
865                 870                 875                 880

Ser Ser Ser Ser Asp Leu Leu Lys Thr Ser Pro Thr Ile Pro Ser Asp
                885                 890                 895

Thr Leu Ser Ala Glu Thr Glu Arg Thr His Ser Leu Gly Pro Pro His
            900                 905                 910

Pro Gln Val Asn Phe Arg Ser Gln Leu Gly Ala Ile Val Leu Gly Lys
            915                 920                 925

Asn Ser Ser His Phe Ile Gly Ala Gly Val Pro Leu Gly Ser Thr Glu
    930                 935                 940

Glu Asp His Glu Ser Ser Leu Gly Glu Asn Val Ser Pro Val Glu Ser
945                 950                 955                 960

Asp Gly Ile Phe Glu Lys Glu Arg Ala His Gly Pro Ala Ser Leu Thr
                965                 970                 975

Lys Asp Asp Val Leu Phe Lys Val Asn Ile Ser Leu Val Lys Thr Asn
            980                 985                 990

Lys Ala Arg Val Tyr Leu Lys Thr Asn Arg Lys Ile His Ile Asp Asp
            995                 1000                1005

Ala Ala Leu Leu Thr Glu Asn Arg Ala Ser Ala Thr Phe Met Asp Lys
    1010                1015                1020

Asn Thr Thr Ala Ser Gly Leu Asn His Val Ser Asn Trp Ile Lys Gly
1025                1030                1035                1040

Pro Leu Gly Lys Asn Pro Leu Ser Ser Glu Arg Gly Pro Ser Pro Glu
                1045                1050                1055

Leu Leu Thr Ser Ser Gly Ser Gly Lys Ser Val Lys Gly Gln Ser Ser
                1060                1065                1070

Gly Gln Gly Arg Ile Arg Val Ala Val Glu Glu Glu Leu Ser Lys
            1075                1080                1085

Gly Lys Glu Met Met Leu Pro Asn Ser Glu Leu Thr Phe Leu Thr Asn
    1090                1095                1100

Ser Ala Asp Val Gln Gly Asn Asp Thr His Ser Gln Gly Lys Lys Ser
1105                1110                1115                1120

Arg Glu Glu Met Glu Arg Arg Lys Leu Val Gln Glu Lys Val Asp
                1125                1130                1135
```

-continued

```
Leu Pro Gln Val Tyr Thr Ala Thr Gly Thr Lys Asn Phe Leu Arg Asn
        1140                1145                1150

Ile Phe His Gln Ser Thr Glu Pro Ser Val Glu Gly Phe Asp Gly Gly
    1155                1160                1165

Ser His Ala Pro Val Pro Gln Asp Ser Arg Ser Leu Asn Asp Ser Ala
1170                1175                1180

Glu Arg Ala Glu Thr His Ile Ala His Phe Ser Ala Ile Arg Glu Glu
1185                1190                1195                1200

Ala Pro Leu Glu Ala Pro Gly Asn Arg Thr Gly Pro Gly Pro Arg Ser
        1205                1210                1215

Ala Val Pro Arg Arg Val Lys Gln Ser Leu Lys Gln Ile Arg Leu Pro
        1220                1225                1230

Leu Glu Glu Ile Lys Pro Glu Arg Gly Val Val Leu Asn Ala Thr Ser
        1235                1240                1245

Thr Arg Trp Ser Glu Ser Ser Pro Ile Leu Gln Gly Ala Lys Arg Asn
        1250                1255                1260

Asn Leu Ser Leu Pro Phe Leu Thr Leu Glu Met Ala Gly Gly Gln Gly
1265                1270                1275                1280

Lys Ile Ser Ala Leu Gly Lys Ser Ala Ala Gly Pro Leu Ala Ser Gly
        1285                1290                1295

Lys Leu Glu Lys Ala Val Leu Ser Ser Ala Gly Leu Ser Glu Ala Ser
        1300                1305                1310

Gly Lys Ala Glu Phe Leu Pro Lys Val Arg Val His Arg Glu Asp Leu
        1315                1320                1325

Leu Pro Gln Lys Thr Ser Asn Val Ser Cys Ala His Gly Asp Leu Gly
        1330                1335                1340

Gln Glu Ile Phe Leu Gln Lys Thr Arg Gly Pro Val Asn Leu Asn Lys
1345                1350                1355                1360

Val Asn Arg Pro Gly Arg Thr Pro Ser Lys Leu Leu Gly Pro Pro Met
            1365                1370                1375

Pro Lys Glu Trp Glu Ser Leu Glu Lys Ser Pro Lys Ser Thr Ala Leu
        1380                1385                1390

Arg Thr Lys Asp Ile Ile Ser Leu Pro Leu Asp Arg His Glu Ser Asn
        1395                1400                1405

His Ser Ile Ala Ala Lys Asn Glu Gly Gln Ala Glu Thr Gln Arg Glu
    1410                1415                1420

Ala Ala Trp Thr Lys Gln Gly Gly Pro Gly Arg Leu Cys Ala Pro Lys
1425                1430                1435                1440

Pro Pro Val Leu Arg Arg His Gln Arg Asp Ile Ser Leu Pro Thr Phe
            1445                1450                1455

Gln Pro Glu Glu Asp Lys Met Asp Tyr Asp Asp Ile Phe Ser Thr Glu
        1460                1465                1470

Thr Lys Gly Glu Asp Phe Asp Ile Tyr Gly Glu Asp Glu Asn Gln Asp
        1475                1480                1485

Pro Arg Ser Phe Gln Lys Arg Thr Arg His Tyr Phe Ile Ala Ala Val
    1490                1495                1500

Glu Gln Leu Trp Asp Tyr Gly Met Ser Glu Ser Pro Arg Ala Leu Arg
1505                1510                1515                1520

Asn Arg Ala Gln Asn Gly Glu Val Pro Arg Phe Lys Lys Val Val Phe
            1525                1530                1535

Arg Glu Phe Ala Asp Gly Ser Phe Thr Gln Pro Ser Tyr Arg Gly Glu
        1540                1545                1550

Leu Asn Lys His Leu Gly Leu Leu Gly Pro Tyr Ile Arg Ala Glu Val
```

-continued

```
                1555               1560               1565

Glu Asp Asn Ile Met Val Thr Phe Lys Asn Gln Ala Ser Arg Pro Tyr
            1570               1575               1580

Ser Phe Tyr Ser Ser Leu Ile Ser Tyr Pro Asp Asp Gln Glu Gln Gly
1585               1590               1595               1600

Ala Glu Pro Arg His Asn Phe Val Gln Pro Asn Glu Thr Arg Thr Tyr
            1605               1610               1615

Phe Trp Lys Val Gln His His Met Ala Pro Thr Glu Asp Glu Phe Asp
            1620               1625               1630

Cys Lys Ala Trp Ala Tyr Phe Ser Asp Val Asp Leu Glu Lys Asp Val
            1635               1640               1645

His Ser Gly Leu Ile Gly Pro Leu Leu Ile Cys Arg Ala Asn Thr Leu
            1650               1655               1660

Asn Ala Ala His Gly Arg Gln Val Thr Val Gln Glu Phe Ala Leu Phe
1665               1670               1675               1680

Phe Thr Ile Phe Asp Glu Thr Lys Ser Trp Tyr Phe Thr Glu Asn Val
            1685               1690               1695

Glu Arg Asn Cys Arg Ala Pro Cys His Leu Gln Met Glu Asp Pro Thr
            1700               1705               1710

Leu Lys Glu Asn Tyr Arg Phe His Ala Ile Asn Gly Tyr Val Met Asp
            1715               1720               1725

Thr Leu Pro Gly Leu Val Met Ala Gln Asn Gln Arg Ile Arg Trp Tyr
            1730               1735               1740

Leu Leu Ser Met Gly Ser Asn Glu Asn Ile His Ser Ile His Phe Ser
1745               1750               1755               1760

Gly His Val Phe Ser Val Arg Lys Lys Glu Glu Tyr Lys Met Ala Val
            1765               1770               1775

Tyr Asn Leu Tyr Pro Gly Val Phe Glu Thr Val Glu Met Leu Pro Ser
            1780               1785               1790

Lys Val Gly Ile Trp Arg Ile Glu Cys Leu Ile Gly Glu His Leu Gln
            1795               1800               1805

Ala Gly Met Ser Thr Thr Phe Leu Val Tyr Ser Lys Glu Cys Gln Ala
            1810               1815               1820

Pro Leu Gly Met Ala Ser Gly Arg Ile Arg Asp Phe Gln Ile Thr Ala
1825               1830               1835               1840

Ser Gly Gln Tyr Gly Gln Trp Ala Pro Lys Leu Ala Arg Leu His Tyr
            1845               1850               1855

Ser Gly Ser Ile Asn Ala Trp Ser Thr Lys Asp Pro His Ser Trp Ile
            1860               1865               1870

Lys Val Asp Leu Leu Ala Pro Met Ile Ile His Gly Ile Met Thr Gln
            1875               1880               1885

Gly Ala Arg Gln Lys Phe Ser Ser Leu Tyr Ile Ser Gln Phe Ile Ile
            1890               1895               1900

Met Tyr Ser Leu Asp Gly Arg Asn Trp Gln Ser Tyr Arg Gly Asn Ser
1905               1910               1915               1920

Thr Gly Thr Leu Met Val Phe Phe Gly Asn Val Asp Ala Ser Gly Ile
            1925               1930               1935

Lys His Asn Ile Phe Asn Pro Pro Ile Val Ala Arg Tyr Ile Arg Leu
            1940               1945               1950

His Pro Thr His Tyr Ser Ile Arg Ser Thr Leu Arg Met Glu Leu Met
            1955               1960               1965

Gly Cys Asp Leu Asn Ser Cys Ser Met Pro Leu Gly Met Gln Asn Lys
1970               1975               1980
```

```
Ala Ile Ser Asp Ser Gln Ile Thr Ala Ser Ser His Leu Ser Asn Ile
1985                1990                1995                2000

Phe Ala Thr Trp Ser Pro Ser Gln Ala Arg Leu His Leu Gln Gly Arg
            2005                2010                2015

Thr Asn Ala Trp Arg Pro Arg Val Ser Ser Ala Glu Glu Trp Leu Gln
            2020                2025                2030

Val Asp Leu Gln Lys Thr Val Lys Val Thr Gly Ile Thr Thr Gln Gly
            2035                2040                2045

Val Lys Ser Leu Leu Ser Ser Met Tyr Val Lys Glu Phe Leu Val Ser
    2050                2055                2060

Ser Ser Gln Asp Gly Arg Arg Trp Thr Leu Phe Leu Gln Asp Gly His
2065                2070                2075                2080

Thr Lys Val Phe Gln Gly Asn Gln Asp Ser Ser Thr Pro Val Val Asn
            2085                2090                2095

Ala Leu Asp Pro Pro Leu Phe Thr Arg Tyr Leu Arg Ile His Pro Thr
            2100                2105                2110

Ser Trp Ala Gln His Ile Ala Leu Arg Leu Glu Val Leu Gly Cys Glu
        2115                2120                2125

Ala Gln Asp Leu Tyr
    2130

<210> SEQ ID NO 31
<211> LENGTH: 19
<212> TYPE: PRT
<213> ORGANISM: Homo sapiens

<400> SEQUENCE: 31

Met Gln Ile Glu Leu Ser Thr Cys Phe Phe Leu Cys Leu Leu Arg Phe
1               5                   10                  15

Cys Phe Ser

<210> SEQ ID NO 32
<211> LENGTH: 24
<212> TYPE: PRT
<213> ORGANISM: Artificial Sequence
<220> FEATURE:
<223> OTHER INFORMATION: Description of Artificial Sequence:linker

<400> SEQUENCE: 32

Ser Phe Ala Gln Asn Ser Arg Pro Pro Ser Ala Ser Ala Pro Lys Pro
1               5                   10                  15

Pro Val Leu Arg Arg His Gln Arg
            20

<210> SEQ ID NO 33
<211> LENGTH: 105
<212> TYPE: DNA
<213> ORGANISM: Artificial Sequence
<220> FEATURE:
<223> OTHER INFORMATION: Description of Artificial Sequence:linker

<400> SEQUENCE: 33
gtcattgaac ctaggagctt tgcccagaat tcaagacccc ctagtgcgag cgctccaaag     60
cctccggtcc tgcgacggca tcagagggac ataagccttc ctact                    105

<210> SEQ ID NO 34
<211> LENGTH: 21
<212> TYPE: DNA
<213> ORGANISM: Artificial Sequence
```

<220> FEATURE:
<223> OTHER INFORMATION: Description of Artificial Sequence:
      oligonucleotide primer

<400> SEQUENCE: 34
gaggaaaacc agatgatgtc a                                            21

<210> SEQ ID NO 35
<211> LENGTH: 60
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 35
ctttggagcg ctcgcactag ggggtcttga attctgggca aagctcctag gttcaatgac    60

<210> SEQ ID NO 36
<211> LENGTH: 66
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 36
cctagtgcga gcgctccaaa gcctccggtc ctgcgacggc atcagaggga cataagcctt    60
cctact                                                              66

<210> SEQ ID NO 37
<211> LENGTH: 4404
<212> TYPE: DNA
<213> ORGANISM: Porcine
<220> FEATURE:
<221> NAME/KEY: CDS
<222> LOCATION: (1)..(4401)

<400> SEQUENCE: 37

| atg | cag | cta | gag | ctc | tcc | acc | tgt | gtc | ttt | ctg | tgt | ctc | ttg | cca | ctc | 48 |
| Met | Gln | Leu | Glu | Leu | Ser | Thr | Cys | Val | Phe | Leu | Cys | Leu | Leu | Pro | Leu | |
| 1   |     |     |     | 5   |     |     |     |     | 10  |     |     |     |     | 15  |     | |

| ggc | ttt | agt | gcc | atc | agg | aga | tac | tac | ctg | ggc | gca | gtg | gaa | ctg | tcc | 96 |
| Gly | Phe | Ser | Ala | Ile | Arg | Arg | Tyr | Tyr | Leu | Gly | Ala | Val | Glu | Leu | Ser | |
|     |     |     | 20  |     |     |     |     | 25  |     |     |     |     | 30  |     |     | |

| tgg | gac | tac | cgg | caa | agt | gaa | ctc | ctc | cgt | gag | ctg | cac | gtg | gac | acc | 144 |
| Trp | Asp | Tyr | Arg | Gln | Ser | Glu | Leu | Leu | Arg | Glu | Leu | His | Val | Asp | Thr | |
|     | 35  |     |     |     |     | 40  |     |     |     |     | 45  |     |     |     |     | |

| aga | ttt | cct | gct | aca | gcg | cca | gga | gct | ctt | ccg | ttg | ggc | ccg | tca | gtc | 192 |
| Arg | Phe | Pro | Ala | Thr | Ala | Pro | Gly | Ala | Leu | Pro | Leu | Gly | Pro | Ser | Val | |
| 50  |     |     |     |     | 55  |     |     |     |     | 60  |     |     |     |     |     | |

| ctg | tac | aaa | aag | act | gtg | ttc | gta | gag | ttc | acg | gat | caa | ctt | ttc | agc | 240 |
| Leu | Tyr | Lys | Lys | Thr | Val | Phe | Val | Glu | Phe | Thr | Asp | Gln | Leu | Phe | Ser | |
| 65  |     |     |     |     | 70  |     |     |     |     | 75  |     |     |     |     | 80  | |

| gtt | gcc | agg | ccc | agg | cca | cca | tgg | atg | ggt | ctg | ctg | ggt | cct | acc | atc | 288 |
| Val | Ala | Arg | Pro | Arg | Pro | Pro | Trp | Met | Gly | Leu | Leu | Gly | Pro | Thr | Ile | |
|     |     |     |     | 85  |     |     |     |     | 90  |     |     |     |     | 95  |     | |

| cag | gct | gag | gtt | tac | gac | acg | gtg | gtc | gtt | acc | ctg | aag | aac | atg | gct | 336 |
| Gln | Ala | Glu | Val | Tyr | Asp | Thr | Val | Val | Val | Thr | Leu | Lys | Asn | Met | Ala | |
|     |     |     | 100 |     |     |     |     | 105 |     |     |     |     | 110 |     |     | |

| tct | cat | ccc | gtt | agt | ctt | cac | gct | gtc | ggc | gtc | tcc | ttc | tgg | aaa | tct | 384 |
| Ser | His | Pro | Val | Ser | Leu | His | Ala | Val | Gly | Val | Ser | Phe | Trp | Lys | Ser | |
|     | 115 |     |     |     |     | 120 |     |     |     |     | 125 |     |     |     |     | |

|                                                                                                                          |      |
|--------------------------------------------------------------------------------------------------------------------------|------|
| tcc gaa ggc gct gaa tat gag gat cac acc agc caa agg gag aag gaa<br>Ser Glu Gly Ala Glu Tyr Glu Asp His Thr Ser Gln Arg Glu Lys Glu<br>130                 135                 140                | 432  |
| gac gat aaa gtc ctt ccc ggt aaa agc caa acc tac gtc tgg cag gtc<br>Asp Asp Lys Val Leu Pro Gly Lys Ser Gln Thr Tyr Val Trp Gln Val<br>145                 150                 155                 160 | 480  |
| ctg aaa gaa aat ggt cca aca gcc tct gac cca cca tgt ctt acc tac<br>Leu Lys Glu Asn Gly Pro Thr Ala Ser Asp Pro Pro Cys Leu Thr Tyr<br>                165                 170                 175     | 528  |
| tca tac ctg tct cac gtg gac ctg gtg aaa gac ctg aat tcg ggc ctc<br>Ser Tyr Leu Ser His Val Asp Leu Val Lys Asp Leu Asn Ser Gly Leu<br>            180                 185                 190        | 576  |
| att gga gcc ctg ctg gtt tgt aga gaa ggg agt ctg acc aga gaa agg<br>Ile Gly Ala Leu Leu Val Cys Arg Glu Gly Ser Leu Thr Arg Glu Arg<br>            195                 200                 205        | 624  |
| acc cag aac ctg cac gaa ttt gta cta ctt ttt gct gtc ttt gat gaa<br>Thr Gln Asn Leu His Glu Phe Val Leu Leu Phe Ala Val Phe Asp Glu<br>            210                 215                 220        | 672  |
| ggg aaa agt tgg cac tca gca aga aat gac tcc tgg aca cgg gcc atg<br>Gly Lys Ser Trp His Ser Ala Arg Asn Asp Ser Trp Thr Arg Ala Met<br>225                 230                 235                 240 | 720  |
| gat ccc gca cct gcc agg gcc cag cct gca atg cac aca gtc aat ggc<br>Asp Pro Ala Pro Ala Arg Ala Gln Pro Ala Met His Thr Val Asn Gly<br>                245                 250                 255     | 768  |
| tat gtc aac agg tct ctg cca ggt ctg atc gga tgt cat aag aaa tca<br>Tyr Val Asn Arg Ser Leu Pro Gly Leu Ile Gly Cys His Lys Lys Ser<br>            260                 265                 270        | 816  |
| gtc tac tgg cac gtg att gga atg ggc acc agc ccg gaa gtg cac tcc<br>Val Tyr Trp His Val Ile Gly Met Gly Thr Ser Pro Glu Val His Ser<br>            275                 280                 285        | 864  |
| att ttt ctt gaa ggc cac acg ttt ctc gtg agg cac cat cgc cag gct<br>Ile Phe Leu Glu Gly His Thr Phe Leu Val Arg His His Arg Gln Ala<br>            290                 295                 300        | 912  |
| tcc ttg gag atc tcg cca cta act ttc ctc act gct cag aca ttc ctg<br>Ser Leu Glu Ile Ser Pro Leu Thr Phe Leu Thr Ala Gln Thr Phe Leu<br>305                 310                 315                 320 | 960  |
| atg gac ctt ggc cag ttc cta ctg ttt tgt cat atc tct tcc cac cac<br>Met Asp Leu Gly Gln Phe Leu Leu Phe Cys His Ile Ser Ser His His<br>                325                 330                 335     | 1008 |
| cat ggt ggc atg gag gct cac gtc aga gta gaa agc tgc gcc gag gag<br>His Gly Gly Met Glu Ala His Val Arg Val Glu Ser Cys Ala Glu Glu<br>            340                 345                 350        | 1056 |
| ccc cag ctg cgg agg aaa gct gat gaa gag gaa gat tat gat gac aat<br>Pro Gln Leu Arg Arg Lys Ala Asp Glu Glu Glu Asp Tyr Asp Asp Asn<br>            355                 360                 365        | 1104 |
| ttg tac gac tcg gac atg gac gtg gtc cgg ctc gat ggt gac gac gtg<br>Leu Tyr Asp Ser Asp Met Asp Val Val Arg Leu Asp Gly Asp Asp Val<br>370                 375                 380                     | 1152 |
| tct ccc ttt atc caa atc cgc tcg gtt gcc aag aag cat ccc aaa acc<br>Ser Pro Phe Ile Gln Ile Arg Ser Val Ala Lys Lys His Pro Lys Thr<br>385                 390                 395                 400 | 1200 |
| tgg gtg cac tac atc tct gca gag gag gag gac tgg gac tac gcc ccc<br>Trp Val His Tyr Ile Ser Ala Glu Glu Glu Asp Trp Asp Tyr Ala Pro<br>                405                 410                 415     | 1248 |
| gcg gtc ccc agc ccc agt gac aga agt tat aaa agt ctc tac ttg aac<br>Ala Val Pro Ser Pro Ser Asp Arg Ser Tyr Lys Ser Leu Tyr Leu Asn<br>            420                 425                 430        | 1296 |
| agt ggt cct cag cga att ggt agg aaa tac aaa aaa gct cga ttc gtc<br>Ser Gly Pro Gln Arg Ile Gly Arg Lys Tyr Lys Lys Ala Arg Phe Val<br>            435                 440                 445        | 1344 |

-continued

```
gct tac acg gat gta aca ttt aag act cgt aaa gct att ccg tat gaa      1392
Ala Tyr Thr Asp Val Thr Phe Lys Thr Arg Lys Ala Ile Pro Tyr Glu
    450                 455                 460 tca gga atc ctg gga cct tta ctt tat gga gaa gtt gga gac aca ctt      1440
Ser Gly Ile Leu Gly Pro Leu Leu Tyr Gly Glu Val Gly Asp Thr Leu
465                 470                 475                 480 ttg att ata ttt aag aat aaa gcg agc cga cca tat aac atc tac cct      1488
Leu Ile Ile Phe Lys Asn Lys Ala Ser Arg Pro Tyr Asn Ile Tyr Pro
                485                 490                 495 cat gga atc act gat gtc agc gct ttg cac cca ggg aga ctt cta aaa      1536
His Gly Ile Thr Asp Val Ser Ala Leu His Pro Gly Arg Leu Leu Lys
            500                 505                 510 ggt tgg aaa cat ttg aaa gac atg cca att ctg cca gga gag act ttc      1584
Gly Trp Lys His Leu Lys Asp Met Pro Ile Leu Pro Gly Glu Thr Phe
        515                 520                 525 aag tat aaa tgg aca gtg act gtg gaa gat ggg cca acc aag tcc gat      1632
Lys Tyr Lys Trp Thr Val Thr Val Glu Asp Gly Pro Thr Lys Ser Asp
    530                 535                 540 cct cgg tgc ctg acc cgc tac tac tcg agc tcc att aat cta gag aaa      1680
Pro Arg Cys Leu Thr Arg Tyr Tyr Ser Ser Ser Ile Asn Leu Glu Lys
545                 550                 555                 560 gat ctg gct tcg gga ctc att ggc cct ctc ctc atc tgc tac aaa gaa      1728
Asp Leu Ala Ser Gly Leu Ile Gly Pro Leu Leu Ile Cys Tyr Lys Glu
                565                 570                 575 tct gta gac caa aga gga aac cag atg atg tca gac aag aga aac gtc      1776
Ser Val Asp Gln Arg Gly Asn Gln Met Met Ser Asp Lys Arg Asn Val
            580                 585                 590 atc ctg ttt tct gta ttc gat gag aat caa agc tgg tac ctc gca gag      1824
Ile Leu Phe Ser Val Phe Asp Glu Asn Gln Ser Trp Tyr Leu Ala Glu
        595                 600                 605 aat att cag cgc ttc ctc ccc aat ccg gat gga tta cag ccc cag gat      1872
Asn Ile Gln Arg Phe Leu Pro Asn Pro Asp Gly Leu Gln Pro Gln Asp
    610                 615                 620 cca gag ttc caa gct tct aac atc atg cac agc atc aat ggc tat gtt      1920
Pro Glu Phe Gln Ala Ser Asn Ile Met His Ser Ile Asn Gly Tyr Val
625                 630                 635                 640 ttt gat agc ttg cag ctg tcg gtt tgt ttg cac gag gtg gca tac tgg      1968
Phe Asp Ser Leu Gln Leu Ser Val Cys Leu His Glu Val Ala Tyr Trp
                645                 650                 655 tac att cta agt gtt gga gca cag acg gac ttc ctc tcc gtc ttc ttc      2016
Tyr Ile Leu Ser Val Gly Ala Gln Thr Asp Phe Leu Ser Val Phe Phe
            660                 665                 670 tct ggc tac acc ttc aaa cac aaa atg gtc tat gaa gac aca ctc acc      2064
Ser Gly Tyr Thr Phe Lys His Lys Met Val Tyr Glu Asp Thr Leu Thr
        675                 680                 685 ctg ttc ccc ttc tca gga gaa acg gtc ttc atg tca atg gaa aac cca      2112
Leu Phe Pro Phe Ser Gly Glu Thr Val Phe Met Ser Met Glu Asn Pro
    690                 695                 700 ggt ctc tgg gtc ctt ggg tgc cac aac tca gac ttg cgg aac aga ggg      2160
Gly Leu Trp Val Leu Gly Cys His Asn Ser Asp Leu Arg Asn Arg Gly
705                 710                 715                 720 atg aca gcc tta ctg aag gtg tat agt tgt gac agg gac att ggt gat      2208
Met Thr Ala Leu Leu Lys Val Tyr Ser Cys Asp Arg Asp Ile Gly Asp
                725                 730                 735 tat tat gac aac act tat gaa gat att cca ggc ttc ttg ctg agt gga      2256
Tyr Tyr Asp Asn Thr Tyr Glu Asp Ile Pro Gly Phe Leu Leu Ser Gly
            740                 745                 750 aag aat gtc att gaa cct agg agc ttt gcc cag aat tca aga ccc cct      2304
Lys Asn Val Ile Glu Pro Arg Ser Phe Ala Gln Asn Ser Arg Pro Pro
```

-continued

```
            755                 760                 765
agt gcg agc gct cca aag cct ccg gtc ctg cga cgg cat cag agg gac          2352
Ser Ala Ser Ala Pro Lys Pro Pro Val Leu Arg Arg His Gln Arg Asp
    770                 775                 780 ata agc ctt cct act ttt cag ccg gag gaa gac aaa atg gac tat gat          2400
Ile Ser Leu Pro Thr Phe Gln Pro Glu Glu Asp Lys Met Asp Tyr Asp
785                 790                 795                 800 gat atc ttc tca act gaa acg aag gga gaa gat ttt gac att tac ggt          2448
Asp Ile Phe Ser Thr Glu Thr Lys Gly Glu Asp Phe Asp Ile Tyr Gly
                805                 810                 815 gag gat gaa aat cag gac cct cgc agc ttt cag aag aga acc cga cac          2496
Glu Asp Glu Asn Gln Asp Pro Arg Ser Phe Gln Lys Arg Thr Arg His
        820                 825                 830 tat ttc att gct gcg gtg gag cag ctc tgg gat tac ggg atg agc gaa          2544
Tyr Phe Ile Ala Ala Val Glu Gln Leu Trp Asp Tyr Gly Met Ser Glu
            835                 840                 845 tcc ccc cgg gcg cta aga aac agg gct cag aac gga gag gtg cct cgg          2592
Ser Pro Arg Ala Leu Arg Asn Arg Ala Gln Asn Gly Glu Val Pro Arg
    850                 855                 860 ttc aag aag gtg gtc ttc cgg gaa ttt gct gac ggc tcc ttc acg cag          2640
Phe Lys Lys Val Val Phe Arg Glu Phe Ala Asp Gly Ser Phe Thr Gln
865                 870                 875                 880 ccg tcg tac cgc ggg gaa ctc aac aaa cac ttg ggg ctc ttg gga ccc          2688
Pro Ser Tyr Arg Gly Glu Leu Asn Lys His Leu Gly Leu Leu Gly Pro
                885                 890                 895 tac atc aga gcg gaa gtt gaa gac aac atc atg gta act ttc aaa aac          2736
Tyr Ile Arg Ala Glu Val Glu Asp Asn Ile Met Val Thr Phe Lys Asn
        900                 905                 910 cag gcg tct cgt ccc tat tcc ttc tac tcg agc ctt att tct tat ccg          2784
Gln Ala Ser Arg Pro Tyr Ser Phe Tyr Ser Ser Leu Ile Ser Tyr Pro
            915                 920                 925 gat gat cag gag caa ggg gca gaa cct cga cac aac ttc gtc cag cca          2832
Asp Asp Gln Glu Gln Gly Ala Glu Pro Arg His Asn Phe Val Gln Pro
    930                 935                 940 aat gaa acc aga act tac ttt tgg aaa gtg cag cat cac atg gca ccc          2880
Asn Glu Thr Arg Thr Tyr Phe Trp Lys Val Gln His His Met Ala Pro
945                 950                 955                 960 aca gaa gac gag ttt gac tgc aaa gcc tgg gcc tac ttt tct gat gtt          2928
Thr Glu Asp Glu Phe Asp Cys Lys Ala Trp Ala Tyr Phe Ser Asp Val
                965                 970                 975 gac ctg gaa aaa gat gtg cac tca ggc ttg atc ggc ccc ctt ctg atc          2976
Asp Leu Glu Lys Asp Val His Ser Gly Leu Ile Gly Pro Leu Leu Ile
        980                 985                 990 tgc cgc gcc aac acc ctg aac gct gct cac ggt aga caa gtg acc gtg          3024
Cys Arg Ala Asn Thr Leu Asn Ala Ala His Gly Arg Gln Val Thr Val
            995                 1000                1005 caa gaa ttt gct ctg ttt ttc act att ttt gat gag aca aag agc tgg          3072
Gln Glu Phe Ala Leu Phe Phe Thr Ile Phe Asp Glu Thr Lys Ser Trp
    1010                1015                1020 tac ttc act gaa aat gtg gaa agg aac tgc cgg gcc ccc tgc cat ctg          3120
Tyr Phe Thr Glu Asn Val Glu Arg Asn Cys Arg Ala Pro Cys His Leu
1025                1030                1035                1040 cag atg gag gac ccc act ctg aaa gaa aac tat cgc ttc cat gca atc          3168
Gln Met Glu Asp Pro Thr Leu Lys Glu Asn Tyr Arg Phe His Ala Ile
                1045                1050                1055 aat ggc tat gtg atg gat aca ctc cct ggc tta gta atg gct cag aat          3216
Asn Gly Tyr Val Met Asp Thr Leu Pro Gly Leu Val Met Ala Gln Asn
        1060                1065                1070 caa agg atc cga tgg tat ctg ctc agc atg ggc agc aat gaa aat atc          3264
```

```
                                                          -continued

Gln Arg Ile Arg Trp Tyr Leu Leu Ser Met Gly Ser Asn Glu Asn Ile
    1075                1080                1085 cat tcg att cat ttt agc gga cac gtg ttc agt gta cgg aaa aag gag     3312
His Ser Ile His Phe Ser Gly His Val Phe Ser Val Arg Lys Lys Glu
    1090                1095                1100 gag tat aaa atg gcc gtg tac aat ctc tat ccg ggt gtc ttt gag aca     3360
Glu Tyr Lys Met Ala Val Tyr Asn Leu Tyr Pro Gly Val Phe Glu Thr
1105                1110                1115                1120 gtg gaa atg cta ccg tcc aaa gtt gga att tgg cga ata gaa tgc ctg     3408
Val Glu Met Leu Pro Ser Lys Val Gly Ile Trp Arg Ile Glu Cys Leu
                1125                1130                1135 att ggc gag cac ctg caa gct ggg atg agc acg act ttc ctg gtg tac     3456
Ile Gly Glu His Leu Gln Ala Gly Met Ser Thr Thr Phe Leu Val Tyr
            1140                1145                1150 agc aag gag tgt cag gct cca ctg gga atg gct tct gga cgc att aga     3504
Ser Lys Glu Cys Gln Ala Pro Leu Gly Met Ala Ser Gly Arg Ile Arg
        1155                1160                1165 gat ttt cag atc aca gct tca gga cag tat gga cag tgg gcc cca aag     3552
Asp Phe Gln Ile Thr Ala Ser Gly Gln Tyr Gly Gln Trp Ala Pro Lys
    1170                1175                1180 ctg gcc aga ctt cat tat tcc gga tca atc aat gcc tgg agc acc aag     3600
Leu Ala Arg Leu His Tyr Ser Gly Ser Ile Asn Ala Trp Ser Thr Lys
1185                1190                1195                1200 gat ccc cac tcc tgg atc aag gtg gat ctg ttg gca cca atg atc att     3648
Asp Pro His Ser Trp Ile Lys Val Asp Leu Leu Ala Pro Met Ile Ile
                1205                1210                1215 cac ggc atc atg acc cag ggt gcc cgt cag aag ttt tcc agc ctc tac     3696
His Gly Ile Met Thr Gln Gly Ala Arg Gln Lys Phe Ser Ser Leu Tyr
            1220                1225                1230 atc tcc cag ttt atc atc atg tac agt ctt gac ggg agg aac tgg cag     3744
Ile Ser Gln Phe Ile Ile Met Tyr Ser Leu Asp Gly Arg Asn Trp Gln
        1235                1240                1245 agt tac cga ggg aat tcc acg ggc acc tta atg gtc ttc ttt ggc aat     3792
Ser Tyr Arg Gly Asn Ser Thr Gly Thr Leu Met Val Phe Phe Gly Asn
    1250                1255                1260 gtg gac gca tct ggg att aaa cac aat att ttt aac cct ccg att gtg     3840
Val Asp Ala Ser Gly Ile Lys His Asn Ile Phe Asn Pro Pro Ile Val
1265                1270                1275                1280 gct cgg tac atc cgt ttg cac cca aca cat tac agc atc cgc agc act     3888
Ala Arg Tyr Ile Arg Leu His Pro Thr His Tyr Ser Ile Arg Ser Thr
                1285                1290                1295 ctt cgc atg gag ttg atg ggc tgt gat tta aac agt tgc agc atg ccc     3936
Leu Arg Met Glu Leu Met Gly Cys Asp Leu Asn Ser Cys Ser Met Pro
            1300                1305                1310 ctg gga atg cag aat aaa gcg ata tca gac tca cag atc acg gcc tcc     3984
Leu Gly Met Gln Asn Lys Ala Ile Ser Asp Ser Gln Ile Thr Ala Ser
        1315                1320                1325 tcc cac cta agc aat ata ttt gcc acc tgg tct cct tca caa gcc cga     4032
Ser His Leu Ser Asn Ile Phe Ala Thr Trp Ser Pro Ser Gln Ala Arg
    1330                1335                1340 ctt cac ctc cag ggg cgg acg aat gcc tgg cga ccc cgg gtg agc agc     4080
Leu His Leu Gln Gly Arg Thr Asn Ala Trp Arg Pro Arg Val Ser Ser
1345                1350                1355                1360 gca gag gag tgg ctg cag gtg gac ctg cag aag acg gtg aag gtc aca     4128
Ala Glu Glu Trp Leu Gln Val Asp Leu Gln Lys Thr Val Lys Val Thr
                1365                1370                1375 ggc atc acc acc cag ggc gtg aag tcc ctg ctc agc agc atg tat gtg     4176
Gly Ile Thr Thr Gln Gly Val Lys Ser Leu Leu Ser Ser Met Tyr Val
            1380                1385                1390
```

-continued

```
aag gag ttc ctc gtg tcc agt agt cag gac ggc cgc cgc tgg acc ctg    4224
Lys Glu Phe Leu Val Ser Ser Ser Gln Asp Gly Arg Arg Trp Thr Leu
        1395                1400                1405 ttt ctt cag gac ggc cac acg aag gtt ttt cag ggc aat cag gac tcc    4272
Phe Leu Gln Asp Gly His Thr Lys Val Phe Gln Gly Asn Gln Asp Ser
    1410                1415                1420 tcc acc ccc gtg gtg aac gct ctg gac ccc ccg ctg ttc acg cgc tac    4320
Ser Thr Pro Val Val Asn Ala Leu Asp Pro Pro Leu Phe Thr Arg Tyr
1425                1430                1435                1440 ctg agg atc cac ccc acg agc tgg gcg cag cac atc gcc ctg agg ctc    4368
Leu Arg Ile His Pro Thr Ser Trp Ala Gln His Ile Ala Leu Arg Leu
                1445                1450                1455 gag gtt cta gga tgt gag gca cag gat ctc tac tga                    4404
Glu Val Leu Gly Cys Glu Ala Gln Asp Leu Tyr
            1460                1465

<210> SEQ ID NO 38
<211> LENGTH: 1467
<212> TYPE: PRT
<213> ORGANISM: Porcine

<400> SEQUENCE: 38

Met Gln Leu Glu Leu Ser Thr Cys Val Phe Leu Cys Leu Leu Pro Leu
  1               5                  10                  15

Gly Phe Ser Ala Ile Arg Arg Tyr Tyr Leu Gly Ala Val Glu Leu Ser
                 20                  25                  30

Trp Asp Tyr Arg Gln Ser Glu Leu Leu Arg Glu Leu His Val Asp Thr
             35                  40                  45

Arg Phe Pro Ala Thr Ala Pro Gly Ala Leu Pro Leu Gly Pro Ser Val
         50                  55                  60

Leu Tyr Lys Lys Thr Val Phe Val Glu Phe Thr Asp Gln Leu Phe Ser
 65                  70                  75                  80

Val Ala Arg Pro Arg Pro Pro Trp Met Gly Leu Leu Gly Pro Thr Ile
                 85                  90                  95

Gln Ala Glu Val Tyr Asp Thr Val Val Thr Leu Lys Asn Met Ala
                100                 105                 110

Ser His Pro Val Ser Leu His Ala Val Gly Val Ser Phe Trp Lys Ser
            115                 120                 125

Ser Glu Gly Ala Glu Tyr Glu Asp His Thr Ser Gln Arg Glu Lys Glu
        130                 135                 140

Asp Asp Lys Val Leu Pro Gly Lys Ser Gln Thr Tyr Val Trp Gln Val
145                 150                 155                 160

Leu Lys Glu Asn Gly Pro Thr Ala Ser Asp Pro Pro Cys Leu Thr Tyr
                165                 170                 175

Ser Tyr Leu Ser His Val Asp Leu Val Lys Asp Leu Asn Ser Gly Leu
            180                 185                 190

Ile Gly Ala Leu Leu Val Cys Arg Glu Gly Ser Leu Thr Arg Glu Arg
        195                 200                 205

Thr Gln Asn Leu His Glu Phe Val Leu Leu Phe Ala Val Phe Asp Glu
    210                 215                 220

Gly Lys Ser Trp His Ser Ala Arg Asn Asp Ser Trp Thr Arg Ala Met
225                 230                 235                 240

Asp Pro Ala Pro Ala Arg Ala Gln Pro Ala Met His Thr Val Asn Gly
                245                 250                 255

Tyr Val Asn Arg Ser Leu Pro Gly Leu Ile Gly Cys His Lys Lys Ser
            260                 265                 270
```

-continued

```
Val Tyr Trp His Val Ile Gly Met Gly Thr Ser Pro Glu Val His Ser
            275                 280                 285
Ile Phe Leu Glu Gly His Thr Phe Leu Val Arg His Arg Gln Ala
290                 295                 300
Ser Leu Glu Ile Ser Pro Leu Thr Phe Leu Thr Ala Gln Thr Phe Leu
305                 310                 315                 320
Met Asp Leu Gly Gln Phe Leu Leu Phe Cys His Ile Ser Ser His His
                325                 330                 335
His Gly Gly Met Glu Ala His Val Arg Val Glu Ser Cys Ala Glu Glu
            340                 345                 350
Pro Gln Leu Arg Arg Lys Ala Asp Glu Glu Asp Tyr Asp Asp Asn
            355                 360                 365
Leu Tyr Asp Ser Asp Met Asp Val Val Arg Leu Asp Gly Asp Val
    370                 375                 380
Ser Pro Phe Ile Gln Ile Arg Ser Val Ala Lys Lys His Pro Lys Thr
385                 390                 395                 400
Trp Val His Tyr Ile Ser Ala Glu Glu Glu Asp Trp Asp Tyr Ala Pro
                405                 410                 415
Ala Val Pro Ser Pro Ser Asp Arg Ser Tyr Lys Ser Leu Tyr Leu Asn
            420                 425                 430
Ser Gly Pro Gln Arg Ile Gly Arg Lys Tyr Lys Lys Ala Arg Phe Val
            435                 440                 445
Ala Tyr Thr Asp Val Thr Phe Lys Thr Arg Lys Ala Ile Pro Tyr Glu
    450                 455                 460
Ser Gly Ile Leu Gly Pro Leu Leu Tyr Gly Glu Val Gly Asp Thr Leu
465                 470                 475                 480
Leu Ile Ile Phe Lys Asn Lys Ala Ser Arg Pro Tyr Asn Ile Tyr Pro
                485                 490                 495
His Gly Ile Thr Asp Val Ser Ala Leu His Pro Gly Arg Leu Leu Lys
            500                 505                 510
Gly Trp Lys His Leu Lys Asp Met Pro Ile Leu Pro Gly Glu Thr Phe
    515                 520                 525
Lys Tyr Lys Trp Thr Val Thr Val Glu Asp Gly Pro Thr Lys Ser Asp
    530                 535                 540
Pro Arg Cys Leu Thr Arg Tyr Tyr Ser Ser Ile Asn Leu Glu Lys
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Met Met Ser Asp Lys Arg Asn Val
            580                 585                 590
Ile Leu Phe Ser Val Phe Asp Glu Asn Gln Ser Trp Tyr Leu Ala Glu
    595                 600                 605
Asn Ile Gln Arg Phe Leu Pro Asn Pro Asp Gly Leu Gln Pro Gln Asp
    610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Val Gly Ala Gln Thr Asp Phe Leu Ser Val Phe Phe
            660                 665                 670
Ser Gly Tyr Thr Phe Lys His Lys Met Val Tyr Glu Asp Thr Leu Thr
            675                 680                 685
Leu Phe Pro Phe Ser Gly Glu Thr Val Phe Met Ser Met Glu Asn Pro
```

```
                690                 695                 700
Gly Leu Trp Val Leu Gly Cys His Asn Ser Asp Leu Arg Asn Arg Gly
705                 710                 715                 720

Met Thr Ala Leu Leu Lys Val Tyr Ser Cys Asp Arg Asp Ile Gly Asp
                725                 730                 735

Tyr Tyr Asp Asn Thr Tyr Glu Asp Ile Pro Gly Phe Leu Leu Ser Gly
                740                 745                 750

Lys Asn Val Ile Glu Pro Arg Ser Phe Ala Gln Asn Ser Arg Pro Pro
                755                 760                 765

Ser Ala Ser Ala Pro Lys Pro Pro Val Leu Arg Arg His Gln Arg Asp
770                 775                 780

Ile Ser Leu Pro Thr Phe Gln Pro Glu Glu Asp Lys Met Asp Tyr Asp
785                 790                 795                 800

Asp Ile Phe Ser Thr Glu Thr Lys Gly Glu Asp Phe Asp Ile Tyr Gly
                805                 810                 815

Glu Asp Glu Asn Gln Asp Pro Arg Ser Phe Gln Lys Arg Thr Arg His
                820                 825                 830

Tyr Phe Ile Ala Ala Val Glu Gln Leu Trp Asp Tyr Gly Met Ser Glu
                835                 840                 845

Ser Pro Arg Ala Leu Arg Asn Arg Ala Gln Asn Gly Glu Val Pro Arg
850                 855                 860

Phe Lys Lys Val Val Phe Arg Glu Phe Ala Asp Gly Ser Phe Thr Gln
865                 870                 875                 880

Pro Ser Tyr Arg Gly Glu Leu Asn Lys His Leu Gly Leu Leu Gly Pro
                885                 890                 895

Tyr Ile Arg Ala Glu Val Glu Asp Asn Ile Met Val Thr Phe Lys Asn
                900                 905                 910

Gln Ala Ser Arg Pro Tyr Ser Phe Tyr Ser Ser Leu Ile Ser Tyr Pro
                915                 920                 925

Asp Asp Gln Glu Gln Gly Ala Glu Pro Arg His Asn Phe Val Gln Pro
930                 935                 940

Asn Glu Thr Arg Thr Tyr Phe Trp Lys Val Gln His His Met Ala Pro
945                 950                 955                 960

Thr Glu Asp Glu Phe Asp Cys Lys Ala Trp Ala Tyr Phe Ser Asp Val
                965                 970                 975

Asp Leu Glu Lys Asp Val His Ser Gly Leu Ile Gly Pro Leu Leu Ile
                980                 985                 990

Cys Arg Ala Asn Thr Leu Asn Ala Ala His Gly Arg Gln Val Thr Val
                995                 1000                1005

Gln Glu Phe Ala Leu Phe Phe Thr Ile Phe Asp Glu Thr Lys Ser Trp
1010                1015                1020

Tyr Phe Thr Glu Asn Val Glu Arg Asn Cys Arg Ala Pro Cys His Leu
1025                1030                1035                1040

Gln Met Glu Asp Pro Thr Leu Lys Glu Asn Tyr Arg Phe His Ala Ile
                1045                1050                1055

Asn Gly Tyr Val Met Asp Thr Leu Pro Gly Leu Val Met Ala Gln Asn
                1060                1065                1070

Gln Arg Ile Arg Trp Tyr Leu Leu Ser Met Gly Ser Asn Glu Asn Ile
                1075                1080                1085

His Ser Ile His Phe Ser Gly His Val Phe Ser Val Arg Lys Lys Glu
                1090                1095                1100

Glu Tyr Lys Met Ala Val Tyr Asn Leu Tyr Pro Gly Val Phe Glu Thr
1105                1110                1115                1120
```

```
Val Glu Met Leu Pro Ser Lys Val Gly Ile Trp Arg Ile Glu Cys Leu
                1125                1130                1135

Ile Gly Glu His Leu Gln Ala Gly Met Ser Thr Thr Phe Leu Val Tyr
                1140                1145                1150

Ser Lys Glu Cys Gln Ala Pro Leu Gly Met Ala Ser Gly Arg Ile Arg
            1155                1160                1165

Asp Phe Gln Ile Thr Ala Ser Gly Gln Tyr Gly Gln Trp Ala Pro Lys
1170                1175                1180

Leu Ala Arg Leu His Tyr Ser Gly Ser Ile Asn Ala Trp Ser Thr Lys
1185                1190                1195                1200

Asp Pro His Ser Trp Ile Lys Val Asp Leu Leu Ala Pro Met Ile Ile
                1205                1210                1215

His Gly Ile Met Thr Gln Gly Ala Arg Gln Lys Phe Ser Ser Leu Tyr
                1220                1225                1230

Ile Ser Gln Phe Ile Ile Met Tyr Ser Leu Asp Gly Arg Asn Trp Gln
            1235                1240                1245

Ser Tyr Arg Gly Asn Ser Thr Gly Thr Leu Met Val Phe Phe Gly Asn
    1250                1255                1260

Val Asp Ala Ser Gly Ile Lys His Asn Ile Phe Asn Pro Pro Ile Val
1265                1270                1275                1280

Ala Arg Tyr Ile Arg Leu His Pro Thr His Tyr Ser Ile Arg Ser Thr
                1285                1290                1295

Leu Arg Met Glu Leu Met Gly Cys Asp Leu Asn Ser Cys Ser Met Pro
                1300                1305                1310

Leu Gly Met Gln Asn Lys Ala Ile Ser Asp Ser Gln Ile Thr Ala Ser
            1315                1320                1325

Ser His Leu Ser Asn Ile Phe Ala Thr Trp Ser Pro Ser Gln Ala Arg
    1330                1335                1340

Leu His Leu Gln Gly Arg Thr Asn Ala Trp Arg Pro Arg Val Ser Ser
1345                1350                1355                1360

Ala Glu Glu Trp Leu Gln Val Asp Leu Gln Lys Thr Val Lys Val Thr
                1365                1370                1375

Gly Ile Thr Thr Gln Gly Val Lys Ser Leu Leu Ser Ser Met Tyr Val
                1380                1385                1390

Lys Glu Phe Leu Val Ser Ser Ser Gln Asp Gly Arg Arg Trp Thr Leu
            1395                1400                1405

Phe Leu Gln Asp Gly His Thr Lys Val Phe Gln Gly Asn Gln Asp Ser
    1410                1415                1420

Ser Thr Pro Val Val Asn Ala Leu Asp Pro Pro Leu Phe Thr Arg Tyr
1425                1430                1435                1440

Leu Arg Ile His Pro Thr Ser Trp Ala Gln His Ile Ala Leu Arg Leu
                1445                1450                1455

Glu Val Leu Gly Cys Glu Ala Gln Asp Leu Tyr
                1460                1465
```